United States Patent
Mc Kenna

(10) Patent No.: US 7,732,603 B2
(45) Date of Patent: Jun. 8, 2010

(54) ORGANIC COMPOUNDS AS AGENTS FOR THE TREATMENT OF ALDOSTERONE MEDIATED CONDITIONS

(75) Inventor: Jeffrey Mc Kenna, San Diego, CA (US)

(73) Assignee: Novartis AG, Basel (CH)

( * ) Notice: Subject to any disclaimer, the term of this patent is extended or adjusted under 35 U.S.C. 154(b) by 1307 days.

(21) Appl. No.: 10/523,870

(22) PCT Filed: Aug. 6, 2003

(86) PCT No.: PCT/EP03/08720

§ 371 (c)(1), (2), (4) Date: Mar. 18, 2005

(87) PCT Pub. No.: WO2004/014914

PCT Pub. Date: Feb. 19, 2004

(65) Prior Publication Data

US 2006/0166973 A1    Jul. 27, 2006

Related U.S. Application Data

(60) Provisional application No. 60/401,693, filed on Aug. 7, 2002.

(51) Int. Cl.
C07D 471/00 (2006.01)
C07D 487/00 (2006.01)
C07D 491/00 (2006.01)
C07D 495/00 (2006.01)
C07D 497/00 (2006.01)

(52) U.S. Cl. .................................................... 544/350

(58) Field of Classification Search ........................ None
See application file for complete search history.

(56) References Cited

U.S. PATENT DOCUMENTS

| | | | |
|---|---|---|---|
| 4,617,307 A | 10/1986 | Browne | 514/300 |
| 4,889,861 A | 12/1989 | Browne | 514/300 |
| 5,529,992 A | 6/1996 | Weber | 514/175 |
| 6,150,347 A | 11/2000 | Weber | 514/175 |
| 2005/0014939 A1* | 1/2005 | Albaugh et al. | 544/60 |

FOREIGN PATENT DOCUMENTS

| | | | |
|---|---|---|---|
| JP | 7-101959 A | | 4/1995 |
| JP | 07101959 | * | 4/1995 |
| WO | WO 97/00257 | | 1/1997 |
| WO | WO 9700257 | * | 1/1997 |
| WO | 03/076427 A1 | | 9/2003 |

OTHER PUBLICATIONS

Dorwald F. A. Side Reactions in Organic Synthesis, 2005, Wiley: VCH, Weinheim pg. IX of Preface.*
Borisy, et. al., Proceedings of the National Academy of Sciences of the United States of America, 100(13) 7977-7982.*
Janin et al., "Imidazo[1,5-g][1,4]diazepines, TIBO Analogues Lacking the Phenyl Ring: Synthesis and Evaluation as Anti-HIV Agents", *Tetrahedron*, vol. 52, No. 48, pp. 15157-15170 (1996).
Yamauchi and Masui, "Synthesis of 6,7,8,9-tetrahydro-5H-imidazo[1,5-a][1,4]diazepines", *Chem Industry*, No. 1, pp. 31-32 (1976).
Yamauchi and Masui, "Reactivity of 2,4(5)-Dialkylimidazoles. Synthesis of 6,7,8,9-Tetrahydro-5Himidazo[1,5-a][1,4]diazepine Derivatives", *Chem Pharm Bull*, vol. 24, No. 7, pp. 1480-1484 (1976).

\* cited by examiner

*Primary Examiner*—James O Wilson
*Assistant Examiner*—Jeffrey H Murray
(74) *Attorney, Agent, or Firm*—Sophie Binet Cross

(57) ABSTRACT

Compounds of formula I

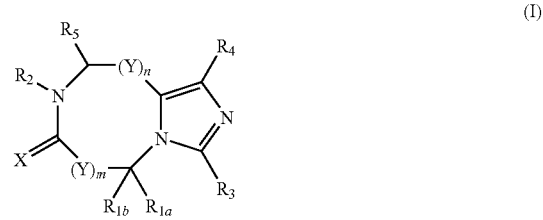

(I)

provide pharmacological agents which are inhibitors of the P450 enzyme, aldosterone synthase, and thus may be employed for the treatment of aldosterone mediated conditions. Accordingly, the compounds of formula I may be employed for prevention, delay of progression, or treatment of hypokalemia, hypertension, congestive heart failure, renal failure, in particular, chronic renal failure, restenosis, atherosclerosis, syndrome X, obesity, nephropathy, post myocardial infarction, coronary heart diseases, increased formation of collagen, fibrosis, and remodeling following hypertension and endothelial dysfunction. Preferred are the compounds of formula I which are selective inhibitors of aldosterone synthase devoid of undesirable side effects due to general inhibition of cytochrome P450 enzymes.

11 Claims, No Drawings

ORGANIC COMPOUNDS AS AGENTS FOR THE TREATMENT OF ALDOSTERONE MEDIATED CONDITIONS

The present invention provides compounds of formula I

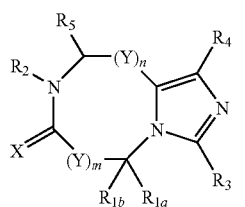

(I)

wherein

X is oxygen or $H_2$;

Y is —CRR'— in which
R and R' are independently hydrogen, optionally substituted alkyl, aralkyl or heteroaralkyl;

$R_{1a}$ is hydrogen, optionally substituted alkyl, cycloalkyl, alkenyl, alkynyl, aryl, aralkyl, heterocyclyl or heteroaralkyl provided that $R_{1a}$ is not 9H-carbazol-2-yl when $R_2$ is methyl, m is zero or an integer of 1, n is zero, X is $H_2$, and $R_{1b}$, $R_3$, $R_4$ and $R_5$ are hydrogen;

$R_{1b}$ is hydrogen, optionally substituted alkyl, aralkyl, heteroaralkyl, aryl or heteroaryl; or $R_{1a}$ and $R_{1b}$ combined are alkylene which taken together with the carbon atom to which they are attached form a 3- to 6-membered ring;

$R_2$ is $R_6$—$(CHR_7)_p$— in which
$R_6$ is optionally substituted alkyl, cycloalkyl, aryl or heterocyclyl;
$R_7$ is hydrogen, optionally substituted alkyl, aryl, heteroaryl or aralkyl;
p is zero or an integer from 1 to 4;

$R_3$ and $R_4$ are is dependently hydrogen, halogen, optionally substituted alkyl, aryl or heteroaryl; or $R_4$—C may be replaced by nitrogen;

$R_5$ is hydrogen, optionally substituted alkyl, aryl, heteroaryl, aralkyl or heteroaralkyl;

m and n are independently zero or an integer of 1 provided that the sum of m and n is not 2;

or a pharmaceutically acceptable salt thereof; or a diastereomer thereof; or a mixture of diastereomers thereof; or an optical isomer thereof; or a mixture of optical isomers thereof.

The compounds of the present invention are inhibitors of the P450 enzyme aldosterone synthase, and, thus, may be employed for the treatment of aldosterone mediated conditions. Accordingly, the compounds of formula I may be employed for prevention, delay of progression, or treatment of hypokalemia, hypertension, congestive heart failure, renal failure, in particular, chronic renal failure, restenosis, atherosclerosis, syndrome X, obesity, nephropathy, post myocardial infarction, coronary heart diseases, increased formation of collagen, fibrosis and remodeling following hypertension and endothelial dysfunction. Preferred are the compounds of formula I which are selective inhibitors of aldosterone synthase devoid of undesirable side effects due to general inhibition of cytochrome P450 enzymes.

Listed below are definitions of various terms used to describe the compounds of the present invention. These definitions apply to the terms as they are used throughout the specification unless they are otherwise limited in specific instances either individually or as part of a larger group.

The term "optionally substituted alkyl" refers to unsubstituted or substituted straight- or branched-chain hydrocarbon groups having 1-20 carbon atoms, preferably 1-7 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halo, hydroxy, cycloalkyl, alkanoyl, alkoxy, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, carboxy, alkoxycarbonyl, aryl, alkenyl, alkynyl, aralkoxy, guanidino, heterocyclyl including indolyl, imidazolyl, furyl, thienyl, thiazolyl, pyrrolidyl, pyridyl, pyrimidyl, piperidyl, morpholinyl and the like.

The term "lower alkyl" refers to those optionally substituted alkyl groups as described above having 1-7, preferably 1-4 carbon atoms.

The term "halogen" or "halo" refers to fluorine, chlorine, bromine and iodine.

The term "alkenyl" refers to any of the above alkyl groups having at least two carbon atoms and further containing a carbon to carbon double bond at the point of attachment. Groups having 2-4 carbon atoms are preferred.

The term "alkynyl" refers to any of the above alkyl groups having at least two carbon atoms and further containing a carbon to carbon triple bond at the point of attachment. Groups having 2-4 carbon atoms are preferred.

The term "alkylene" refers to a straight-chain bridge of 2-5 carbon atoms connected by single bonds, e.g., —$(CH_2)_x$—, wherein x is 2 to 5, which may be interrupted with one or more heteroatoms selected from O, S, S(O), $S(O)_2$ or NR", wherein R" may be hydrogen, alkyl, cycloalkyl, aryl, acyl, carbamoyl, sulfonyl, sulfamoyl, alkoxycarbonyl, aryloxycarbonyl or aralkoxycarbonyl, or the alkylene may be substituted with one or more substituents selected from alkyl, cycloalkyl, oxo, halogen, hydroxy, carboxy, alkoxy, alkoxycarbonyl and the like.

The term "cycloalkyl" refers to optionally substituted monocyclic, bicyclic or tricyclic hydrocarbon groups of 3-12 carbon atoms, each of which may be substituted by one or more substituents, such as alkyl, halo, oxo, hydroxy, alkoxy, alkanoyl, acylamino, carbamoyl, alkylamino, dialkylamino, thiol, alkylthio, nitro, cyano, carboxy, alkoxycarbonyl, sulfonyl, sulfonamido, sulfamoyl, heterocyclyl and the like.

Exemplary monocyclic hydrocarbon groups include, but are not limited to, cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.
The term "alkanoyl" refers to alkyl-C(O)—.
The term "alkanoyloxy" refers to alkyl-C(O)—O—.
The terms "alkylamino" and "dialkylamino" refer to alkyl-NH— and $(alkyl)_2N$—, respectively.
The term "alkanoylamino" refers to alkyl-C(O)—NH—.
The term "alkylthio" refers to alkyl-S—.
The term "alkylaminothiocarbonyl" refers to alkyl-NHC(S)—.

The term "trialkylsilyl" refers to (alkyl)$_3$Si—.
The term "trialkylsilyloxy" refers to (alkyl)$_3$SiO—.
The term "alkylthiono" refers to alkyl-S(O)—.
The term "alkylsulfonyl" refers to alkyl-S(O)$_2$—.
The term "alkoxycarbonyl" refers to alkyl-O—C(O)—.
The term "alkoxycarbonyloxy" refers to alkyl-O—C(O)O—.
The term "carboxycarbonyl" refers to HO—C(O)C(O)—.
The term "carbamoyl" refers to H$_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.
The term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.
The term "sulfonamido" refers to alkyl-S(O)$_2$—NH—, aryl-S(O)$_2$—NH—, aralkyl-S(O)$_2$—NH—, heteroaryl-S(O)$_2$—NH—, heteroaralkyl-S(O)$_2$—NH—, alkyl-S(O)$_2$—N(alkyl)-, aryl-S(O)$_2$—N(alkyl)-, aralkyl-S(O)$_2$—N(alkyl)-, heteroaryl-S(O)$_2$—N(alkyl)-, heteroaralkyl-S(O)$_2$—N(alkyl)- and the like.
The term "sulfonyl" refers to alkylsulfonyl, arylsulfonyl, heteroarylsulfonyl, aralkylsulfonyl, heteroaralkylsulfonyl and the like.
The term "optionally substituted amino" refers to a primary or secondary amino group which may optionally be substituted by a substituent, such as acyl, sulfonyl, alkoxycarbonyl, cycloalkoxycarbonyl, aryloxycarbonyl, heteroaryloxycarbonyl, aralkoxycarbonyl, heteroaralkoxycarbonyl, carbamoyl and the like.
The term "aryl" refers to monocyclic or bicyclic aromatic hydrocarbon groups having 6-12 carbon atoms in the ring portion, such as phenyl, biphenyl, naphthyl and tetrahydronaphthyl, each of which may optionally be substituted by 1-4 substituents, such as optionally substituted alkyl, trifluoromethyl, cycloalkyl, halo, hydroxy, alkoxy, acyl, alkanoyloxy, aryloxy, optionally substituted amino, thiol, alkylthio, arylthio, nitro, cyano, carboxy, alkoxycarbonyl, carbamoyl, alkylthiono, sulfonyl, sulfonamido, heterocyclyl and the like.
The term "monocyclic aryl" refers to optionally substituted phenyl as described under aryl.
The term "aralkyl" refers to an aryl group bonded directly through an alkyl group, such as benzyl.
The term "aralkanoyl" refers to aralkyl-C(O)—.
The term "aralkylthio" refers to aralkyl-S—.
The term "aralkoxy" refers to an aryl group bonded directly through an alkoxy group.
The term "arylsulfonyl" refers to aryl-S(O)$_2$—.
The term "arylthio" refers to aryl-S—.
The term "aroyl" refers to aryl-C(O)—.
The term "aroyloxy" refers to aryl-C(O)—O—.
The term "aroylamino" refers to aryl-C(O)—NH—.
The term "aryloxycarbonyl" refers to aryl-O—C(O)—.
The term "heterocyclyl" or "heterocyclo" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.
Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups substituted with 1, 2 or 3 substituents selected from the group consisting of the following:
(a) alkyl;
(b) hydroxy (or protected hydroxy);
(c) halo;
(d) oxo, i.e., =O;
(e) optionally substituted amino, alkylamino or dialkylamino;
(f) alkoxy;
(g) cycloalkyl;
(h) carboxy;
(i) heterocyclooxy;
(j) alkoxycarbonyl, such as unsubstituted lower alkoxycarbonyl;
(k) mercapto;
(l) nitro;
(m) cyano;
(n) sulfamoyl or sulfonamido;
(o) aryl;
(p) alkanoyloxy;
(q) aroyloxy;
(r) arylthio;
(s) aryloxy;
(t) alkylthio;
(u) formyl;
(v) carbamoyl;
(w) aralkyl; and
(x) aryl substituted with alkyl, cycloalkyl, alkoxy, hydroxy, amino, acylamino, alkylamino, dialkylamino or halo.

The term "heterocyclooxy" denotes a heterocyclic group bonded through an oxygen bridge.

The term "heteroaryl" refers to an aromatic heterocycle, e.g., monocyclic or bicyclic aryl, such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like, optionally substituted by, e.g., lower alkyl, lower alkoxy or halo.

The term "heteroarylsulfonyl" refers to heteroaryl-S(O)$_2$—.

The term "heteroaroyl" refers to heteroaryl-C(O)—.

The term "heteroaroylamino" refers to heteroaryl-C(O) NH—.

The term "heteroaralkyl" refers to a heteroaryl group bonded through an alkyl group.

The term "heteroaralkanoyl" refers to heteroaralkyl-C (O)—.

The term "heteroaralkanoylamino" refers to heteroaralkyl-C(O)NH—.

The term "acyl" refers to alkanoyl, aroyl, heteroaroyl, aralkanoyl, heteroaralkanoyl and the like.

The term "acylamino" refers to alkanoylamino, aroylamino, heteroaroylamino, aralkanoylamino, heteroaralkanoylamino and the like.

Pharmaceutically acceptable salts of any compound of the present invention refer to salts formed with acids, namely acid addition salts, such as of mineral acids, organic carboxylic and organic sulfonic acids, e.g., hydrochloric acid, maleic acid and methanesulfonic acid.

Similarly salts formed with bases, namely cationic salts, such as alkali and alkaline earth metal salts, such as sodium, lithium, potassium, calcium, magnesium, as well as ammonium salts, such as ammonium, trimethylammonium, diethylammonium, and tris(hydroxymethyl)methylammonium salts and salts with amino acids, are possible provided an acidic group constitutes part of the structure.

The present invention provides bicyclic compounds, more specifically, bicyclic imidazole and triazole derivatives of formula 1, pharmaceutical compositions containing them, methods for preparing said compounds, and methods of treating aldosterone mediated conditions by administration of a therapeutically effective amount of a compound of the present invention or a pharmaceutical composition thereof.

Preferred are the compounds of formula I wherein

Y is —CRR'— in which R and R' are hydrogen;

or a pharmaceutically acceptable salt thereof; or a diastereomer thereof; or a mixture of diastereomers thereof; or an optical isomer thereof; or a mixture of optical isomers thereof.

Further preferred are the compounds of formula I wherein m and n are zero;

or a pharmaceutically acceptable salt thereof; or a diastereomer thereof; or a mixture of diastereomers thereof; or an optical isomer thereof; or a mixture of optical isomers thereof.

More preferred are the compounds of formula IA

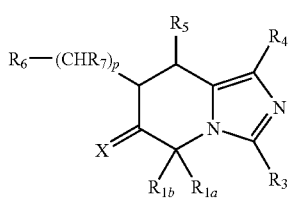

(IA)

wherein

X is oxygen or H$_2$;

R$_{1a}$ is lower alkyl, aryl or heteroaryl provided that R$_{1a}$ is not 9H-carbazol-2-yl when R$_6$ is methyl, p is zero, X is H$_2$, and R$_{1b}$, R$_3$, R$_4$ and R$_5$ are hydrogen;

R$_{1b}$ is hydrogen, lower alkyl, aralkyl or heteroaralkyl;

R$_6$ is cycloalkyl, aryl or heteroaryl;

R$_7$ is hydrogen or lower alkyl;

p is zero or an integer of 1 or 2;

R$_3$, R$_4$ and R$_5$ are hydrogen;

or a pharmaceutically acceptable salt thereof; or a diastereomer thereof; or a mixture of diastereomers thereof; or an optical isomer thereof; or a mixture of optical isomers thereof.

Preferred are the compounds of formula IA wherein

R$_1$ is monocyclic aryl;

R$_{1b}$ is hydrogen, lower alkyl or aralkyl;

or a pharmaceutically acceptable salt thereof; or a diastereomer thereof; or a mixture of diastereomers thereof; or an optical isomer thereof; or a mixture of optical isomers thereof.

Further preferred are the compounds of formula IA of formula IB

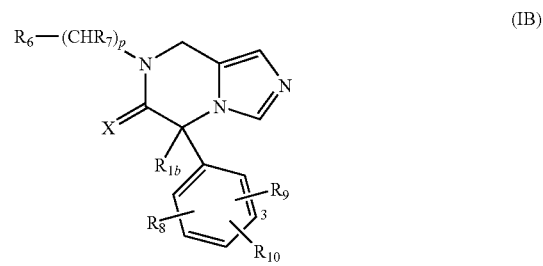

(IB)

wherein

X is oxygen or H$_2$;

R$_{1b}$ is hydrogen, lower alkyl or aralkyl;

R$_6$ is cycloalkyl, aryl or heteroaryl;

R$_7$ is hydrogen or lower alkyl;

p is zero or an integer of 1 or 2;

R$_8$, R$_9$ and R$_{10}$ are independently hydrogen, hydroxy, halogen, cyano, nitro, trifluoromethyl, optionally substituted alkyl, cycloalkyl, optionally substituted amino, alkoxy, alkylthio, carboxy, sulfonyl, carbamoyl, aryl, aryloxy, arylthio or heterocyclyl;

or a pharmaceutically acceptable salt thereof; or a diastereomer thereof; or a mixture of diastereomers thereof; or an optical isomer thereof; or a mixture of optical isomers thereof.

Preferred are the compounds of formula IB wherein

X is oxygen or H$_2$;

R$_{1b}$ is hydrogen, lower alkyl or aralkyl;

R$_6$ is cycloalkyl, aryl or heteroaryl;

R$_7$ is hydrogen or lower alkyl;

p is an integer of 1;

R$_8$ is hydrogen;

R$_9$ is hydrogen, halogen, cyano or trifluoromethyl;

R$_{10}$ is halogen, cyano or trifluoromethyl;

or a pharmaceutically acceptable salt thereof; or a diastereomer thereof; or a mixture of diastereomers thereof; or an optical isomer thereof; or a mixture of optical isomers thereof.

Further preferred are the compounds of formula IB wherein

X is oxygen;

or a pharmaceutically acceptable salt thereof; or a diastereomer thereof; or a mixture of diastereomers thereof; or an optical isomer thereof; or a mixture of optical isomers thereof.

Further preferred are also the compounds of formula IB wherein $R_6$ is $C_{3-6}$cycloalkyl, monocyclic aryl or monocyclic heteroaryl;

or a pharmaceutically acceptable salt thereof; or a diastereomer thereof; or a mixture of diastereomers thereof; or an optical isomer thereof; or a mixture of optical isomers thereof.

Further preferred are also the compounds of formula IB wherein $R_{10}$ is located at the 3-position;

or a pharmaceutically acceptable salt thereof; or a diastereomer thereof; or a mixture of diastereomers thereof; or an optical isomer thereof; or a mixture of optical isomers thereof.

Particular embodiments of the invention are:

4-(7-Cyclopropylmethyl-6-oxo-5,6,7,8-tetrahydro-imidazo[1,5-a]pyrazin-5-yl)-benzonitrile;
4-(7-Methyl-6-oxo-5,6,7,8-tetrahydro-imidazo[1,5-a]pyrazin-5-yl)-benzonitrile;
4-(7-Benzyl-6-oxo-5,6,7,8-tetrahydro-imidazo[1,5-a]pyrazin-5-yl)-benzonitrile;
4-(7-Allyl-6-oxo-5,6,7,8-tetrahydro-imidazo[1,5-a]pyrazin-5-yl)-benzonitrile;
4-(6-Oxo-7-propyl-5,6,7,8-tetrahydro-imidazo[1,5-a]pyrazin-5-yl)-benzonitrile;
4-(7-Isopropyl-6-oxo-5,6,7,8-tetrahydro-imidazo[1,5-a]pyrazin-5-yl)-benzonitrile;
4-{7-[2-(4-Fluoro-phenyl)-ethyl]-6-oxo-5,6,7,8-tetrahydro-imidazo[1,5-a]pyrazin-5-yl}-benzonitrile;
4-[7-(3-Morpholin-4-yl-propyl)-6-oxo-5,6,7,8-tetrahydro-imidazo[1,5-a]pyrazin-5-yl]-benzonitrile;
7-(4-Methoxy-benzyl)-5-(4-thiophen-3-yl-phenyl)-7,8-dihydro-imidazo[1,5-a]pyrazin-6-one;
4-[7-(4-Methyl-benzyl)-6-oxo-5,6,7,8-tetrahydro-imidazo[1,5-a]pyrazin-5-yl]-benzonitrile;
4-[7-(4-Chloro-benzyl)-6-oxo-5,6,7,8-tetrahydro-imidazo[1,5-a]pyrazin-5-yl]-benzonitrile;
4-[6-Oxo-7-(4-trifluoromethyl-benzyl)-5,6,7,8-tetrahydro-imidazo[1,5-a]pyrazin-5-yl]-benzo nitrile;
4-[6-Oxo-7-(3-methyl-benzyl)-5,6,7,8-tetrahydro-imidazo[1,5-a]pyrazin-5-yl]-benzonitrile;
4-[6-Oxo-7-(4-fluoro-benzyl)-5,6,7,8-tetrahydro-imidazo[1,5-a]pyrazin-5-yl]-benzonitrile;
4-[6-Oxo-7-(3-trifluoromethyl-benzyl)-5,6,7,8-tetrahydro-imidazo[1,5-a]pyrazin-5-yl]-benzonitrile;
4-[6-Oxo-7-(3,4-dichloro-benzyl)-5,6,7,8-tetrahydro-imidazo[1,5-a]pyrazin-5-yl]-benzonitrile;
4-(7-Cyclopropyl-6-oxo-5,6,7,8-tetrahydro-imidazo[1,5-a]pyrazin-5-yl)-benzonitrile;
4-(7-Cyclohexyl-6-oxo-5,6,7,8-tetrahydro-imidazo[1,5-a]pyrazin-5-yl)-benzonitrile;
4-(7-Cyclopentyl-6-oxo-5,6,7,8-tetrahydro-imidazo[1,5-a]pyrazin-5-yl)-benzonitrile;
4-[7-(2-Methoxyethyl)-6-oxo-5,6,7,8-tetrahydro-imidazo[1,5-a]pyrazin-5-yl]-benzonitrile;
4-[7-(3-Methoxypropyl)-6-oxo-5,6,7,8-tetrahydro-imidazo[1,5-a]pyrazin-5-yl]-benzonitrile;
4-(6-Oxo-7-pyridin-4-ylmethyl-5,6,7,8-tetrahydro-imidazo[1,5-a]pyrazin-5-yl)-benzonitrile;
7-Benzyl-5-phenyl-7,8-dihydro-imidazo[1,5-a]pyrazin-6-one;
7-Methyl-5-phenyl-7,8-dihydro-imidazo[1,5-a]pyrazin-6-one;
5-(4-Bromo-phenyl)-7-methyl-7,8-dihydro-imidazo[1,5-a]pyrazin-6-one;
5-(4-Bromo-phenyl)-7-(4-methoxy-benzyl)-7,8-dihydro-imidazo[1,5-a]pyrazin-6-one;
5-(4-Bromo-phenyl)-7-cyclopropylmethyl-7,8-dihydro-imidazo[1,5-a]pyrazin-6-one;
7-Benzyl-5-(4-bromo-phenyl)-7,8-dihydro-imidazo[1,5-a]pyrazin-6-one;
5-(4-Bromo-phenyl)-7-(4-chloro-benzyl)-7,8-dihydro-imidazo[1,5-a]pyrazin-6-one;
5-(4-Bromo-phenyl)-7-(4-trifluoromethyl-benzyl)-7,8-dihydro-imidazo[1,5-a]pyrazin-6-one;
5-(4-Bromo-phenyl)-7-(4-methoxy-phenyl)-7,8-dihydro-imidazo[1,5-a]pyrazin-6-one;
5-(4-Bromo-phenyl)-7-(4-fluoro-phenethyl)-7,8-dihydro-imidazo[1,5-a]pyrazin-6-one;
5-(4-Bromo-phenyl)-7-(4-fluoro-benzyl)-7,8-dihydro-imidazo[1,5-a]pyrazin-6-one;
5-(3-Bromo-phenyl)-7-methyl-7,8-dihydro-imidazo[1,5-a]pyrazin-6-one;
5-(3-Bromo-phenyl)-7-cyclohexyl-7,8-dihydro-imidazo[1,5-a]pyrazin-6-one;
5-(3-Bromo-phenyl)-7-(4-methoxy-phenyl)-7,8-dihydro-imidazo[1,5-a]pyrazin-6-one;
5-(3-Bromo-phenyl)-7-cyclopropylmethyl-7,8-dihydro-imidazo[1,5-a]pyrazin-6-one;
7-Benzyl-5-(3-bromo-phenyl)-7,8-dihydro-imidazo[1,5-a]pyrazin-6-one;
5-(3-Bromo-phenyl)-7-(4-methoxy-benzyl)-7,8-dihydro-imidazo[1,5-a]pyrazin-6-one;
5-(3-Bromo-phenyl)-7-(4-fluoro-benzyl)-7,8-dihydro-imidazo[1,5-a]pyrazin-6-one;
5-(3-Bromo-phenyl)-7-(4-chloro-benzyl)-7,8-dihydro-imidazo[1,5-a]pyrazin-6-one;
5-(3-Bromo-phenyl)-7-(4-methyl-benzyl)-7,8-dihydro-imidazo[1,5-a]pyrazin-6-one;
5-(3-Bromo-phenyl)-7-(4-trifluoromethyl-benzyl)-7,8-dihydro-imidazo[1,5-a]pyrazin-6-one;
5-(3-Bromo-phenyl)-7-(3-trifluoromethyl-benzyl)-7,8-dihydro-imidazo[1,5-a]pyrazin-6-one;
5-(3-Bromo-phenyl)-7-(3-fluoro-benzyl)-7,8-dihydro-imidazo[1,5-a]pyrazin-6-one;
5-(3-Bromo-phenyl)-7-(3-methyl-benzyl)-7,8-dihydro-imidazo[1,5-a]pyrazin-6-one;
5-(3-Bromo-phenyl)-7-(phenethyl)-7,8-dihydro-imidazo[1,5-a]pyrazin-6-one;
5-(3-Bromo-phenyl)-7-(4-methoxy-phenethyl)-7,8-dihydro-imidazo[1,5-a]pyrazin-6-one;
5-(3-Bromo-phenyl)-7-(4-chloro-phenethyl)-7,8-dihydro-imidazo[1,5-a]pyrazin-6-one;
5-(3-Bromo-phenyl)-7-(3-chloro-phenethyl)-7,8-dihydro-imidazo[1,5-a]pyrazin-6-one;
5-(3-Bromo-phenyl)-7-(4-methyl-phenethyl)-7,8-dihydro-imidazo[1,5-a]pyrazin-6-one;
5-(3-Bromo-phenyl)-7-(4-fluoro-phenethyl)-7,8-dihydro-imidazo[1,5-a]pyrazin-6-one;
5-(3-Bromo-phenyl)-7-thiophen-2-ylmethyl-7,8-dihydro-imidazo[1,5-a]pyrazin-6-one;
5-(3-Bromo-phenyl)-7-furan-2-ylmethyl-7,8-dihydro-imidazo[1,5-a]pyrazin-6-one;
5-(3-Bromo-phenyl)-7-thiophen-3-ylmethyl-7,8-dihydro-imidazo[1,5-a]pyrazin-6-one;
5-(3-Bromo-phenyl)-7-furan-3-ylmethyl-7,8-dihydro-imidazo[1,5-a]pyrazin-6-one;

5-(3-Bromo-phenyl)-7-pyridin-3-ylmethyl-7,8-dihydro-imidazo[1,5-a]pyrazin-6-one;
5-(3-Bromo-phenyl)-7-pyridin-2-ylmethyl-7,8-dihydro-imidazo[1,5-a]pyrazin-6-one;
5-(3-Bromo-phenyl)-7-pyridin-4-ylmethyl-7,8-dihydro-imidazo[1,5-a]pyrazin-6-one;
5-(3-Bromo-phenyl)-7-cyclohexylmethyl-7,8-dihydro-imidazo[1,5-a]pyrazin-6-one;
4-[5-(3-Bromo-phenyl)-6-oxo-5,6-dihydro-8H-imidazo[1,5-a]pyrazin-7-ylmethyl]-piperidine-1-carboxylic acid t-butyl ester;
5-(3-Bromo-phenyl)-7-piperidin-4-ylmethyl-7,8-dihydro-imidazo[1,5-a]pyrazin-6-one;
(R)-5-(3-Bromo-phenyl)-7-((R)-1-phenyl-ethyl)-7,8-dihydro-imidazo[1,5-a]pyrazin-6-one;
(S)-5-(3-Bromo-phenyl)-7-((R)-1-phenyl-ethyl)-7,8-dihydro-imidazo[1,5-a]pyrazin-6-one;
(R)-5-(3-Bromo-phenyl)-7-((S)-1-phenyl-ethyl)-7,8-dihydro-imidazo[1,5-a]pyrazin-6-one;
(S-5-(3-Bromo-phenyl)-7-((S)-1-phenyl-ethyl)-7,8-dihydro-imidazo[1,5-a]pyrazin-6-one;
(R)-5-(4-Bromo-phenyl)-7-((R)-1-phenyl-ethyl)-7,8-dihydro-imidazo[1,5-a]pyrazin-6-one;
(S)-5(4-Bromo-phenyl)-7-((R)-1-phenyl-ethyl)-7,8-dihydro-imidazo[1,5-a]pyrazin-6-one;
(R)-5-(4-Bromo-phenyl)-7-((3)-1-phenyl-ethyl)-7,8-dihydro-imidazo[1,5-a]pyrazin-6-one;
(S)-5-(4-Bromo-phenyl)-7-((S)-1-phenyl-ethyl)-7,8-dihydro-imidazo[1,5-a]pyrazin-6-one;
4-[(R)-6-Oxo-7-((S)-1-phenyl-ethyl)-5,6,7,8-tetrahydro-imidazo[1,5-a]pyrazin-5-yl]-benzonitrile;
4-[(S-6-Oxo-7-((S)-1-phenyl-ethyl)-5,6,7,8-tetrahydro-imidazo[1,5-a]pyrazin-5-yl]-benzonitrile;
7-Benzyl-7,8-dihydro-imidazo[1,5-a]pyrazin-6-one;
7-(4-Methyl-benzyl)-7,8-dihydro-imidazo[1,5-a]pyrazin-6-one;
7-(4-Fluoro-benzyl)-7,8-dihydro-imidazo[1,5-a]pyrazin-6-one;
3-(7-Benzyl-6-oxo-5,6,7,8-tetrahydro-imidazo[1,5-a]pyrazin-5-yl)-benzonitrile;
3-[7-(4-Methyl-benzyl)-6-oxo-5,6,7,8-tetrahydro-imidazo[1,5-a]pyrazin-5-yl]-benzonitrile;
3-[7-(4-Fluoro-benzyl)-6-oxo-5,6,7,8-tetrahydro-imidazo[1,5-a]pyrazin-5-yl]-benzonitrile;
3-[7-(4-Chloro-benzyl)-6-oxo-5,6,7,8-tetrahydro-imidazo[1,5-a]pyrazin-5-yl]-benzonitrile;
3-[7-(4-Methoxy-benzyl)-6-oxo-5,6,7,8-tetrahydro-imidazo[1,5-a]pyrazin-5-yl]-benzonitrile;
3-[7-(4-Fluoro-phenethyl)-6-oxo-5,6,7,8-tetrahydro-imidazo[1,5-a]pyrazin-5-yl]-benzonitrile;
3-(7-Phenethyl-6-oxo-5,6,7,8-tetrahydro-imidazo[1,5-a]pyrazin-5-yl)-benzonitrile;
3-(7-Cyclopropylmethyl-6-oxo-5,6,7,8-tetrahydro-imidazo[1,5-a]pyrazin-5-yl)-benzonitrile;
5-(4'-Chloro-biphenyl-4-yl)-7-(4-methoxy-benzyl)-7,8-dihydro-imidazo[1,5-a]pyrazin-6-one;
7-(4-Methoxy-benzyl)-5-(4-thiophen-3-yl-phenyl)-7,8-dihydro-imidazo[1,5-a]pyrazin-6-one;
7-Cyclopropylmethyl-5-(4-thiophen-3-yl-phenyl)-7,8-dihydro-imidazo[1,5-a]pyrazin-6-one;
7-Benzyl-5-(4'-fluoro-biphenyl-3-yl)-7,8-dihydro-imidazo[1,5-a]pyrazin-6-one;
5-Biphenyl-4-yl-7-(4-fluoro-benzyl)-7,8-dihydro-imidazo[1,5-a]pyrazin-6-one;
7-Benzyl-5-biphenyl-3-yl-7,8-dihydro-imidazo[1,5-a]pyrazin-6-one;
Methyl 4-(7-benzyl-6-oxo-5,6,7,8-tetrahydro-imidazo[1,5-a]pyrazin-5-yl)-benzoate;
4-(7-Benzyl-5-methyl-6-oxo-5,6,7,8-tetrahydro-imidazo[1,5-a]pyrazin-5-yl)-benzonitrile;
5-(4-Bromo-phenyl)-7-cyclopropylmethyl-5-methyl-7,8-dihydro-imidazo[1,5-a]pyrazin-6-one;
5-(3-Bromo-phenyl)-7-cyclopropylmethyl-5-methyl-7,8-dihydro-imidazo[1,5-a]pyrazin-6-one;
5-(4-Bromo-phenyl)-7-(4-fluoro-benzyl)-5-methyl-7,8-dihydro-imidazo[1,5-a]pyrazin-6-one;
4-[7-(4-Fluoro-benzyl)-5-methyl-6-oxo-5,6,7,8-tetrahydro-imidazo[1,5-a]pyrazin-5-yl]-benzonitrile;
4-[((R)-7-[(S)-1-(4-Fluoro-phenyl)-ethyl]-5-methyl-6-oxo-5,6,7,8-tetrahydro-imidazo[1,5-a]pyrazin-5-yl]-benzonitrile;
4-{(S)-7-[(S)-1-(4-Fluoro-phenyl)-ethyl]-5-methyl-6-oxo-5,6,7,8-tetrahydro-imidazo[1,5-a]pyrazin-5-yl}-benzonitrile;
5-Benzyl-5-(4-bromo-phenyl)-7-(4-fluoro-benzyl)-7,8-dihydro-imidazo[1,5-a]pyrazin-6-one;
4-(5,7-Dibenzyl-6-oxo-5,6,7,8-tetrahydro-imidazo[1,5-a]pyrazin-5-yl)-benzonitrile;
4-(5-Benzyl-7-cyclopropylmethyl-6-oxo-5,6,7,8-tetrahydro-imidazo[1,5-a]pyrazin-5-yl)-benzonitrile;
5(4-Bromophenyl)-7-(4-methoxy-benzyl)-5,6,7,8-tetrahydro-imidazo[1,5-a]-pyrazine;
4-(8-Benzyl-7-oxo-6,7,8,9-tetrahydro-5H-imidazo[1,5-a][1,4]diazepin-5-yl)-benzonitrile; and
4-(8-Cyclopropylmethyl-7-oxo-6,7,8,9-tetrahydro-5H-imidazo[1,5-a][1,4]diazepin-5-yl)-benzonitrile;

or a pharmaceutically acceptable salt thereof; or an optical isomer thereof; or a mixture of optical isomers thereof.

The compounds of the invention depending on the nature of the substituents, may possess one or more asymmetric centers. The resulting diastereoisomers, enantiomers and geometric isomers, and mixtures thereof, are encompassed by the instant invention.

Compounds of formula I may be prepared starting from alcohols of formula II

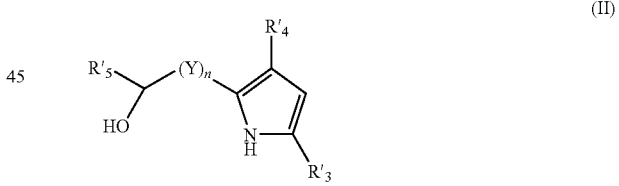

(II)

wherein Y and n have meanings as defined herein above, and $R'_3$, $R'_4$ and $R'_5$ represent $R_3$, $R_4$ and $R_5$ as defined herein above, or $R'_3$, $R'_4$ and $R'_5$ are groups convertible to $R_3$, $R_4$ and $R_5$, respectively. Alcohols of formula II may be prepared as illustrated herein in the Examples, or modifications thereof, or using methods well-known in the art.

Accordingly, compounds of formula II may first be treated with compounds of formula III Pg₁-Lg₁    (III)

wherein Lg₁ represents a leaving group, such as iodide, bromide or chloride, preferably chloride, and Pg₁ is an appropriate N-protecting group, such as trityl, benzyloxymethyl, methoxymethyl or (2-trimethylsilylethoxy)methyl, preferably trityl, in the presence of a base, such as triethylamine (TEA), diisopropylethylamine (DIEA) or N-methylmorpholine (NMM) in an organic solvent, such as tetrahydrofuran (THF) or N,N-dimethylformamide (DMF) at an ambient temperature, preferably at room temperature (RT), to afford compounds of formula IV

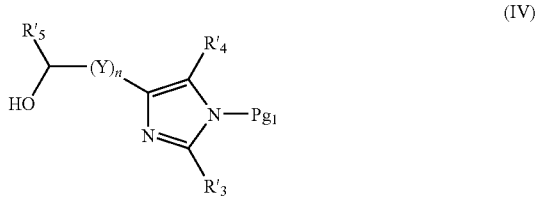
(IV)

wherein $Pg_1$, Y, n, $R'_3$, $R'_4$ and $R'_5$ have meanings as defined for formula II.

Compounds of formula IV wherein $Pg_1$, Y, n, $R'_3$, $R'_4$ and $R'_5$ have meanings as defined herein above, may be converted to compounds of formula V

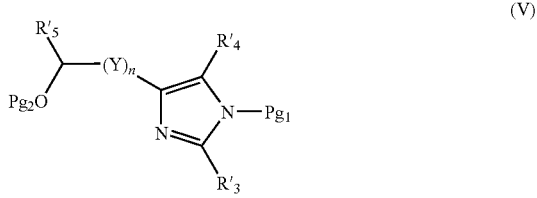
(V)

wherein $Pg_2$ is an appropriate O-protecting group, such as a trialkylsilyl or an acyl group, preferably a t-butyidimethylsilyl or an acetyl group, and $Pg_1$, Y, n, $R'_3$, $R'_4$ and $R'_5$ have meanings as defined herein above, using methods described herein in the Examples, or modifications thereof, or using conditions well-known in the art. For example, compounds of formula IV may be treated at RT with a compound of formula VI

$Pg_2$-$Lg_2$ (VI)

wherein $Lg_2$ represents a leaving group, such as iodide, bromide, chloride or trifluoromethanesulfonate, and $Pg_2$ is an O-protecting group such as trialkylsilyl, e.g., t-butyidimethylsilyl, in an organic solvent, such as THF, DMF or dichloromethane (DCM) in the presence of a base such as TEA, DIEA, NMM, imidazole or N,N-dimethylaminopyridine (DMAP), to afford compounds of formula V, wherein $Pg_1$, $Pg_2$, Y, n, $R'_3$, $R'_4$ and $R'_5$ have meanings as defined herein above.

Alternatively, compounds of formula IV may be converted to compounds of formula V, wherein $Pg_2$ is an O-protecting group, such as an acyl group, e.g., acetyl, by the treatment with acyl anhydride or acyl chloride, e.g., acetic anhydride or acetyl chloride, in the presence of a base, such as pyridine.

Compounds of formula V, wherein $Pg_1$, $Pg_2$, Y, n, $R'_3$, $R'_4$ and $R'_5$ have meanings as defined herein above may be first treated at an ambient temperature, preferably at RT, with an alkylating agent of formula VII

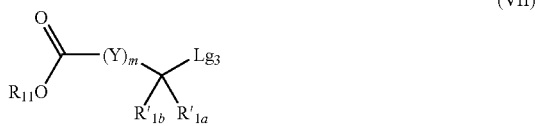
(VII)

wherein m is zero, $Lg_3$ represents a leaving group, such as bromide, chloride, methanesulfonate or p-toluenesulfonate, preferably bromide, $R_{11}$ is lower alkyl, such as methyl or ethyl, Y has a meaning as defined herein above, $R'_{1b}$ is hydrogen, and $R'_{1a}$ represents $R_{1a}$ as defined herein, or $R'_{1a}$ is a group convertible to $R_{1a}$, in an organic solvent, such as ethyl acetate (EtOAc) or acetonitrile. Subsequent removal of the protecting groups $Pg_1$ and $Pg_2$ then affords compounds of formula VIII

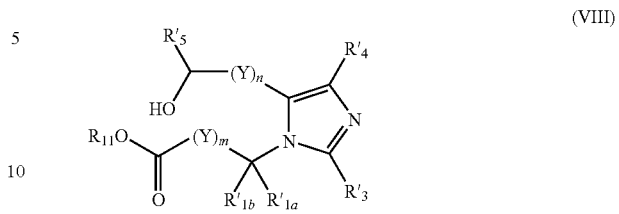
(VIII)

wherein m is zero, $R'_{1b}$ is hydrogen, and $R_{11}$, Y, n, $R'_{1a}$, $R'_3$, $R'_4$ and $R'_5$ have meanings as defined herein above. The protecting groups may be removed using conditions illustrated herein in the Examples, or modifications thereof, or using methods well-known in the art. In particular, when $Pg_1$ is a trityl and $Pg_2$ is a t-butyidimethylsilyl group, both protecting groups may be removed simultaneously by the treatment with an acid, such as trifluoroacetic acid, p-toluenesulfonic acid or a mineral acid, preferably hydrochloric acid, in the presence of a protic organic solvent, such as a lower alcohol, preferably methanol or ethanol. Protecting groups ($Pg_2$), such as an acyl group, in particular, acetyl group, may be removed by the subsequent treatment with an aqueous base, such as sodium, lithium or potassium hydroxide in an organic solvent, such as THF or a lower alcohol, preferably THF. Alkylating agents of formula VII may be prepared using methods described herein in the Examples, or modifications thereof, or using conditions well-known in the art.

Alternatively, compounds of formula VIII wherein m is zero or an integer of 1, $R_{11}$, Y, n, $R'_{1a}$, $R'_3$, $R'_4$ and $R'_5$ have meanings as defined herein above, and $R'_{1b}$ represents hydrogen, optionally substituted alkyl, aralkyl, heteroaralkyl, aryl or heteroaryl, may be obtained by first treating compounds of formula V at an ambient temperature, preferably at a temperature near the boiling point of the solvent, with an alkylating agent of formula IX

(IX)

wherein $Lg_4$ represents a leaving group, such as bromide, chloride, methanesulfonate, p-toluenesulfonate or trifluoromethanesulfonate, preferably bromide, and $R'_{1a}$ and $R'_{1b}$ represent $R_{1a}$ and $R_{1b}$ as defined herein, or $R'_{1a}$ and $R'_{1b}$ are groups convertible to $R_{1a}$ and $R_{1b}$, respectively, in an organic solvent such as EtOAc or acetonitrile. Subsequent removal of the protecting groups $Pg_1$ and $Pg_2$ using conditions described herein above for the preparation of compounds of formula VIII then affords compounds of formula X

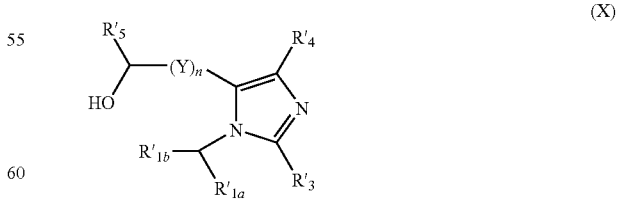
(X)

wherein Y, n, $R'_{1a}$, $R'_{1b}$, $R'_3$, $R'_4$ and $R'_5$ have meanings as defined herein above.

The free hydroxyl group in compounds of formula X, wherein Y, n, $R'_{1a}$, $R'_{1b}$, $R'_3$, $R'_4$ and $R'_5$ have meanings as defined herein above, may then be protected with an appropriate O-protecting group, such as trialkylsilyl, preferably t-butyldimethylsilyl, using conditions as described herein above for the preparation of compounds of formula V, to obtain compounds of formula XI

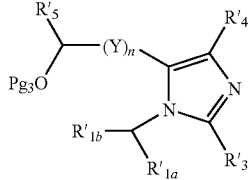
(XI)

wherein $Pg_3$ represents the above defined O-protecting group, and Y, n, $R'_{1a}$, $R'_{1b}$, $R'_3$, $R'_4$ and $R'_5$ have meanings as defined herein above.

Compounds of formula XI, wherein $Pg_3$, Y, n, $R'_{1a}$, $R'_{1b}$, $R'_3$, $R'_4$ and $R'_5$ have meanings as defined herein above, may then be converted to compounds of formula XII

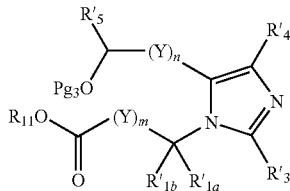
(XII)

wherein $R_{11}$, $Pg_3$, Y, m, n, $R'_{1a}$, $R'_{1b}$, $R'_3$, $R'_4$ and $R'_5$ have meanings as defined herein above, by first deprotonating compounds of formula XI in the presence of a base, such as lithium diisopropylamide (LDA), or lithium, sodium or potassium bis(trimethylsilyl)amide, preferably lithium bis(trimethylsilyl)amide (LHMDS), in an organic solvent, such as THF at a temperature ranging from $-45°$ C. to $-100°$ C. The resulting anion may then be reacted with an acylating agent or an alkylating agent of formula XIII

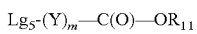
$Lg_5\text{-}(Y)_m\text{—}C(O)\text{—}OR_{11}$ (XIII)

wherein m is zero (an acylating agent) or an integer of 1 (an alkylating agent), $Lg_5$ is a leaving group, such as chloride or cyanide when m is zero, or $Lg_5$ is a leaving group, such as bromide or chloride when m is an integer of 1, and $R_{11}$ has a meaning as defined herein above, to afford compounds of formula XII.

Compounds of formula VIII, wherein $R_{11}$, Y, m, n, $R'_{1a}$, $R'_{1b}$, $R'_3$, $R'_4$ and $R'_5$ have meanings as defined herein above may then be obtained from compounds of formula XII by removal of the protecting group, $Pg_3$, using conditions described herein above or modifications thereof.

Compounds of formula VIII, wherein $R_{11}$, Y, m, n, $R'_{1a}$, $R'_{1b}$, $R'_3$, $R'_4$ and $R'_5$ have meanings as defined herein above, may be oxidized to compounds of formula XIV

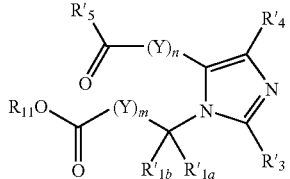
(XIV)

wherein $R_{11}$, Y, m, n, $R'^{1a}$, $R'_{1b}$, $R'_3$, $R'_4$ and $R'_5$ have meanings as defined herein above, using an oxidizing agent, preferably Dess-Martin reagent, in an organic solvent, such as DCM or 1,2-dichloromethane (DCE).

Finally, compounds of formula XIV, wherein $R_{11}$, Y, m, n, $R'_{1a}$, $R'_{1b}$, $R'_3$, $R'_4$ and $R'_5$ have meanings as defined herein above may be cyclized at an ambient temperature ranging from RT to the boiling point of the solvent to afford compounds of formula I'

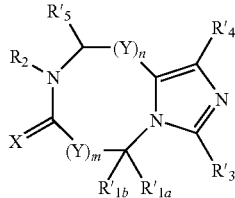
(I')

wherein X represents oxygen, and $R_2$, Y, m, n, $R'_{1a}$, $R'_{1b}$, $R'_3$, $R'_4$ and $R'_5$ have meanings as defined herein above, under conditions of reductive amination, e.g., compounds of formula XIV may be treated with amines of formula XV

$R_2\text{—}NH_2$ (XV)

or acid addition salts thereof, wherein $R_2$ has a meaning as defined herein above, in the presence of a reducing agent, such as sodium or lithium borohydride, sodium cyanoborohydride or sodium triacetoxyborohydride, preferably sodium triacetoxyborohydride, in an organic solvent, such as THF, DCM or DCE to afford compounds of formula I', wherein X, $R_2$, Y, m, n, $R'_{1a}$, $R'_{1b}$, $R'_3$, $R'_4$ and $R'_5$ have meanings as defined herein above. The cyclization may be carried out in the presence of an acid catalyst, such as acetic or trifluoroacetic acid.

Compounds of formula I', wherein X represents oxygen; $R'_{1b}$ is hydrogen and $R_2$, Y, m, n, $R'_{1a}$, $R'_3$, $R'_4$ and $R'_5$ have meanings as defined herein above, may be converted to compounds of formula I', wherein $R'_{1b}$ is optionally substituted alkyl, aralkyl or heteroaralkyl, by treatment with an alkylating agent of formula XVI

$R'_{1b}\text{-}Lg_6$ (XVI)

wherein $R'_{1b}$ is optionally substituted alkyl, aralkyl or heteroaralkyl, and $Lg_6$ represents a leaving group, such as bromide, chloride, methanesulfonate, p-toluenesulfonate or trifluoromethanesulfonate, preferably bromide, in the presence of a base, such as sodium hydride, LDA or LHMDS, in an organic solvent, such as THF or DMF.

Similarly, compounds of formula I', wherein X represents oxygen, $R'_{1a}$ and $R'_{1b}$ are hydrogen, and $R_2$, Y, m, n, $R'_3$, $R'_4$ and $R'_5$ have meanings as defined herein above, may be converted to compounds of formula I', wherein $R'_{1a}$ and $R'_{1b}$ combined are alkylene, by treatment with an alkylating agent of formula XVII

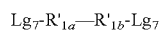
$Lg_7\text{-}R'_{1a}\text{—}R'_{1b}\text{-}Lg_7$ (XVII)

wherein $R'_{1a}$ and $R'_{1b}$ combined are alkylene, and $Lg_7$ represents a leaving group, such as bromide or chloride, preferably bromide, in the presence of a base, such as sodium hydride, potassium carbonate or cesium carbonate, in an organic solvent, such as dimethylsulfoxide or DMF.

In addition, compounds of formula I', wherein X represents oxygen, and $R_2$, Y, m, n, $R'_{1a}$, $R'_{1b}$, $R'_3$, $R_{14}$ and $R'_5$ have meanings as defined herein above, may be reduced to compounds of formula I', wherein X represents $H_2$, by treatment with a reducing agent, preferably borane, in an inert solvent, such as THF.

The processes described herein above may be conducted under inert atmosphere, preferably under nitrogen atmosphere.

In starting compounds and intermediates which are converted to the compounds of the invention in a manner described herein, functional groups present, such as amino, thiol, carboxyl and hydroxy groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, room temperature or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, diastereomers, optical isomers (antipodes), racemates or mixtures thereof. The aforesaid possible isomers or mixtures thereof are within the purview of this invention.

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the imidazolyl and triazolyl moieties may be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Finally, compounds of the invention are either obtained in the free form, as a salt thereof, or as prodrug derivatives thereof.

Compounds of the invention having basic groups, in particular, the imidazolyl or triazolyl moiety, can be converted into acid addition salts, especially pharmaceutically acceptable salts. These are formed, for example, with inorganic acids, such as mineral acids, for example, sulfuric acid, a phosphoric or hydrohalic acid, or with organic carboxylic acids, such as $(C_1-C_4)$-alkanecarboxylic acids which, for example, are unsubstituted or substituted by halogen, for example, acetic acid, such as saturated or unsaturated dicarboxylic acids, for example, oxalic, succinic, maleic or fumaric acid, such as hydroxycarboxylic acids, for example glycolic, lactic, malic, tartaric or citric acid, such as amino acids, for example, aspartic or glutamic acid, or with organic sulfonic acids, such as $(C_1-C_4)$-alkylsulfonic acids, for example, methanesulfonic acid; or arylsulfonic acids which are unsubstituted or substituted (for example by halogen). Preferred are salts formed with hydrochloric acid, methanesulfonic acid and maleic acid.

Compounds of the instant invention which contain acidic groups may be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art.

In view of the close relationship between the free compounds, the prodrug derivatives and the compounds in the form of their salts, whenever a compound is referred to in this context, a prodrug derivative and a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, to inhibit aldosterone synthase, and for the treatment of conditions associated with aldosterone synthase activity. Such conditions include hypokalemia, hypertension, congestive heart failure, renal failure, in particular chronic renal failure, restenosis, atherosclerosis, syndrome X, obesity, nephropathy, post-myocardial infarction, coronary heart diseases, increased formation of collagen, fibrosis, and remodeling following hypertension and endothelial dysfunction. The said pharmaceutical compositions comprise a therapeutically effective amount of a pharmacologically active compound of the instant invention, alone or in combination with one or more pharmaceutically acceptable carriers.

Thus in an additional aspect the present invention concerns a pharmaceutical composition comprising a therapeutically effective amount of a compound of the invention in combination with one or more pharmaceutically acceptable carriers.

In a further aspect the present invention concerns a pharmaceutical composition comprising a therapeutically effective amount of a compound of the invention in combination with a therapeutically effective amount of anti-obesity agent, anti-hypertensive agent, inotropic agent or hypolipidemic agent.

A pharmaceutical composition as described above for use as a medicament.

Use of a pharmaceutical composition or combination as described above for the preparation of a medicament for the treatment of conditions associated with aldosterone synthase activity.

A pharmaceutical composition as described above for the treatment of conditions associated with aldosterone synthase activity, preferably hypokalemia, hypertension, congestive heart failure, atherosclerosis, coronary heart diseases, post myocardial infarction, restenosis, increased formation of collagen, fibrosis, remodeling following hypertension and endothelial dysfunction, renal failure, nephropathy, syndrome X and obesity.

The pharmacologically active compounds of the invention are useful in the manufacture of pharmaceutical compositions comprising a therapeutically effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g. starches, agar, alginic acid or Its sodium salt, or effervescent mixtures; and/or
e) absorbants, colorants, flavors and sweeteners.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and pre-determined rate over a prolonged period of time, and means to secure the device to the skin.

The pharmaceutical formulations contain a therapeutically effective amount of a compound of the invention as defined above, either alone or in a combination with another therapeutic agent, e.g., each at an effective therapeutic dose as reported in the art. Such therapeutic agents include anti-obesity agents, such as orlistat, anti-hypertensive agents, inotropic agents and hypolipidemic agents, e.g., loop diuretics, such as ethacrynic acid, furosemide and torsemide; angiotensin converting enzyme (ACE) inhibitors, such as benazepril, captopril, enalapril, fosinopril, lisinopril, moexipril, perinodopril, quinapril, ramipril and trandolapril; inhibitors of the Na—K-ATPase membrane pump, such as digoxin; neutralendopeptidase (NEP) inhibitors; ACE/NEP inhibitors, such as omapatrilat, sampatrilat and fasidotril; angiotensin II antagonists, such as candesartan, eprosartan, irbesartan, losartan, telmisartan and valsartan, in particular valsartan; β-adrenergic receptor blockers, such as acebutolol, atenolol, betaxolol, bisoprolol, metoprolol, nadolol, propranolol, sotalol and timolol; inotropic agents, such as digoxin, dobutamine and milrinone; calcium channel blockers, such as amlodipine, bepridil, diltiazem, felodipine, nicardipine, nimodipine, nifedipine, nisoldipine and verapamil; and 3-hydroxy-3-methyl-glutaryl coenzyme A reductase (HMG-CoA) inhibitors, such as lovastatin, pitavastatin, simvastatin, pravastatin, cerivastatin, mevastatin, velostatin, fluvastatin, dalvastatin, atorvastatin, rosuvastatin and rivastatin. A compound of the present invention may be administered either simultaneously, before or after the other active ingredient, either separately by the same or different route of administration or together in the same pharmaceutical formulation.

A unit dosage for a mammal of about 50-70 kg may contain between about 1 and 1000 mg, advantageously between about 5-500 mg of the active ingredient. The therapeutically effective dosage of a compound of formula I is dependent on the species of warm-blooded animal (mammal), the body weight, age and individual condition, on the form of administration and on the compound involved.

The compounds of the present invention are inhibitors of aldosterone synthase, and thus may be employed for the treatment of conditions associated with aldosterone synthase activity, as described herein, e.g., hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction.

Thus, in an additional embodiment, the present invention relates to;

A compound of the invention for use as a medicament.

The use of a compound of the invention for the preparation of a pharmaceutical composition for the prevention and/or treatment of conditions associated with aldosterone synthase activity.

A method for the prevention and/or treatment of conditions associated with aldosterone synthase activity, which comprises administering a therapeutically effective amount of a compound of the invention.

In accordance with the foregoing the present invention provides in a yet further aspect:

A therapeutic combination, e.g. a kit, kit of parts e.g. for use in any method as defined herein, comprising a compound of formula I, in free form or in pharmaceutically acceptable salt form, to be used concomitantly or in sequence with at least one pharmaceutical composition comprising an anti-obesity agent, anti-hypertensive agent, inotropic agent or hypolipidemic agent. The kit may comprise instructions for its administration.

A kit of parts comprising (i) a pharmaceutical composition of the invention, (ii) a pharmaceutical composition comprising a compound selected from an anti-obesity agent, anti-hypertensive agent, inotropic agent or hypolipidemic agent, or a pharmaceutically acceptable salt thereof, in the form of two separate units of the components (i) to (ii).

A method as defined above comprising co-administration, e.g. concomitantly or in sequence, of a therapeutically effective amount of a compound of formula I in free form or in pharmaceutically acceptable salt form, and a second drug substance, said second drug substance being an anti-obesity agent, anti-hypertensive agent, inotropic agent or hypolipidemic agent, e.g. as indicated above.

Preferably the compound of the invention is administered to a mammal in need thereof.

Preferably the compound of the invention is used for the treatment of a disease which responds to an inhibition of aldosterone synthase.

Preferably the conditions associated with aldosterone synthase activity are selected from hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction.

A method or use according to the invention which comprises administering said compound in combination with a therapeutically effective amount of anti-obesity agent, anti-hypertensive agent, inotropic agent or hypolipidemic agent.

A method or use according to the invention which comprises administering said compound in the form of a pharmaceutical composition as described herein.

As used throughout the specification and in the claims, the term "treatment" embraces all the different forms or modes of treatment as known to those of the pertinent art and in particular includes preventive, curative, delay of progression and palliative treatment.

The above-cited properties are demonstrable in vitro and in vivo tests using advantageously mammals, e.g., mice, rats, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1 and 500 mg/kg, preferably between about 1 and 100 mg/kg.

The activity of a compound according to the invention can be assessed by the following methods or methods well-described in the art:

The aldosterone synthase inhibitory activity in vitro may be determined as follows:

Adult male Sprague-Dawley rats weighing 125-150 g are obtained from Harlan Farms. All animals are caged in pairs and maintained under standard conditions of light and temperature. The animals are placed on a sodium depleted diet (0.01-0.02%) from Harland Teklad, Madison Wis. (cat# TD90228) and maintained on normal drinking water ad libitum. The animals are maintained on this diet for two to four weeks prior to harvesting the adrenal glomerulosa cells. The rats are killed by $CO_2$ inhalation, and the adrenals are immediately removed and placed in the same ice-cold buffer used during homogenization and assay of the enzyme preparation. The adrenals are decapsulated to obtain the glomerulosa tissue. The tissue is homogenized in a glass homogenizer containing Tris assay buffer (8.5 mM $MgCl_2$, 2.7 mM $CaCl_2$, 3.13 mM KCl, 7.59 mM NaCl, 0.1% TEA and 50 mM Tris HCl adjusted to pH 7.4). The homogenate is diluted so that 37.5 mg of glomerulosa tissue is in each mL of buffer. The homogenate is centrifuged at 4° C. at 900×g for 10 min. To start the assay, and 200 µL aliquots (450-550 µg of protein) of the adrenal cytoplasmic preparation is added to each glass tube containing $2.5 \times 10^{-4}$ M NADPH, $4 \times 10^{-6}$ M corticosterone. The final corticosterone concentration consisted of $4 \times 10^{-6}$ M corticosterone (C-2505, Sigma Chemical Co, St. Louis, Mo.) and $1 \times 10^{-8}$ M [1,2,6,7-$^3$H] corticosterone (70 Ci/mM; NET 399; NEN™ Life Sciences Product, Inc., Boston, Mass.) and various concentrations of the putative aldosterone synthase inhibitor as indicated. The final volume of the incubation mixture is 0.5 mL. The mixture is incubated for 1 h at 25° C. in a Dubnoff shaking incubator at 1 atm of 95% $O_2$/5% $CO_2$. The reaction is stopped by the addition of 7 mL EtOAc, and the steroids extracted after vortexing. The water phase is extracted again with 3 mL of EtOAc. The combined extracts are dried under nitrogen, reconstituted in EtOAc, and spotted on silica gel TLC plates (LK6F; cat. # 4866-820; Whatman, Inc. Clifton, N.J.). The chromatograms are developed in a solvent system of toluene:acetone:water (120:80:0.8 v/v) for 60 min. The plates are scanned for radioactivity with a Bioscan System 200 Imaging Scanner (Bioscan, Ish. DC). The two products of the aldosterone synthase, 18-OH-corticosterone and aldosterone are scraped and counted in a liquid scintillation counter (Beckman LS6000TA, Beckman Instr., Palo Alto, Calif.).

The $IC_{50}$s are determined from a logit-log plot (pseudo-Hill plot) according to the equation (see Pratt and Taylor, Eds, "*Principles of Drug Action*", Churchill Livingstone Inc, NY (1990)):

$$\log P/(100-P) = n \log[I] + n \log IC_{50}$$

where P is the percent competition of specific binding in the presence of a given concentration of inhibitor (I). The slope (Hill Coefficient) and x intercept ($IC_{50}$) are determined by linear regression of the experimental data. The Km(app) is calculated by a computer program according to the Hanes equation (see Cornish-Bowden, Ed., "*Principles of Enzyme Kinetics*", Butterworth & Co., Boston, Mass. (1976)):

$$s/v = Km/V + s/V$$

where Km=Michaelis constant, V=maximum velocity, s=substrate concentration, v=velocity.

The aromatase inhibitory activity in vitro may be determined as follows:

Human placental microsome fraction is prepared from freshly delivered human term placenta as previously described with minor modifications (see Steele et al., *Steroids*, Vol. 50, pp. 147-161 (1987)). The tissue is freed of membranes and large vessels and rinsed repeatedly with 0.15 M KCl (4° C.). It is then minced in 0.25 M sucrose and homogenized. The homogenate is centrifuged at 20,000×g for 30 min. The supernatant is then centrifuged at 148,000×g for 60 min. The microsomal pellet obtained is re-suspended in 0.05 M potassium phosphate buffer pH 7.4 and centrifuged again at 148,000×g for 60 min. The resulting pellet is re-suspended in phosphate buffer, divided into aliquots, and stored at −40° C.

Human placental aromatase assay is performed in a incubation mixture consisting of: 12.5 mM phosphate buffer (12.5 mM $KH_2PO_4$, 1 mM EDTA, 1.6 mM dithiothreitol and 1.0 g/L of albumin; pH 7.5), NADPH ($2.4 \times 10^{-4}$ M), $1\beta$-$^3$H androstenedione ($1 \times 10^{-7}$ M) and the appropriate concentration of the desired inhibitor. The assay is started by pipetting the appropriate amount 50-500 μg of the human placental microsome preparation into the incubation mixture. The mixture is incubated at 37° C. for 20 min and stopped by addition of 6 volumes of chloroform. The samples are immediately vortexed and centrifuged. The aqueous layer is carefully removed so as to avoid contamination with chloroform. The aqueous fraction is treated with an equal volume of a 5% aqueous suspension of charcoal to remove any substrate not extracted by the chloroform. After centrifugation an aliquot of the aqueous phase is counted in a liquid scintillation counter. The enzymatic activity for each concentration of inhibitor is calculated as a percent of the vehicle control, which is arbitrarily set at 100%. Therefore, the relative enzyme inhibition is expressed as a percentage: 100% minus % enzyme activity with inhibitor present.

The aldosterone synthase inhibitory activity for reduction of cardiac damage in vivo may be evaluated as follows:

The protocol is nearly identical to that previously described (see Rocha et al., *Endocinology*, Vol. 141, pp. 3871-3878 (2000)) with minor modifications. The rats are housed in individual cages and given 0.9% NaCl as drinking fluid ad libitum throughout the experiment. Three days later rats are placed on one of the three dosing protocols. Group 1 (control) receives L-NAME for 14 days, and on day 11 of L-NAME treatment, an osmotic mini-pump containing only saline is implanted in each animal subcutaneously (s.c.). Group 2 (/L-NAME/Ang II) received L-NAME for 14 days, and on day 11 of L-NAME treatment, an osmotic mini-pump containing Ang II is implanted in each animal s.c. Group 3 (L-NAME/Ang II/test compound) is treated similarly to Group 2 but receives test compound (4 mg/kg/day) orally once a day. The test compound is dissolved in distilled water and given by gavage; whereas Groups 1 and 2 receive the vehicle. The experiment is concluded on day 14 of L-NAME treatment. The L-NAME (Sigma Chemical Co., St. Louis, Mo.) is administered in the 0.9% NaCl drinking water at a concentration of 60 mg/100 mL which results in a daily intake of approximately 60 mg/kg. Ang II is administered via Alzet osmotic mini-pumps (Model 2001; Alza Corp, Palo Alto, Calif.). The mini-pump is implanted s.c. at the nape of the neck. Ang II (human, 99% peptide purity) is purchased from Sigma Chemical Co., St. Louis, Mo. and administered at a dose of 225 μg/kg/day in saline. The concentration of Ang II used to fill the pumps is calculated based upon: (a) the mean pump rate provided by the manufacturer; (b) the body weight of the animals on the day before implantation of the pumps; and (c) dose planned. The rats are sacrificed on day 14. Their hearts are removed and sliced through the ventricle/atrium in a "bread-loaf" manner, yielding three samples from the following gross cardiac regions: superior, middle and inferior. The samples are fixed in 10% buffered formalin. Paraffin sections are cut and stained with hematoxylin/eosin. A single investigator who is blinded to the experimental groups views slides. One slide from each of three gross cardiac sample regions is analyzed per rat. Cardiac sites (left and right ventricles and the septum) are evaluated separately. The entire section is assessed histologically for the presence of myocardial damage (regardless of the severity) as evidenced by the presence of myocyte necrosis, inflammatory cells, hemorrhage and general tissue disruption. Evaluation of the histological data is made by comparing Groups 2 and 3, i.e., ANG II with or without test compound.

Illustrative of the invention, the compounds of Examples 1, 3 and 32 inhibit the aldosterone synthase activity with an $IC_{50}$ value of about 12 nM, 4 nM and 9 nM, respectively.

The following Examples are intended to illustrate the invention and are not to be construed as being limitations thereon. If not mentioned otherwise, all evaporations are performed under reduced pressure, preferably between about 10 and 100 mmHg (=20-133 mbar). The structure of final products, intermediates and starting materials is confirmed by standard analytical methods, e.g., microanalysis, melting point (m.p.) and spectroscopic characteristics, e.g., MS, IR, NMR. Abbreviations used are those conventional in the art. The concentration for $[\alpha]_D$ determinations is expressed in mg/mL.

EXAMPLE 1

4-(7-Cyclopropylmethyl-6-oxo-5,6,7,8-tetrahydro-imidazo[1,5-a]pyrazin-5-yl)-benzonitrile

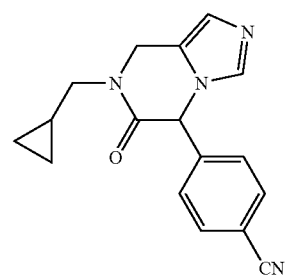

A. 1-Trityl-4-hydroxymethyl-1H-imidazole

To a stirred solution of 4(5)-hydroxymethylimidazole (15.7 g, 117 mmol) in DMF (200 mL) is added TEA (40.0 mL, 287 mmol) followed by trityl chloride (34.3 g, 123 mmol). The reaction mixture is stirred at RT for 8 h before it is poured into water. The collected solid is washed successively with water and diethyl ether and dried under reduced pressure. The solid is then re-crystallized from 1,4-dioxane to yield 1-trityl- 4-hydroxymethyl-1H-imidazole: m.p. 228-230° C.; ¹H-NMR (DMSO-d₆) δ 7.37 (9H, m), 7.35 (1H, s), 7.09 (6H, m), 6.78 (1H, s), 4.90 (1H, br s), 4.34 (2H, s); e/z (ES) 341 (M+1, 5%), 243 (100%).

B. 4-Acetoxymethyl-1-trityl-1H-imidazole

To a suspension of the title A compound 1-trityl-4-hydroxymethyl-1H-imidazole (34.5 g, 101 mmol) in pyridine (200 mL) is added acetic anhydride (28.6 mL, 303 mmol) in a dropwise fashion and the reaction is stirred until it becomes clear. The reaction mixture is poured into EtOAc and then washed with 0.5N aqueous HCl, saturated aqueous sodium bicarbonate and brine. The combined organic phases are dried over anhydrous sodium sulfate and then filtered through a silica pad yielding a solid after removal of the solvent in vacuo. The solid is triturated with diethyl ether to give 4-acetoxymethyl-1-tritylimidazole: m.p. 133-134° C.; ¹H-NMR (DMSO-d₆) δ 7.42 (10H, m), 7.09 (6H, m), 6.99 (1H, s), 4.89 (2H, s), 1.99 (3H, s); e/z (ES) 383 (M+1, 5%), 243 (100%).

C. 4-(5-Acetoxymethyl-imidazoyl-1-ylmethyl)-benzonitrile hydrobromide

The title B compound 4-acetoxymethyl-1-tritylimidazole (35.4 g, 92.7 mmol) and 4-cyanobenzylbromide (18.3 g, 93.3 mmol) are combined in EtOAc and heated at reflux for 16 h, the precipitated solid is filtered off, and washed thoroughly with EtOAc. The combined filtrate is eveporated to 30 mL and heated at reflux for 1 h and the precipitate again filtered off and washed with EtOAc. This is repeated by heating the EtOAc (10 mL) for 1 h and filtering. The combined solids are dissolved in methanol and heated at reflux for 1 h before evaporating the solvent in vacuo. The residue is triturated with diethyl ether to yield 4-(5-acetoxymethyl-imidazoyl-1-ylmethyl)-benzonitrile hydrobromide: ¹H-NMR (DMSO-dB) δ 9.38 (1H, s), 7.92 (2H, d, J=8.4), 7.90 (1H, s), 7.48 (2H, d, J=8.4), 6.99 (1H, s), 5.67 (2H, s), 5.10 (s, 2H), 1.75 (3H, s).

D. 4-(5-Hydroxymethyl-imidazoyl-1-ylmethyl)-benzonitrile

To the title C compound 4-(5-acetoxymethyl-imidazoyl-1-ylmethyl)-benzonitrile hydrobromide (28.9 g, 86.0 mmol) in THF:water (3:1, 400 mL) at 0° C. is added lithium hydroxide (10.8 g, 258 mmol) and the reaction warmed over 3 h and subsequently stirred at RT for 12 h. The reaction volume is reduced in vacuo and the residue is partitioned between EtOAc and saturated aqueous sodium bicarbonate. After washing with brine the combined organic phases are dried over anhydrous sodium sulfate and concentrated in vacuo to yield a solid which is triturated with diethyl ether to give 4-(5-hydroxymethyl-imidazoyl-1-ylmethyl)-benzonitrile: m.p. 162-164° C.; ¹H-NMR (DMSO-d₆) δ 7.83 (2H, d, J=8.3), 7.73 (1H, s), 7.30 (2H, d, J=8.3), 6.87(1H, s), 5.35 (2H, s), 5.15 (2H, t, J=5.3), 4.30 (2H, d, J=5.3); e/z (ES) 214 (M+1, 100%).

E. 4-(5-t-Butyl-dimethylsilanyloxymethyl-imidazoyl-1-ylmethyl)-benzonitrile

To a solution of the title D compound 4-(5-hydroxymethyl-imidazoyl-1-ylmethyl)-benzonitrile (13.6 g, 63.8 mmol) in DMF (30 mL) is added imidazole (6.8 g, 100 mmol) followed by TBDMSICI (10.0 g, 66.3 mmol). The reaction mixture is stirred at RT for 2 h, then partitioned between EtOAc and saturated aqueous sodium bicarbonate. The organic solution is dried over anhydrous sodium sulfate and removal of the solvent in vacuo yields a solid which is subjected to flash chromatography (silica gel) eluting with EtOAc to give 4-(5-t-butyl-dimethylsilanyloxymethyl-imidazoyl-1-ylmethyl)-benzonitrile: m.p. 77-79° C.; ¹H-NMR (DMSO-d₆) δ7.89 (2H, d, J=8.2), 7.83 (1H, s), 7.31 (2H, d, J=8.2), 6.98 (1H, s), 5.42 (2H, s), 4.59 (2H, s), 0.82 (9H, s), 0.00 (6H, s); ¹³C-NMR (DMSO-d₆) δ 164.6, 143.7, 139.5, 132.9, 130.8, 128.4, 127.8, 119.0, 110.6, 54.9, 47.5, 26.0, 18.1, −5.2; e/z (ES) 328 (M+1, 100%).

F. Methyl [5-(t-butyl-dimethylsilanyloxymethyl)-imidazol-1-yl]-(4-cyano-phenyl)-acetate To a solution of the title E compound 4-(5-t-butyl-dimethylsilanyloxymethyl-imidazoyl-1-ylmethyl)-benzonitrile (10.4 g, 31.8 mmol) in THF (100 mL) at −78° C. is added dropwise 1.0 M LHMDS (67.0 mL, 67.0 mmol) and stirred for 10 min. Methyl cyanoformate (2.55 mL, 31.8 mmol) is added and the solution stirred for 10 min before quenching the reaction with acetic acid. On warming the reaction mixture is partioned between ammonium chloride and EtOAc, thereafter the combined organic phases are dried over anhydrous sodium sulfate and removal of the solvent in vacuo yields a viscous oil. The crude reaction mixture is subjected to flash chromatography (silica gel) eluting with EtOAc:MeOH:NH₄OH (90:10:0.1) to give the desired material which is re-crystallized from diethyl ether:hexane to give methyl [5-(t-butyl-dimethylsilanyloxymethyl)-imidazol-1-yl]-(4-cyano-phenyl)-acetate as a solid: m.p. 83-84° C.; ¹H-NMR (CDCl₃) δ 7.66 (2H, d, J=8.3), 7.60 (1H, s), 7.35 (2H, d, J=8.3), 6.92 (1H, s), 4.63 (1H, d, 13.4), 4.56 (1H, d, J=13.4), 3.81 (3H, s), 0.81 (9H, s), 0.00 (3H, s), −0.01 (3H, s); ¹³C-NMR (CDCl₃) δ 168.0, 164.4, 139.4, 137.6, 132.6, 130.2, 128.0, 127.5, 117.6, 112.9, 60.3, 54.9, 53.0, 25.4, 17.8, −5.7, −5.8; e/z (ES) 386 (M+1, 100%); calculated for C₂₀H₂₇N₃O₃Si, C, 62.31; H, 7.06; N, 10.90. found C, 62.36; H, 6.92; N, 11.06.

G. Methyl 1-(4-cyano-phenyl)-(5-hydroxymethyl-imidazol-1-yl)-acetate

The title F compound methyl [5-(t-butyl-dimethylsilanyloxymethyl)-imidazol-1-yl]-(4-cyano-phenyl)-acetate (9.65 g, 25.06 mmol) and p-toluenesulfonic acid (6.0 g, 31.50 mmol) are stirred in MeOH (100 mL) at RT for 24 h. The reaction mixture is evaporated to an oil and partitioned between EtOAc and sodium bicarbonate. The combined organic phases are dried over anhydrous sodium sulfate and concentrated in vacuo to yield a solid, which is triturated with diethyl ether to give methyl 1-(4-cyano-phenyl)-(5-hydroxymethyl-imidazol-1-yl)-acetate: ¹H-NMR (DMSO-d₆) δ 7.92 (2H, d, J=8.3), 7.62 (2H, d, J=8.3), 7.61 (1H, s), 6.83 (1H, s), 6.48 (1H, s), 5.26 (1H, t, J=5.3), 4.47 (2H, d, J=5.3), 3.75 (3H, s); ¹³C-NMR (DMSO-d₆) δ 168.9, 164.4, 140.6, 137.9, 133.3, 132.1, 129.6, 127.0, 118.6, 112.1, 60.3, 53.5, 53.0; e/z (ES) 272 (M+1, 100%).

H. Methyl 1-(4-cyano-phenyl)-(5-formyl-imidazol-1-yl)-acetate

To a solution of the title G compound methyl 1-(4-cyano-phenyl)-(5-hydroxymethyl-imidazol-1-yl)-acetate (5.60 g, 20.7 mmol) in DCM (100 mL) is added Dess-Martin periodinane (15% wt solution, 65 mL, 30 mmol) and the reaction is stirred for 3 h. The reaction mixture is partitioned between EtOAc and sodium bicarbonate-sodium thiosulfate. The combined organic phases are washed with brine and dried (anhydrous sodium sulfate) and evaporated to a solid. Re-crystallization from EtOAc:hexane gives methyl 1-(4-cyanophenyl)-(5-formyl-imidazol-1-yl)-acetate: m.p. 148-150° C.; $^1$H-NMR (CDCl$_3$) δ 9.75 (1H, s), 7.88 (1H, s), 7.78 (2H, d, J=8.3), 7.73 (1H, s), 7.51 (2H, d, J=8.3), 6.95 (1H, s), 3.84 (3H, s); $^{13}$C-NMR (CDCl$_3$) δ 180.0, 168.4, 165.0, 144.5, 143.3138.5, 133.6, 131.1, 129.6, 118.1, 114.3, 62.2, 53.9; e/z (ES) 270 (M+1, 100%); calculated for C$_{14}$H$_{11}$N$_3$O$_3$, C, 62.45; H 4.12; N, 15.61. found C, 62.13; H, 4.20; N, 15.33.

I. 4-(7-Cyclopropylmethyl-6-oxo-5,6,7,8-tetrahydro-imidazo[1,5-a]pyrazin-5-yl)-benzonitrile To a solution of the title H compound methyl 1-(4-cyanophenyl)-(5-formyl-imidazol-1-yl)-acetate (0.135 g, 0.50 mmol) in DCE (4 mL) is added cyclopropylmethylamine (0.060 mL, 0.70 mmol) followed by sodium triacetoxyborohydride (0.300 g, 1.41 mmol). The reaction mixture is stirred at RT for 16 h. The reaction is partitioned between EtOAc and saturated aqueous sodium bicarbonate and the organic solution is washed with brine before drying (anhydrous sodium sulfate). The solid obtained after removal of the solvent in vacuo is re-crystallized from acetone:diethyl ether to yield 4-(7-cyclopropylmethyl-6-oxo-5,6,7,8tetrahydro-imidazo [1,5-a]pyrazin-5-yl)-benzonitrile: m.p. 146-147° C.; $^1$H-NMR (CDCl$_3$) 7.64 (2H, d, J=8.3), 7.40 (1H, s), 7.07 (2H, d, J=8.3), 6.74 (1H, s), 6.07 (1H, s), 4.57 (1H, d, J=16.1), 4.43 (1H, d, J=16.1), 3.14 (1H, dd, J=13.8, 10.0), 3.03(1H, dd, J=13.8, 7.2), 0.75 (1H, m), 0.19 (2H, m), 0.00 (2H, m); $^{13}$C-NMR (CDCl$_3$) δ 164.2, 142.7, 135.2, 133.2, 127.7, 123.4, 122.9, 118.7, 111.7, 60.1, 51.0, 42.1, 9.2, 3.6, 3.3; e/z (ES) 293 (M+1, 100%); calculated for C$_{17}$H$_{16}$N$_4$O 0.15H$_2$O, C, 69.21; H, 5.57; N, 18.99. found C, 69.10; H, 5.50; N, 19.27.

EXAMPLE 2

4-(7-Methyl-6-oxo-5,6,7,8-tetrahydro-imidazo[1,5-a]pyrazin-5-yl)-benzonitrile hydrochloride

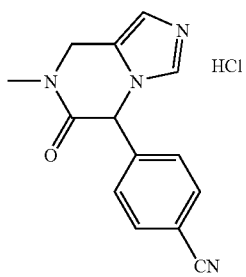

The title compound is prepared analogously to Example 1, i.e., 4-(7-methyl-6-oxo-5,6,7,8-tetrahydro-imidazol[1,5-a]pyrazin-5-yl)-benzonitrile, obtained analogously to Example 1, is dissolved in acetone, then treated with Et$_2$O—HCl(g) to afford the hydrochloride salt: m.p. 222-224° C.; $^1$H-NMR (DMSO-d$_6$) 9.07 (1H, s), 7.92 (2H, d, J=8.2), 7.48 (1H, s), 7.49 (2H, d, J=8.2), 6.46 (1H, s), 4.83 (2H, s), 3.03 (3H, s); $^{13}$C-NMR (DMSO-d$_6$) δ 162.5, 140.5, 134.3, 133.4, 128.7, 125.1, 118.6, 115.7, 112.4, 60.9, 43.1, 34.9; e/z (ES) 253 (M+1, 100%); calculated for C$_{14}$H$_{12}$N$_4$O HCl 0.4H$_2$O, C, 56.82; H, 4.70; N, 18.93. found C, 56.88; H, 4.54; N, 18.89.

EXAMPLE 3

4-(7-Benzyl-6-oxo-5,6,7,8-tetrahydro-imidazo[1,5-a]pyrazin-5-yl)-benzonitrile

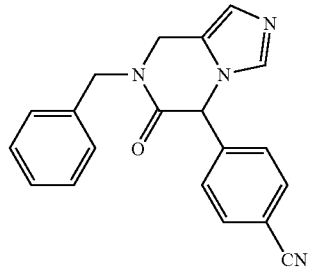

The title compound is prepared analogously to Example 1: m.p. 163-165° C.; $^1$H-NMR (DMSO-d$_6$) δ 7.89 (2H, d, J=8.3), 7.63 (1H, s), 7.29 (5H, m), 7.18 (2H, m), 6.93 (1H, s), 4.73 (1H, d, J=14.9), 4.63 (1H, d, J=16.1), 4.56 (1H, d, J=14.9), 4.53 (1H, d, J=16.1); $^{13}$C-NMR (DMSO-d$_6$) δ 164.5, 142.6, 136.5, 135.3, 133.3, 129.0, 128.0, 127.9, 127.7, 123.5, 122.6, 118.7, 111.7, 60.2, 50.0, 41.9; e/z (ES) 329 (M+1, 100%); calculated for C$_{20}$H$_{16}$N$_4$O, C, 73.15; H, 4.91; N, 17.06. found C, 72.83; H, 4.71; N, 17.07.

EXAMPLE 4

4-(7-Allyl-6-oxo-5,6,7,8-tetrahydro-imidazo[1,5-a]pyrazin-5-yl)-benzonitrile

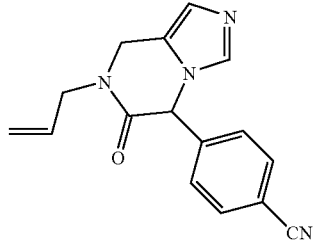

The title compound is prepared analogously to Example 1: m.p. 107-109° C.; $^1$H-NMR (DMSO-d$_6$) δ 7.88 (2H, d, J=8.3), 7.62 (1H, s), 7.30 (2 h, d, J=8.3), 6.97 (1H, s), 6.34 (1H, s), 5.73 (1H, m), 5.15 (1H, dd, J=10.3, 1.4), 5.09 (1H, dd, J=17.1, 1.4), 4.62 (1H, d, J=16.1), 4.58 (1H, d, J=16.1), 4.12 (1H, dd, J=15.4, 6.4), 3.99 (1H, dd, J=15.4, 5.8); $^{13}$C-NMR (DMSO-d$_6$) δ 164.1, 142.6, 135.3, 133.3, 132.3, 127.7, 123.4, 122.7, 118.1, 111.7, 60.1, 49.1, 41.7; e/z (ES) 279 (M+1, 100%); calculated for C$_{16}$H$_{14}$N$_4$O, C, 69.05; H, 5.07; N, 20.13. found C, 68.84; H, 5.05; N, 20.07.

EXAMPLE 5

4-(6-Oxo-7-propyl-5,6,7,8-tetrahydro-imidazo[1,5-a]pyrazin-5-yl)-benzonitrile

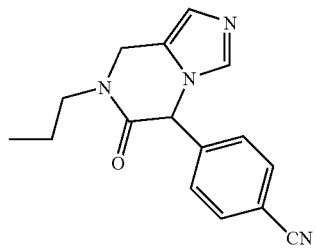

The title compound is prepared analogously to Example 1: m.p. 97-98° C.; $^1$H-NMR (DMSO-d$_6$) δ 7.87 (2H, d, J=8.3), 7.63 (1H, s), 7.28 (2H, d, J=8.3), 6.96 (1H, s), 6.29 (1H, s), 4.69 (1H, d, J=16.1), 4.59 (1H, d, J=16.1), 3.36 (2H, m), 1.48 (2H, m), 0.75 (3H, t, J=7.4); $^{13}$C-NMR (DMSO-d$_6$) δ 164.2, 142.7, 135.3, 133.3, 132.3, 127.6, 123.3, 122.9, 118.7, 111.6, 60.1, 48.5, 41.9, 20.0, 11.2; e/z (ES) 281 (M+1, 100%); calculated for C$_{16}$H$_{16}$N$_4$O, C, 68.55; H, 5.75; N, 19.99. found C, 68.30; H, 5.72; N, 19.95.

EXAMPLE 6

4-(7-Isopropyl-6-oxo-5,6,7,8-tetrahydro-imidazo[1,5-a]pyrazin-5-yl)-benzonitrile

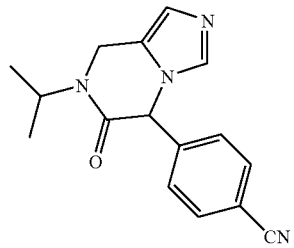

The title compound is prepared analogously to Example 1: m.p. 122-124° C.; $^1$H-NMR (DMSO-d$_6$) δ 7.87 (2H, d, J=8.3), 7.64 (1H, s), 7.28 (2H, d, J=8.3), 6.97 (1H, s), 6.28 (1H, s), 4.69 (1H, d, J=16.1), 4.65 (1H, m), 4.36 (1H, d, J=16.1), 1.12 (3H, d, J=6.8), 1.07 (3H, d, J=6.8); $^{13}$C-NMR (DMSO-d$_6$) δ 163.8, 142.5, 135.2, 133.3, 127.6, 123.4, 123.2, 118.7, 111.6, 60.3, 45.3, 35.7, 19.1, 19.0; e/z (ES) 281 (M+1, 100%); calculated for C$_{16}$H$_{16}$N$_4$O, C, 68.55; H, 5.75; N, 19.99. found C, 68.17; H, 5.73; N, 19.89.

EXAMPLE 7

4-7-[2-(4-Fluoro-phenyl)-ethyl]-6-oxo-5,6,7,8-tetrahydro-imidazo[1,5-a]pyrazin-5-yl)-benzonitrile hydrochloride

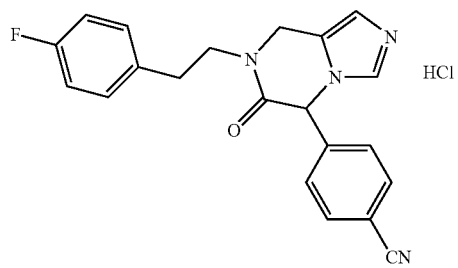

The title compound is prepared analogously to Example 2: m.p. 160-162° C.; $^1$H-NMR (DMSO-d$_6$) δ9.12 (1H, s), 7.88 (2H, d, J=8.2), 7.74 (1H, s), 7.33 (2H, d, J=8.2), 7.16 (2H, m), 6.98 (2H, m), 6.47 (1H, s), 4.82 (1H, d, J=16.5), 4.61 (1H, d, J=16.5), 3.87 (1H, m), 3.55 (1H, m), 2.82 (2H, m); $^{13}$C-NMR (DMSO-d$_6$) δ 162.5, 161.2 (d, J=, 242.2), 139.9, 134.5 (d, J=3.0), 134.4, 133.3, 130.8 (d, J=8.3), 128.2, 125.2, 118.6, 115.8, 115.3 (d, J=21.1), 112.3, 61.1, 48.3, 41.4, 31.7; e/z (ES) 361 (M+1, 100%); calculated for C$_{21}$H$_{17}$N$_4$OF HCl 0.1 H$_2$O, C, 63.27; H, 4.35; N, 14.05. found C, 63.04; H, 4.46; N, 14.02.

EXAMPLE 8

4-(7-(3-Morpholin-4-yl-propyl-6-oxo-5,6,7,8-tetrahydro-imidazo[1,5-a]pyrazin-5-yl)-benzonitrile dihydrochloride

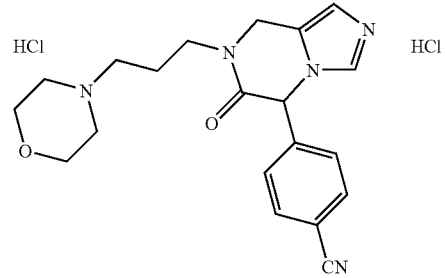

The title compound is prepared analogously to Example 2: m.p. 246-248° C.; $^1$H-NMR (DMSO-d$_6$) δ 9.13 (1H, s), 7.93 (2H, d, J=8.3), 7.78 (1H, s), 7.55 (2H, d, J=8.3), 6.53 (1H, s), 4.91 (2H, s), 3.85 (4H, m), 3.57 (2H, m), 3.33 (2H, m), 3.00 (4H, m), 2.06 (2H, m); $^{13}$C-NMR (DMSO-d$_6$) δ 163.1, 140.2, 134.3, 133.5, 129.0, 125.2, 118.6, 115.7, 112.4, 63.4, 61.0, 53.4, 51.2, 51.1, 44.4, 41.3, 21.0; e/z (ES) 366 (M+1, 100%); calculated for C$_{20}$H$_{23}$N$_5$O$_2$ 2 HCl 0.2H$_2$O, C, 54.35; H, 5.34; N, 15.85. found C, 54.25; H, 5.68; N, 15.84.

EXAMPLE 9

4-[7-(4-Methoxy-benzyl)-6-oxo-5,6,7,8-tetrahydro-imidazo[1,5-a]pyrazin-5-yl)-benzonitrile

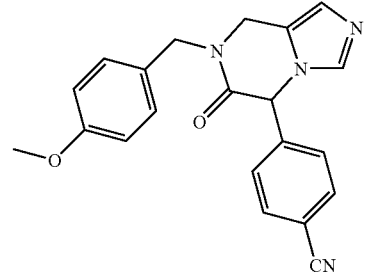

The title compound is prepared analogously to Example 1: m.p. 155-157° C.; $^1$H-NMR (DMSO-d$_6$) δ 7.88 (2H, d, J=8.3), 7.62 (1H, s), 7.29 (2H, d, J=8.3), 7.14 (2H, d, J=8.6), 6.92 (1H, s), 6.87 (2H, d, J=8.6), 6.39 (1H, s), 4.55 (4H, m) 3.72 (3H, s); $^{13}$C-NMR (DMSO-d$_6$) δ 164.3, 159.1, 142.6, 135.3, 133.3, 129.6, 128.4, 128.0, 127.7, 123.5, 122.6, 118.7, 114.4, 111.7, 65.3, 60.1, 55.4, 49.3, 41.5; e/z (ES) 359 (M+1, 100%); calculated for C$_{21}$H$_{18}$N$_4$O$_2$, C, 70.38; H, 5.06; N, 15.63. found C, 69.98; H, 5.15; N, 15.50.

EXAMPLE 10

4-[7-(4-Methyl-benzyl)-6-oxo-5,6,7,8-tetrahydro-imidazo[1,5-a]pyrazin-5-yl)-benzonitrile

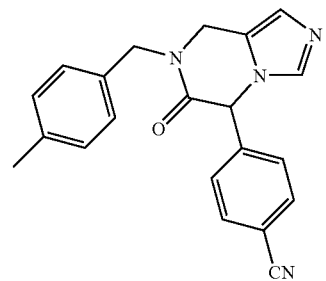

The title compound is prepared analogously to Example 1: m.p. 168-170° C.; $^1$H-NMR (DMSO-d$_6$) δ 7.88 (2H, d, 8.3), 7.62 (1H, s), 7.29 (2H, d, J=8.3), 7.11 (2H, d, J=8.2), 7.07 (2H, d, J=8.2), 6.92 (1H, s), 6.40 (1H, s), 4.67 (1H, d, J=14.7), 4.59 (1H, d, J=16.2), 4.51 (1H, d, J=14.7), 4.49 (1H, d, J=16.2), 2.26 (3H, s); $^{13}$C-NMR (DMSO-d$_6$) δ 164.4, 142.6, 137.2, 135.3, 133.5, 133.3, 129.6, 128.1, 127.7, 123.5, 122.6, 118.7, 111.7, 60.1, 49.6, 41.7, 21.0; e/z (ES) 343 (M+1, 100%); calculated for C$_{21}$H$_{18}$N$_4$O, C, 73.67; H, 5.30; N, 16.36. found C, 73.54; H, 5.22; N, 16.46.

EXAMPLE 11

4-[7-(4-Chloro-benzyl)-6-oxo-5,6,7,8-tetrahydro-imidazo[1,5-a]pyrazin-5-yl]-benzonitrile hydrochloride

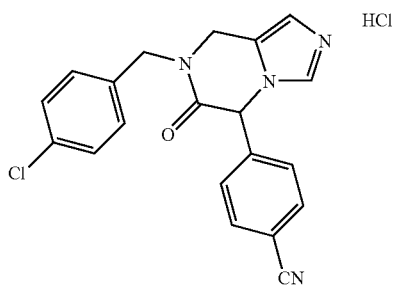

The title compound is prepared analogously to Example 2: m.p. 245-246° C.; $^1$H-NMR (DMSO-d$_6$) 9.13 (1H, s), 7.94 (2H, d, J=8.3), 7.70 (1H, s), 7.52 (2H, d, J=8.3), 7.41 (2H, d, J=8.4), 7.29 (2H, d, J=8.4), 6.59 (1H, s), 4.77 (1H, d, J=15.1), 4.74 (1H, d, 16.8), 4.72 (1H, d, J=16.8), 4.59 (1H, d, J=15.1); $^{13}$C-NMR (DMSO-d$_6$) δ 162.6, 139.6, 134.7, 134.0, 133.0, 132.2, 129.7, 128.5, 128.3, 124.6, 118.2, 115.4, 112.0, 60.7, 48.9, 40.8; e/z (ES) 363 (M+1, 100%); calculated for C$_{20}$H$_{15}$N$_4$OCl HCl, C, 60.16; H, 4.04; N, 14.03. found C, 60.17; H, 3.89; N, 14.08.

EXAMPLE 12

4-[6-Oxo-7-(4-trifluoromethyl-benzyl)-5,6,7,8-tetrahydro-imidazo[1,5-a]pyrazin-5-yl)-benzonitrile hydrochloride

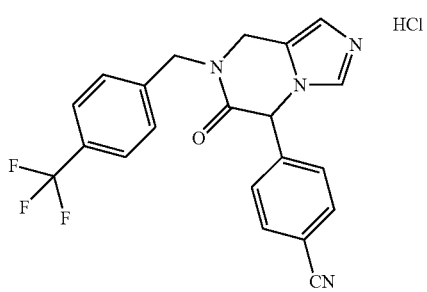

The title compound is prepared analogously to Example 2: m.p. 234-236° C.; $^1$H-NMR (DMSO-d$_6$) δ 9.16 (1H, s), 7.94 (2H, d, J=8.3), 7.72 (2H, d, J=8.0), 7.71 (1H, s), 7.55 (2H, d, J=8.3), 7.48 (2H, d, J=8.0), 6.63 (1H, s), 4.90 (1H, d, 15.5), 4.79 (2H, s), 4.70(1H, d, J=15.5); $^{13}$C-NMR (DMSO-d$_6$) δ 163.2, 141.1, 140.1, 134.2, 133.4, 128.8, 128.6 (q, J=31.7), 125.8 (t, J=3.8), 125.1, 118.6, 115.8, 112.5, 61.2, 49.7, 41.5; e/z (ES) 397 (M+1,100%); calculated for C$_{21}$H$_{15}$N$_4$OF$_3$ HCl, C, 58.27; H, 3.73; N, 12.94. found C, 58.06; H, 3.70; N, 12.93.

EXAMPLE 13

4-[6-Oxo-7-(3-methyl-benzyl)-5,6,7,8-tetrahydro-imidazo[1,5-a]pyrazin-5-yl)-benzonitrile hydrochloride

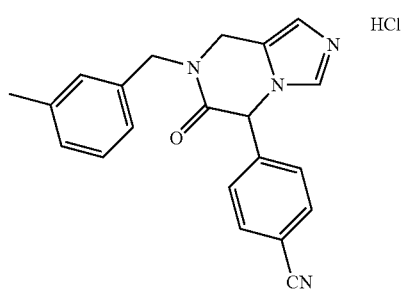

The title compound is prepared analogously to Example 2: m.p. 275-277° C.; $^1$H-NMR (DMSO-d$_6$) 9.14 (1H, s), 7.95 (2H, d, J=8.3), 7.70 (1H, s), 7.51 (2H, d, J=8.3), 7.23 (1H, d, J=7.6), 7.21 (1H, d, J=7.6), 7.10 (1H, d, J=7.6), 7.02 (1H, d, J=7.6), 6.97 (1H, s), 6.60 (1H, s), 4.69 (4H, m), 2.23 (3H, s); $^{13}$C (DMSO-d$_6$) 162.4, 139.7, 137.8, 135.5, 134.0, 133.0, 128.5, 128.2, 128.1, 124.8, 124.6, 118.1, 115.4, 112.0, 60.7, 49.3, 40.6, 20.8; e/z (ES) 343 (M+1, 100%); calculated for C$_{21}$H$_{18}$N$_4$O HCl, C, 66.57; H, 5.05; N, 14.67. found C, 66.38; H, 5.02; N, 14.84.

EXAMPLE 14

4-[6-Oxo-7-(4-fluoro-benzyl)-5,6,7,8-tetrahydro-imidazo[1,5-a]pyrazin-5-yl]-benzonitrile

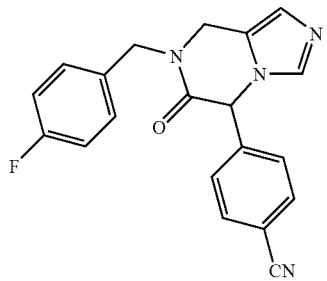

The title compound is prepared analogously to Example 1: m.p. 132-135° C.; $^1$H-NMR (DMSO-d$_6$) δ 7.88 (2H, d, J=8.2), 7.61 (1H, s), 7.27 (4H, m), 7.19 (2H, m,), 6.93 (1H, s), 6.39 (1H, s), 4.64 (4H, m); $^{13}$C-NMR (DMSO-d$_6$): δ 164.1, 161.5 (d, J=243.0), 142.1, 134.9, 132.9, 132.4 (d, J=3.0), 129.8 (d, J=8.3), 127.3, 123.0, 122.1, 118.3, 115.4 (d, J=21.1), 111.3, 59.7, 48.8, 41.4; e/z 347 (M+1, 100%); calculated C$_{20}$H$_{15}$FN$_4$O 0.1H$_2$O, C, 69.00; H, 4.40; N, 16.09. found C, 68.72; H, 4.35; N, 16.10.

EXAMPLE 15

4-[6-Oxo-7-(3-trifluoromethyl-benzyl)-5,6,7,8-tetrahydro-imidazo[1,5-a]pyrazin-5-yl)-benzonitrile hydrochloride

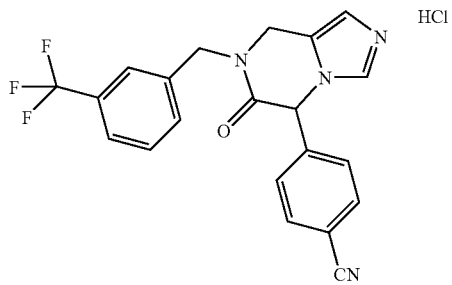

The title compound is prepared analogously to Example 2: m.p. 250-252° C.; $^1$H-NMR (MeOH-d$_4$) δ 9.01 (1H, s), 7.83 (2H, d, J=8.1), 7.65 (1H, s), 7.61 (1H, d, J=6.3), 7.54 (2H, m), 7.52 (1H, s), 7.49 (2H, d, J=8.1), 6.54 (1H, s), 4.93 (1H, d, J=15.0), 4.86 (1H, d, J=16.5), 4.78 (1H, d, J=15.0), 4.72 (1H, d, J=16.5); $^{13}$C-NMR (MeOH-d$_4$) δ 164.6, 140.2, 138.3, 135.6, 134.4, 133.0, 132.2 (q, J=31.9), 130.9, 129.2, 127.0, 126.0 (d, J=4.0), 125.8 (d, J=4.0), 125.4 (q, J=272.3), 118.8, 116.9, 114.8, 63.1, 51.3, 42.3; e/z (ES) 397 (M+1, 100%); calculated for C$_{21}$H$_{15}$F$_3$N$_4$O HCl, C, 58.27; H, 3.73; N, 12.94. found C, 57.91; H, 3.86; N, 12.74.

EXAMPLE 16

4-[6-Oxo-7-(3,4-dichloro-benzyl)-5,6,7,8-tetrahydro-imidazol-1,5-a]pyrazin-5-yl)-benzonitrile

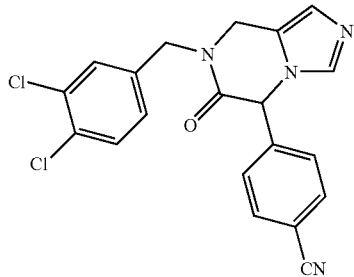

The title compound is prepared analogously to Example 1: m.p. 175-176° C.; $^1$H-NMR (DMSO-d$_6$) δ 7.89 (2H, d, J=8.0), 7.60 (2H, m), 7.34 (3H, m), 7.19 (2H, d, J=8.2), 6.94 (1H, s), 6.40 (1H, s), 4.64 (4H, m); $^{13}$C-NMR (DMSO-d$_6$) δ 164.3, 142.0, 137.5, 134.9, 132.9, 131.1, 130.7, 130.1, 129.5, 127.9, 127.3, 123.1, 122.0, 118.3, 114.5, 111.4, 59.7, 48.6, 41.9; e/z (ES) 397 (M+1, 100%); calculated for C$_{20}$H$_{14}$N$_4$OCl$_2$, C, 60.47; H, 3.55; N, 14.10. found C, 60.18; H, 3.64; N, 14.07.

EXAMPLE 17

The following compounds are prepared analogously to Example 1.

| Example | R | R' | e/z (M + 1) | m.p. (° C.) |
|---|---|---|---|---|
| 17-1 | cyclopropyl | 4-CN-phenyl | 279 | |
| 17-2 | cyclohexyl | 4-CN-phenyl | 321 | |
| 17-3 | cyclopentyl | 4-CN-phenyl | 307 | |
| 17-4 | 2-methoxyethyl | 4-CN-phenyl | 297 | |
| 17-5 | 3-methoxypropyl | 4-CN-phenyl | 311 | |
| 17-6 | 4-pyridylmethyl | 4-CN-phenyl | 330 | |
| 17-7 | 4-F-benzyl | 4-CF$_3$-phenyl | 390 | 257-258 |
| 17-8 | cyclopropylmethyl | 3-CF$_3$-phenyl | 336 | 240-242 |
| 17-9 | 4-F-benzyl | 4-MeO-phenyl | 352 | 205-206 |
| 17-10 | 4-F-benzyl | 2-MeO-phenyl | 351 | 134-135 |
| 17-11 | 4-F-benzyl | 2-Cl-phenyl | 356 | 160 |
| 17-12 | 4-F-benzyl | 1-naphthyl | 371 | |
| 17-13 | 4-F-benzyl | 2-naphthyl | 371 | |
| 17-14 | 4-F-benzyl | 2-thienyl | 327 | 95-97 |
| 17-15 | 4-F-benzyl | 3-thienyl | 327 | |

EXAMPLE 18

7-Benzyl-5-phenyl-7,8-dihydro-imidazo[1,5-a]pyrazin-6-one hydrochloride

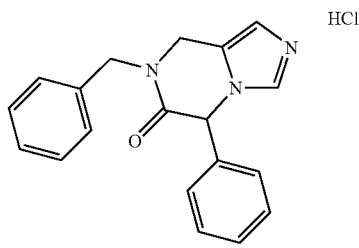

A. 4-(t-Butyidimethylsilanoxymethyl)-1-trityl-1H-imidazole

To a suspension of the title A compound in Example 1,1-trityl-4-hydroxymethyl-imidazole (21.8 g, 101 mmol) in DMF (200 mL) is added imidazole (13.1 g, 192.4 mmol), DMAP (0.20 g) followed by TBDMSICl (10.6 g, 70.3 mmol). The reaction mixture is stirred for 18 h at RT before being partitioned between EtOAc and saturated aqueous sodium bicarbonate. The combined organic phases are washed with brine, dried over anhydrous sodium sulfate and then filtered through a silica pad to yield 4-(t-butyldimethylsilanoxy-methyl)-1-trityl-1H-imidazole as a solid after removal of the solvent in vacua: m.p. 90-91° C.; $^1$H-NMR (CDCl$_3$) δ 7.29 (10H, m), 7.13 (6H, m), 6.70 (1H, s), 4.66 (2H, s), 0.82 (9H, s), 0.00 (6H, s); e/z (ES) 455 (M+1, 100%).

B. Methyl [5-hydroxymethyl)-imidazol-1-yl]-phenyl-acetate

Under a nitrogen atmosphere is mixed the title B compound, 4-(t-butyldimethyl-silanoxymethyl)-1-trityl-1H-imidazole (5.0 g, 11.0 mmol) and sodium sulfate (2.0 g, 14.0 mmol) in acetonitrile (20 mL) and stirred at RT. To this mixture is added a solution of methyl α-bromo-phenylacetate (2.53 g, 11.0 mmol) in acetonitrile (10 mL) and the reaction is stirred for 18 h. The mixture is vacuum filtered, treated with saturated HCl solution in MeOH (20 mL) and the mixture is stirred for 3 h. The solution is concentrated in vacuo and the residue taken up in water and washed with EtOAc. The aqueous solution is basified with saturated aqueous sodium bicarbonate and extracted into EtOAc. The combined extracts are washed with brine and dried (anhydrous sodium sulfate). The solvent is removed to yield methyl [5-hydroxymethyl]-imidazol-1-yl]-phenyl-acetate as a semi-solid: $^1$H-NMR (CDCl$_3$) δ 7.48-7.27 (6H, m), 6.83 (1H, s), 6.26 (1H, s), 4.59 (2H, s), 3.79 (3H, s); e/z (ES) 247 (M+1, 100%).

C. Methyl (5-formyl-imidazol-1-yl)-phenyl-acetate

The title B compound methyl [5-hydroxymethyl)-imidazol-1-yl]-phenyl-acetate (3.14 g, 12.8 mmol) in DCM (30 mL) is added to a solution of Dess-Martin periodinane (15% wt solution, 35 mL, 30 mmol) and the reaction stirred for 18 h. The reaction mixture is partitioned between EtOAc and sodium bicarbonate-sodium thiosulfate. The combined organic phases are washed with brine and dried (anhydrous sodium sulfate) and evaporated to an oil which is chromatographed (silica gel) eluting with hexane:EtOAc (1:1) to yield methyl (5-formyl-imidazol-1-yl)-phenyl-acetate as a solid: m.p. 106-109° C.; $^1$H-NMR (CDCl$_3$) δ 9.78 (1H, s), 7.86 (1H, s), 7.37-7.52 (6H, m), 6.71 (1H, s), 3.82 (3H's, s); e/z (ES) 245 (M+1, 100%).

D. 7-Benzyl-5-phenyl-7,8-dihydro-imidazo[1,5-a]pyrazin-6-one hydrochloride

To a solution of the title C compound, methyl 1-phenyl-(5-formyl-imidazol-1-yl)-acetate (0.45 g, 1.80 mmol) in 1,2-dichloroethane (15 mL) is added benzylamine (0.21 g, 2.0 mmol) followed by sodium triacetoxyborohydride (0.850 g, 4.00 mmol). The reaction mixture is stirred at 40° C. for 16 h. The reaction is partitioned between EtOAc and saturated aqueous sodium bicarbonate and the organic solution is washed with brine before drying (anhydrous sodium sulfate). The product obtained after removal of the solvent in vacuo is dissolved in acetone, treated with Et$_2$O—HCl(g) to yield 7-benzyl-5-phenyl-7,8-dihydro-imidazo[1,5-a]pyrazin-6-one hydrochloride: m.p. 249-251° C.; $^1$H (DMSO-d$_6$) 9.16 (1H, s), 7.68 (1H, s), 7.46 (3H, m), 7.30 (7H, m), 6.45 (1H, s), 4.78 (1H, d, J=15.0), 4.76 (1H, d, J=15.0), 4.65 (2H, d, J=15.0); $^{13}$C (DMSO-d$_6$) 163.7, 136.2, 134.3, 129.6, 129.5, 129.0, 128.1, 128.0, 127.2, 125.1, 115.7, 61.6, 49.9, 41.1; e/z (ES) 304 (M+1, 100%); calculated for C$_{19}$H$_{17}$N$_3$O HCl, C, 67.15; H, 5.34; N, 12.37. found C, 66.88; H, 5.29; N, 12.12.

EXAMPLE 19

7-Methyl-5-phenyl-7,8-dihydro-imidazo[1,5-a]pyrazin-6-one hydrochloride

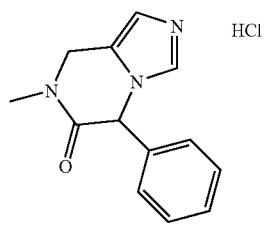

The title compound is prepared analogously to Example 18: m.p. 252-254° C.; $^1$H-NMR (DMSO-d$_6$) δ 9.16 (1H, s), 7.74 (1H, s), 7.42 (3H, m), 7.27 (2H, m), 6.34 (1H, s), 4.83 (2H, s), 3.04 (3H, s); $^{13}$C-NMR (DMSO-dr) δ 163.2, 135.7, 134.1, 129.6, 129.5, 127.3, 125.1, 115.4, 61.3, 43.1, 34.8; e/z (ES) 228 (M+1, 100%); calculated for C$_{13}$H$_{13}$N$_3$O HCl, C, 59.21; H, 5.35; N, 15.93. found C, 58.85; H, 5.02; N, 15.76.

EXAMPLE 20

5-(4-Bromo-phenyl)-7-methyl-7,8-dihydro-imidazo[1,5-a]pyrazin-6-one

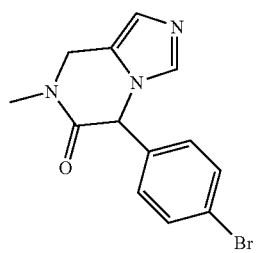

The title compound is prepared analogously to Example 18: m.p. 143-144° C.; $^1$H-NMR (DMSO-d$_6$) δ 7.50 (3H, m), 7.07 (2 h, d, J=8.4), 6.93 (1H, s), 6.13 (1H, s), 4.66 (2H, s), 2.98 (3H, s); $^{13}$C-NMR (DMSO-d$_6$) δ 164.6, 137.3, 135.1, 132.2, 129.0, 123.1, 122.0, 59.7, 43.9, 34.7; e/z (ES) 306/308 (M+1, 100%); calculated for C$_{13}$H$_{12}$N$_3$OBr, C, 51.00; H, 3.95; N, 13.73. found C, 50.65; H, 3.97; N, 13.57.

EXAMPLE 21

5-(4-Bromo-phenyl)-7-(4-methoxy-benzyl)-7,8-dihydro-imidazo[1,5-a]pyrazin-6-one

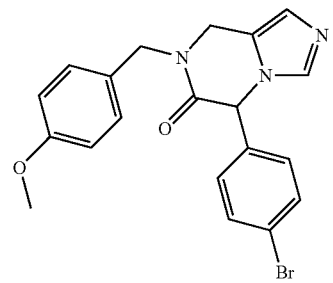

The title compound is prepared analogously to Example 18: m.p. 123-124° C.; $^1$H-NMR (DMSO-d$_6$) 7.61 (1H, s), 7.59 (2H, d, J=8.4), 7.14 (2H, d, J=8.6), 7.06 (2H, d, J=8.4), 6.89 (1H, s), 6.88 (2H, 2H, d, J=8.6), 6.24 (1H, s), 4.65 (1H, d, J=14.5), 4.58 (1H, d, J=16.1), 4.48 (1H, d, J=14.5), 4.45 (1H, d, J=16.1), 3.72 (3H, s); $^{13}$C-NMR (DMSO-d$_6$) δ 164.4, 158.6, 136.4, 134.8, 131.8, 129.2, 128.4, 128.0, 122.9, 121.7, 113.9, 59.4, 54.9, 48.8, 41.06; e/z (ES) 411/413 (M+1, 100%); calculated for C$_{20}$H$_{18}$N$_3$O$_2$Br, C, 58.20; H, 4.40; N, 10.19. found C, 58.08; H, 4.43; N, 10.09.

EXAMPLE 22

5-(4-Bromo-phenyl)-7-cyclopropylmethyl-7,8-dihydro-imidazo[1,5-a]pyrazin-6-one hydrochloride

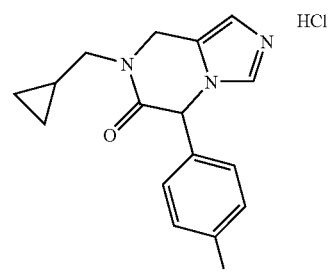

The title compound is prepared analogously to Example 18: m.p. 223-225° C.; $^1$H-NMR (DMSO-d$_6$) δ 9.18 (1H, s), 7.75 (1H, s), 7.65 (2H, d, J=8.4), 7.27 (2H, d, J=8.4), 6.39 (1H, s), 4.95 (1H, d, J=16.6), 4.81 (1H, d, J=16.6), 3.45 (1H, dd, J=13.8, 7.0), 3.32 (1H, dd, J=13.8, 7.0), 1.05 (1H, m), 0.47 (2H, m), 0.27 (2H, m); $^{13}$C-NMR (DMSO-d$_6$) δ 162.5, 134.2, 133.8, 132.0, 129.2, 125.0, 122.5, 115.0, 60.4, 50.6, 40.8, 8.6, 3.2, 2.9; e/z (ES) 346/348 (M+1, 100%); calculated for C$_{16}$H$_{16}$N$_3$OBr HCl, C, 50.22; H, 4.48; N, 10.98. found C, 50.00; H, 4.34; N, 10.76.

EXAMPLE 23

7-Benzyl-S-(4-bromo-phenyl)-7,8-dihydro-imidazo[1,5-a]pyrazin-6-one hydrochloride

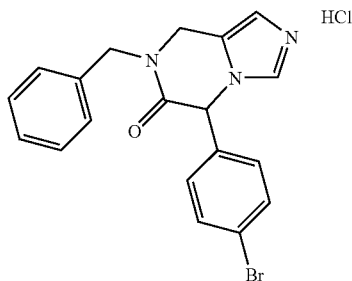

The title compound is prepared analogously to Example 18: m.p. 250° C. (dec.); $^1$H-NMR (DMSO-d$_6$) δ 9.02 (1H, s), 7.67 (3H, m), 7.30 (7H, m), 6.42 (1H, s), 4.70 (4H, m); $^{13}$C-NMR (DMSO-d$_6$) δ 163.0, 135.7, 134.2, 134.0, 132.0, 129.3, 128.6, 127.6, 124.6, 122.6, 115.6, 60.6, 49.5, 40.7; e/z (ES) 382/384 (M+1, 100%); calculated for $C_{19}H_{16}N_3OBr$, C, 54.50; H, 4.09; N, 10.04. found C, 54.05; H, 3.99; N, 9.97.

EXAMPLE 24

5-(4-Bromo-phenyl)-7-(4-chloro-benzyl)-7,8-dihydro-imidazo[1,5-a]pyrazin-6-one hydrochloride

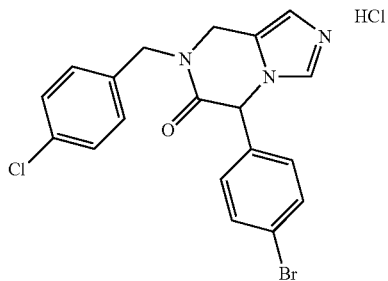

The title compound is prepared analogously to Example 18: m.p. 158-159° C.; $^1$H-NMR (DMSO-d$_6$) δ 7.61 (1H, s), 7.59 (2H, d, J=8.5), 7.38 (2H, d, J=8.4), 7.23 (2H, d, J=8.4), 7.07 (2H, d, J=8.5), 6.91 (1H, s), 6.25 (1H, s), 4.72 (1H, d, J=15.0), 4.62 (1H, d, J=16.0), 4.54 (1H, d, J=15.0), 4.53 (1H, d, J=16.0); $^{13}$C-NMR (DMSO-d$_6$) δ 162.6, 134.4, 133.3, 132.8, 130.8, 129.8, 127.5, 126.5, 126.4, 120.9, 120.0, 119.7, 57.4, 46.8, 39.5; e/z (ES) 418/420 (M+1, 100%); calculated for $C_{19}H_{15}N_3OBrCl$, C, 54.76; H, 3.63; N, 10.08. found C, 54.87; H, 3.64; N, 9.99.

EXAMPLE 25

5-(4-Bromo-phenyl)-7-(4-trifluoromethyl-benzyl)-7,8-dihydro-imidazo[1,5-a]pyrazin-6-one hydrochloride

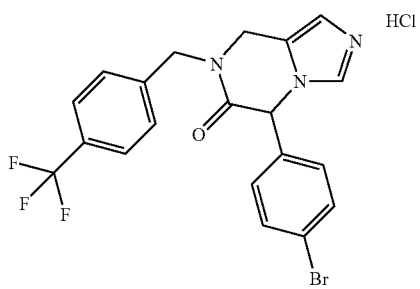

The title compound is prepared analogously to Example 18: m.p. 113-114° C.; $^1$H-NMR (DMSO-d$_6$) δ 7.69 (2H, d, J=8.0), 7.61 (2H, d, J=8.0), 7.60 (1H, s), 7.41 (2H, d, J=8.0), 7.09 (2H, d, J=8.3), 6.92 (1H, s), 6.28 (1H, s), 4.84 (1H, d, J=15.3), 4.67 (1H, d, J=16.0), 4.64 (1H, d, J=16.0), 4.59 (1H, d, J=15.3); $^{13}$C-NMR (DMSO-d$_6$) δ 164.8, 141.2, 136.3, 134.9, 131.8, 128.5, 128.2, 127.8, 125.4, 124.1 (q, J=271.7), 122.9, 122.1, 121.8, 59.5, 49.2, 41.9; e/z (ES) 450/452 (M+1, 100%); calculated for $C_{20}H_{15}N_3OBrF_3$, C, 53.35; H, 3.36; N, 9.33. found C, 53.25; H, 3.29; N, 9.22.

EXAMPLE 26

5-(4-Bromo-phenyl)-7-(4-methoxy-phenyl)-7,8-dihydro-imidazo[1,5-a]pyrazin-6-one hydrochloride

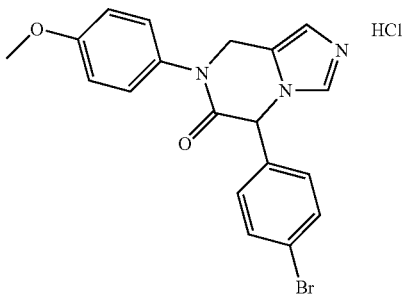

The title compound is prepared analogously to Example 18: m.p. 149-150° C.; $^1$H-NMR (DMSO-d$_6$) δ 7.68 (1H, s), 7.63 (2H, d, J=8.4), 7.25 (2H, d, J=8.9), 7.16 (2H, d, J=8.4), 6.97 (2H, d, J=8.9), 6.96 (1H, s), 6.31 (1H, s), 5.02 (1H, d, J=15.7), 4.88 (1H, d, J=15.7), 3.76 (3H, s); $^{13}$C-NMR (DMSO-d$_6$) δ 165.0, 158.3, 136.6, 135.3, 134.7, 132.3, 129.0, 127.4, 123.4, 123.0, 122.2, 114.5, 60.4, 55.7, 45.7; e/z (ES) 398/400 (M+1, 100%); calculated for $C_{19}H_{16}N_3OBr$, C, 57.30; H, 4.05; N, 10.55. found C, 57.02; H, 4.03; N, 10.37.

EXAMPLE 27

S-(4-Bromo-phenyl)-7-(4-fluoro-phenethyl)-7,8-dihydro-imidazo[1,5-a]pyrazin-6-one hydrochloride

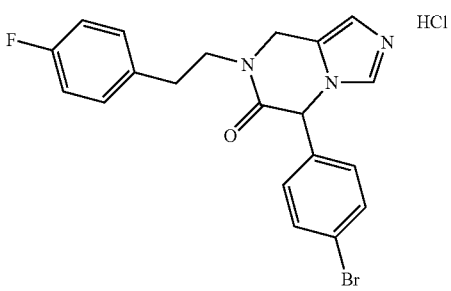

The title compound is prepared analogously to Example 18: m.p. 136-138° C.; $^1$H-NMR (DMSO-d$_6$) δ 9.14 (1H, s), 7.72 (1H, s), 7.61 (2H, d, J=8.4), 7.18 (2H, dd, J=8.6, 5.7), 7.10 (2H, d, J=8.4), 7.00 (2H, app t J=8.9), 6.35 (1H, s), 4.82 (1H, d, J=16.5), 4.60 (1H, d, J=16.5), 3.88 (1H, m), 3.55 (1H, m), 2.80 (2H, m); $^{13}$C-NMR (DMSO-d$_6$) δ 162.5, 160.8 (d, J=241.5), 134.3, 134.2, 133.8, 131.9, 130.4 (d, J=8.3), 128.9, 124.8, 122.4, 115.1, 114.9 (d, J=21.1), 60.5, 48.0, 41.0, 31.3; e/z (ES) 414/416 (M+1, 100%); calculated for $C_{20}H_{17}N_3OFBr$ HCl, C, 53.29; H, 4.02; N, 9.32. found C, 52.97; H, 4.10; N, 9.20.

EXAMPLE 28

5-(4-Bromo-phenyl)-7-(4-fluoro-benzyl)-7,8-dihydro-imidazo[1,5-a]pyrazin-6-one hydrochloride

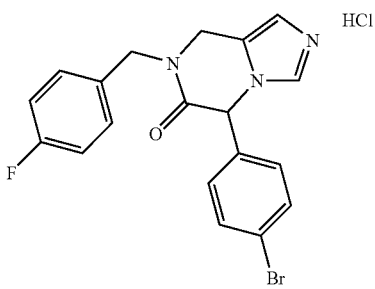

The title compound is prepared analogously to Example 18: m.p. 205-207° C.; $^1$H-NMR (DMSO-d$_6$) δ 9.12 (1H, s), 7.67 (1H, s), 7.64 (2H, d, J=8.5), 7.32 (2H, dd, J=8.5, 5.6), 7.25 (2H, d, J=8.5), 7.21 (2H, app t, J=8.9), 6.44 (1H, s), 4.78 (1H, d, J=14.7), 4.75 (1H, d, J=16.8), 4.67 (1H, d, J=16.8), 4.60 (1H, d, J=14.7); $^{13}$C-NMR (DMSO-d$_6$) δ 163.4, 162.0 (d, J=243.0), 134.5, 134.4, 132.5, 132.4, 130.4 (d, J=8.3), 129.8, 125.1, 123.0, 115.8, 115.7 (d, J=21.3), 61.0, 48.9, 41.1; e/z (ES) 400/402 (M+1, 100%); calculated for C$_{19}$H$_{15}$N$_3$ObrF HCl, C, 52.26; H, 3.69; N, 9.62. found C, 52.53; H, 3.75; N, 9.50.

EXAMPLE 29

5-(3-Bromo-phenyl)-7-methyl-7,8-dihydro-imidazo[1,5-a]pyrazin-6-one hydrochloride

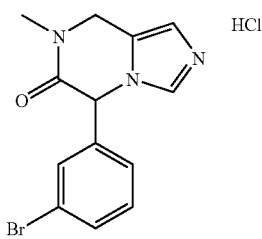

The title compound is prepared analogously to Example 18: m.p. 265° C. (dec.); $^1$H-NMR (DMSO-d$_6$) δ 9.12 (1H, s), 7.74 (1H, s), 7.65 (1H, d, J=8.0), 7.57 (1H, s), 7.39 (1H, t, J=8.0), 7.24 (1H, d, J=8.0), 6.36 (1H, s), 4.83 (2H, m), 3.04 (3H, s); $^{13}$C-NMR (DMSO-d$_6$) δ 162.3, 137.6, 133.7, 132.1, 130.3, 126.1, 124.7, 122.1, 114.9, 60.1, 42.7, 34.5; e/z (ES) 306/308 (M+1, 100%); calculated for C$_{13}$H$_{12}$N$_3$OBr HCl, C, 45.57; H, 3.83; N, 12.26. found C, 45.72; H, 3.98; N, 11.78.

EXAMPLE 30

5-(3-Bromo-phenyl)-7-cyclohexyl-7,8-dihydro-imidazo[1,5-a]pyrazin-6-one oxalate

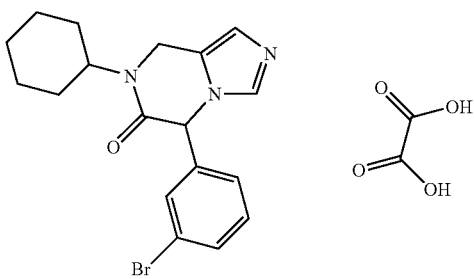

The title compound is prepared analogously to Example 18: m.p. 129-131° C.; $^1$H-NMR (DMSO-d$_6$) 7.86 (1H, s), 7.58 (1H, d, J=7.9), 7.36 (2H, m), 7.07 (2H, m), 6.20 (1H, s), 4.74 (1H, d, J=16.2), 4.40 (1H, d, J=16.2), 4.26 (1H, m), 1.77-1.09 (10H, m); $^{13}$C-NMR (DMSO-d$_6$) 164.0, 161.8, 139.5, 135.0, 131.8, 131.6, 129.6, 125.5, 123.6, 122.4, 60.1, 53.4, 36.7, 29.2, 28.8, 25.5, 25.4, 25.2; e/z (ES) 374/376 (M+1, 100%); calculated for C$_{18}$H$_{20}$N$_3$OBr C$_2$H$_2$O$_4$, C, 51.74; H, 4.78; N, 9.05. found C, 51.43; H, 4.64; N, 8.94.

EXAMPLE 31

5-(4-Bromo-phenyl)-7-(4-methoxy-phenyl)-7,8-dihydro-imidazo[1,5-a]pyrazin-6-one oxalate

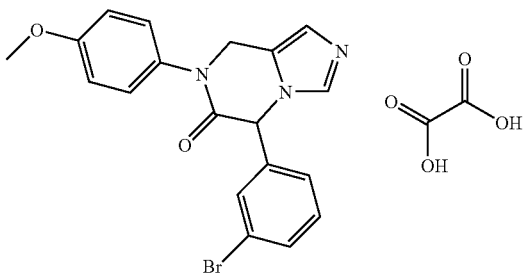

The title compound is prepared analogously to Example 18: m.p. 186-189° C.; $^1$H-NMR (DMSO-d$_6$) δ 7.87 (1H, s), 7.61 (1H, d, J=7.9), 7.44 (1H, s), 7.40 (1H, t, J=7.9), 7.27 (2H, d, J=8.8), 7.20 (1H, d, J=7.9), 7.07 (1H, s), 6.98 (2H, d, J=8.8), 6.35 (1H, s), 5.08 (1H, d, J=15.9), 4.91 (1H, d, J=15.9), 3.77 (3H, s); $^{13}$C-NMR (DMSO-d$_6$) δ164.7, 161.8, 158.4, 139.5, 134.7, 131.9, 131.6, 129.9, 127.4, 125.8, 122.5, 114.5, 60.4, 55.7, 45.6; e/z (ES) 398/400 (M+1, 100%); calculated for C$_{18}$H$_{16}$N$_3$O$_2$Br C$_2$H$_2$O$_4$, C, 51.65; H, 3.72; N, 8.61. found C, 51.49; H, 3.62; N, 8.40.

EXAMPLE 32

5-(3-Bromo-phenyl)-7-cyclopropylmethyl-7,8-dihydro-imidazo[1,5-a]pyrazin-6-one hydrochloride

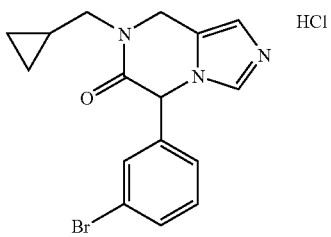

The title compound is prepared analogously to Example 18: m.p. 249-250° C.; $^1$H-NMR (DMSO-d$_6$) δ 9.19 (1H, s), 7.75 (1H, s), 7.65 (1H, d, J=7.9), 7.59 (1H, s), 7.41 (1H, t, J=7.9), 7.28 (1H, d, J=7.9), 6.40 (1H, s), 4.95 (1H, d, J=16.9), 4.85 (1H, d, j 16.9), 3.45 (1H, dd, J=14.0, 7.3), 3.35 (1H, dd, J=14.0, 7.3), 1.03 (1H, m), 0.48 (2H, m), 0.27 (2H, m); $^{13}$C-NMR (DMSO-d$_8$) δ 162.4, 137.3, 133.8, 132.1, 131.4, 130.2, 126.0, 124.9, 122.2, 115.0, 60.2, 50.7, 40.9, 8.7, 3.2, 3.0; e/z (ES) 346/348 (M+1, 100%); calculated for C$_{16}$H$_{16}$N$_3$OBr HCl, C, 50.22; H, 4.48; N, 10.98. found C, 49.93; H, 4.48; N, 10.74.

Separation of the enantiomers of the free base may be achieved using a Chiralpak AD HPLC column under isocratic conditions (isopropanol:hexane—20:80); Retention times 18.5 and 27.6 min.

EXAMPLE 33

7-Benzyl-5-(3-bromo-phenyl)-7,8-dihydro-imidazo[1,5-a]pyrazin-6-one hydrochloride

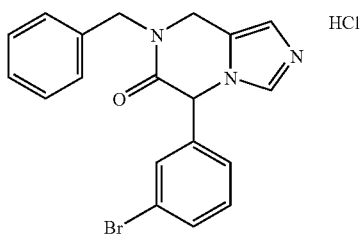

The title compound is prepared analogously to Example 18: m.p. 249-251° C.; $^1$H-NMR (DMSO-d$_6$) δ 9.10 (1H, s), 7.67 (2H, d, J=6.0), 7.57 (1H, s), 7.36 (7H, m), 6.46 (1H, s), 4.72 (4H, m); $^{13}$C-NMR (DMSO-d$_8$) 8162.8, 137.3, 135.7, 134.0, 132.1, 131.3, 130.1, 128.6, 127.7, 127.6, 126.1, 124.6, 122.2, 115.4, 60.4, 49.6, 40.8; e/z (ES) 382/384 (M+1, 100%); calculated for C$_{18}$H$_{16}$N$_3$OBr HCl, C, 54.50; H, 4.09; N, 10.04. found C, 54.47; H, 4.09; N, 10.01.

Separation of the enantiomers may be achieved using a Chiralpak AD HPLC column under isocratic conditions (isopropanol:hexane—20:80); Retention times 26.8 and 29.6 min.

EXAMPLE 34

5-(3-Bromo-phenyl)-7-(4-methoxy-benzyl)-7,8-dihydro-imidazo[1,5-a]pyrazin-6-one hydrochloride

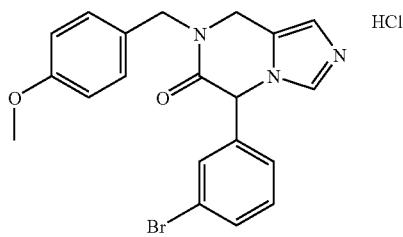

The title compound is prepared analogously to Example 18: m.p. 246-248° C.; $^1$H-NMR (DMSO-d$_6$) δ9.16 (1H, s), 7.68 (1H, s), 7.65 (1H, d, J=7.9), 7.56 (1H, s), 7.40 (1H, t, J=7.9), 7.25 (1H, d, J=7.9), 7.22 (2H, d, J=8.8), 6.90 (2H, d, J=8.8), 6.45 (1H, s), 4.73 (1H, d, J=16.6), 4.71 (1H, d, J=14.6), 4.64 (1H, d, J=16.6), 4.58 (1H, d, J=14.6), 3.74 (3H, s); $^{13}$C-NMR (DMSO-d$_8$) δ 163.0, 159.2, 137.7, 134.3, 132.6, 131.7, 130.6, 129.8, 128.0, 126.5, 125.1, 122.6, 115.6, 114.4, 60.8, 55.5, 49.4, 40.8; e/z (ES) 412/414 (M+1, 100%); calculated for C$_{20}$H$_{18}$N$_3$O$_2$Br HCl, C, 53.53; H, 4.27; N, 9.36. found C, 53.22; H, 4.38; N, 9.16.

EXAMPLE 35

5-(3-Bromo-phenyl)-7-(4-fluoro-benzyl)-7,8-dihydro-imidazo[1,5-a]pyrazin-6-one hydrochloride

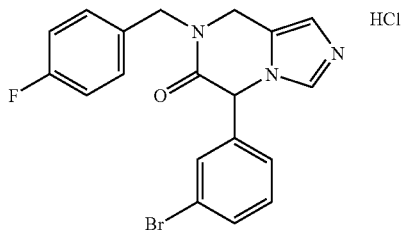

The title compound is prepared analogously to Example 18: m.p. 246-248° C.; $^1$H-NMR (DMSO-d$_6$) δ 9.16 (1H, s), 7.66 (2H, m), 7.57 (1H, s), 7.29 (6H, m), 6.45 (1H, s), 4.76 (1H, d, J=, 15.0), 4.73 (2H, s), 4.62 (1H, d, J=15.0); $^{13}$C-NMR (DMSO-d$_6$) δ 163.2, 162.0 (d, J=242.3), 137.7, 134.3, 132.6, 132.4, 132.3, 131.7, 130.6, 130.4 (d, J=8.3), 126.6, 125.0, 122.6, 115.8 (d, J=, 18.2), 60.8, 49.3, 41.1; e/z (ES) 400/402 (M+1, 100%); calculated for C$_{19}$H$_{15}$N$_3$OBrF HCl, C, 52.26; H, 3.69; N, 9.62. found C, 52.11; H, 3.60; N, 9.56.

EXAMPLE 36

5-(3-Bromo-phenyl)-7-(4-chloro-benzyl)-7,8-dihydro-imidazo[1,5-a]pyrazin-6-one hydrochloride

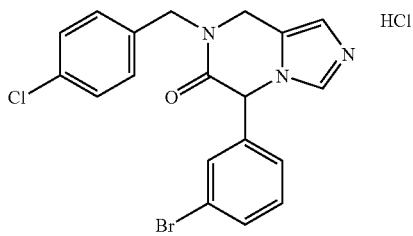

The title compound is prepared analogously to Example 18: m.p. 268-270° C.; $^1$H-NMR (DMSO-d$_6$) δ 9.13 (1H, s), 7.66 (2H, m), 7.57 (1H, s), 7.33 (6H, m), 6.45 (1H, s), 4.80 (1H, d, J=15.1), 4.74 (2H, s), 4.62 (1H, d, J=15.1); $^{13}$C-NMR (DMSO-d$_6$) δ 163.3, 137.6, 135.2, 134.3, 132.7, 132.6, 131.7, 130.7, 130.2, 129.0, 126.6, 125.0, 122.6, 115.7, 60.8, 49.4, 41.3; e/z (ES) 416/418 (M+1, 100%); calculated for C$_{19}$H$_{15}$N$_3$OCl HCl, C, 50.36; H, 3.56; N, 9.27. found C, 50.10; H, 3.56; N, 9.17.

EXAMPLE 37

5-(3-Bromo-phenyl 7-(4-methyl-benzyl)-7,8-dihydro-imidazo[1,5-a]pyrazin-6-one hydrochloride

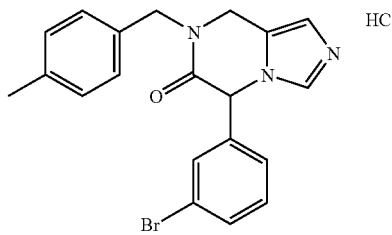

The title compound is prepared analogously to Example 18: m.p. 265-267° C.; $^1$H-NMR (DMSO-d$_6$) δ 9.08 (1H, s), 7.66 (1H, d, J=7.9), 7.65 (1H, s), 7.55 (1H, s), 7.40 (1H, t, J=7.9), 7.25 (1H, d, J=7.9), 7.15 (4H, m), 6.44 (1H, s), 4.73 (1H, d, J=14.7), 4.71 (1H, d, J=15.9), 4.65 (1H, d, J=15.9), 4.61 (1H, d, J=14.7), 2.28 (3H, s); $^{13}$C-NMR (DMSO-d$_6$) δ 163.1, 137.7, 137.3, 134.4, 133.1, 132.6, 131.7, 130.5, 129.6, 128.2, 126.5, 125.0, 122.6, 116.0, 60.7, 49.7, 41.0, 21.0; e/z (ES) 396/398 (M+1, 100%); calculated for C$_{20}$H$_{18}$N$_3$OBr HCl, C, 55.51; H, 4.43; N, 9.71. found C, 55.48; H, 4.46; N, 9.66.

EXAMPLE 38

5-(3-Bromo-phenyl)-7-(4-trifluoromethyl-benzyl)-7,8-dihydro-imidazo[1,5-a]pyrazin-6-one hydrochloride

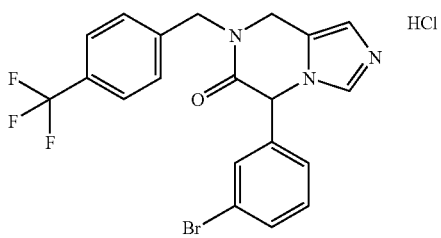

The title compound is prepared analogously to Example 18: m.p. 269-271° C.; $^1$H-NMR (DMSO-d$_6$) δ 9.12 (1H, s), 7.71 (2H, d, J=8.2), 7.68 (1H, s), 7.66 (1H, d, J=7.9), 7.58 (1H, s), 7.51 (2H, d, J=8.2), 7.41 (1H, t, J=7.9), 6.47 (1H, s), 4.92 (1H, d, J=15.4), 4.79 (2H, s), 4.71 (1H, d, J=15.4); $^{13}$C-NMR (DMSO-d) δ 163.5, 141.2, 137.6, 132.6, 131.7, 130.7, 128.9, 128.4, 126.6, 125.9 (q, J=3.8), 125.0, 122.6, 115.8, 60.9, 49.8, 41.6; e/z (ES) 450/452 (M+1, 100%); calculated for $C_{19}H_{15}N_3OBrF_3$ HCl, C, 49.35; H, 3.31; N, 8.63. found C, 49.32; H, 3.34; N, 8.51.

EXAMPLE 39

5-(3-Bromo-phenyl)-7-(3-trifluoromethyl-benzyl)-7, 8-dihydro-imidazo[1,5-a]pyrazin-6-one hydrochloride

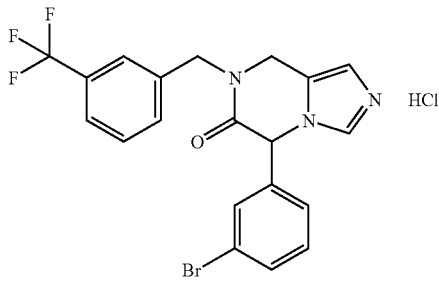

The title compound is prepared analogously to Example 18: m.p. 246-248° C.; $^1$H-NMR (DMSO-d$_6$) δ 9.10 (1H, s), 7.63 (7H, m), 7.40 (1H, t, J=7.9), 7.26 (1H, d, J=7.9), 6.46 (1H, s), 4.80 (4H, m); $^{13}$C-NMR (DMSO-dB) δ 163.5, 137.8, 137.7, 134.4, 132.6, 132.2, 131.7, 130.6, 130.1, 129.9, 127.8 (q, 248.3), 126.4, 125.0, 124.7 (q, J=3.8), 122.6, 115.9, 60.8, 49.7, 41.6; e/z (ES) 450/452 (M+1, 100%); calculated for $C_{19}H_{15}N_3OBrF_3$ HCl C, 49.35; H, 3.31; N, 8.63. found C, 49.33; H, 3.19; N, 8.54.

EXAMPLE 40

5-(3-Bromo-phenyl)-7-(3-fluoro-benzyl)-7,8-dihydro-imidazo[1,5-a]pyrazin-6-one hydrochloride

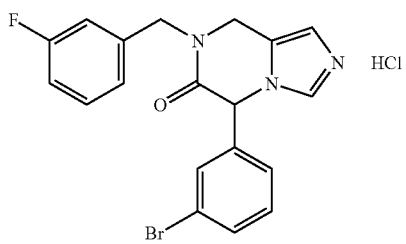

The title compound is prepared analogously to Example 18: m.p. 240-243° C.; $^1$H-NMR (DMSO-d$_6$) δ 9.12 (1H, s), 7.68 (1H, s), 7.66 (1H, d, J=7.9), 7.59 (1H, s), 7.41 (1H, t, J=7.9), 7.38 (1H, t, J=7.6), 7.28 (1H, d, J=7.9), 7.15 (3H, m), 6.45 (1H, s), 4.82 (1H, d, J=15.1), 4.76 (2H, m), 4.65 (1H, d, J=15.1); $^{13}$C-NMR (DMSO) 163.4, 162.7 (d, J=237.3), 139.1 (d, J=6.8), 137.6, 134.4, 132.6, 131.7, 131.0 (d, J=6.8), 130.6, 126.6, 125.0, 124.2 (d, J=2.3), 122.6, 115.8, 114.8 (d, J=21.8), 60.9, 49.6, 41.4; e/z (ES) 400/402 (M+1, 100%); calculated for $C_{19}H_{15}N_3OFBr$ HCl, C, 52.26; H, 3.69; N, 9.62. found C, 52.19; H, 3.45; N, 9.52.

EXAMPLE 41

5-(3-Bromo-phenyl)-7-(3-methyl-benzyl)-7,8-dihydro-imidazo[1,5-a]pyrazin-6-one hydrochloride

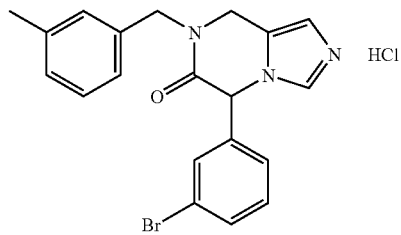

The title compound is prepared analogously to Example 18: m.p. 248-249° C.; $^1$H-NMR (DMSO-d$_6$) δ 9.13 (1H, s), 7.67 (1H, s), 7.66 (1H, d, J=7.9), 7.57 (1H, s), 7.41 (1H, t, J=7.9), 7.26 (1H, d, J=7.9), 7.23 (1H, t, J=7.6), 7.11 (1H, d, J=7.6), 7.05 (1H, d, J=7.6), 7.01 (1H, s), 6.47 (1H, s), 4.74 (1H, d, J=16.5), 4.68 (2H, s), 4.66 (1H, d, J=16.5), 2.25 (3H, s); $^{13}$C-NMR (DMSO-d$_6$) δ 163.1, 138.2, 137.8, 136.0, 134.4, 132.6, 131.7, 130.4, 128.9, 128.7, 128.6, 126.4, 125.3, 125.0, 122.6, 115.8, 60.8, 49.9, 41.2, 21.3; e/z (ES) 396/398 (M+1, 100%); calculated for $C_{20}H_{18}N_3OBr$ HCl, C, 55.51; H, 4.43; N, 9.71. found C, 55.75; H, 4.41; N, 9.68.

EXAMPLE 42

5-(3-Bromo-phenyl)-7-(phenethyl)-7,8-dihydro-imidazo[1,5-a]pyrazin-6-one hydrochloride

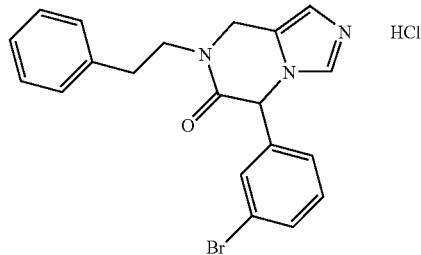

The title compound is prepared analogously to Example 18: m.p. 205-207° C.; $^1$H-NMR (DMSO-d$_6$) δ9.12 (1H, s), 7.69 (1H, s), 7.66 (1H, d, J=8.0), 7.46 (1H, s), 7.38 (1H, t, J=7.9), 7.16 (6H, m), 6.37 (1H, s), 4.79 (1H, d, J=17.0), 4.59 (1H, d, J=17.0), 3.83 (1H, m), 3.60 (1H, m), 2.84 (2H, m); $^{13}$C-NMR (DMSO-dr) δ 162.8, 138.6, 137.5, 134.4, 132.5, 131.7, 130.3, 129.0, 128.7, 126.7, 126.1, 125.2, 122.6, 115.6, 60.8, 48.8, 41.7, 32.6; e/z (ES) 396/398 (M+1, 100%); calculated for $C_{20}H_{18}N_3OBr$ HCl, C, 55.51; H, 4.43; N, 9.71. found C, 55.31; H, 4.23; N, 9.68.

EXAMPLE 43

5-(3-Bromo-phenyl)-7-(4-methoxy-phenethyl)-7,8-dihydro-imidazo[1,5-a]pyrazin-6-one hydrochloride

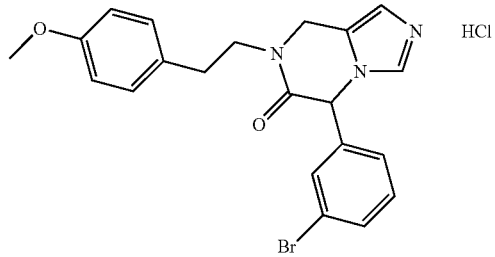

The title compound is prepared analogously to Example 18: m.p. 202-204° C.; $^1$H-NMR (DMSO-d$_6$) δ9.13 (1H, s), 7.69 (1H, s), 7.65 (1H, d, J=9.1), 7.46 (1H, s), 7.37 (1H, t, J=7.9), 7.08 (1H, d, J=8.3), 7.03 (2H, d, J=8.7), 6.77 (2H, d, J=8.7), 6.36 (1H, s), 4.78 (1H, d, J=16.5), 4.56 (1H, d, J=16.5), 8.85 (1H, m), 3.71 (3H, s), 3.55 (1H, m), 2.77 (2H, m); $^{13}$C-NMR (DMSO-d$_6$) δ 162.7, 158.1, 137.5, 134.3, 132.4, 131.7, 130.3, 130.2, 130.0, 126.1, 125.2, 122.6, 115.6, 114.1, 60.8, 55.3, 48.9, 41.7, 31.7; e/z (ES) 426/428 (M+1, 100%); calculated for C$_{21}$H$_{20}$N$_3$O$_2$Br HCl 0.25 H$_2$O, C, 53.98; H, 4.64; N, 8.99. found C, 53.92; H, 4.47; N, 8.93.

EXAMPLE 44

5-(3-Bromo-phenyl)-7-(4-chloro-phenethyl)-7,8-dihydro-imidazo[1,5-a]pyrazin-6-one hydrochloride

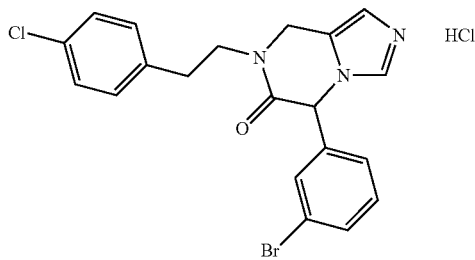

The title compound is prepared analogously to Example 18: m.p. 225-226° C.; $^1$H-NMR (DMSO-d$_6$) 9.12 (1H, s), 7.72 (1H, s), 7.65 (1H, d, 7.9), 7.44 (1H, s), 7.36 (1H, t, J=7.9), 7.23 (2H, d, J=8.6), 7.17 (2H, d, J=8.6), 7.06 (d, J=7.5), 6.35 (1H, s), 4.82 (1H, d, J=16.5), 4.66 (1H, d, J=16.5), 3.88 (1H, m), 3.58 (1H, m), 2.85 (2H, m); $^{13}$C-NMR (DMSO-d$_6$) 162.8, 137.6, 137.4, 134.3, 132.4, 131.6, 131.3, 130.9, 130.3, 128.6, 126.1, 125.2, 122.6, 115.6, 60.8, 48.2, 41.5, 31.8; e/z (ES) 432/434 (M+1, 100%); calculated for C$_{20}$H$_{17}$N$_3$OBrCl HCl, C, 51.42; H, 3.88; N, 8.99. found C, 51.14; H, 3.55; N, 8.98.

EXAMPLE 45

5-(3-Bromo-phenyl)-7-(3-chloro-phenethyl)-7,8-dihydro-imidazo[1,5-a]pyrazin-6-one hydrochloride

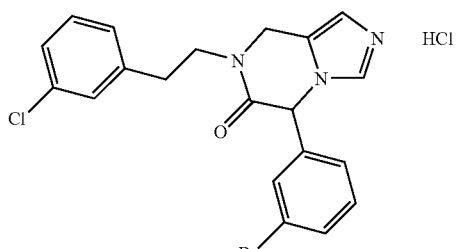

The title compound is prepared analogously to Example 18: m.p. 184-186° C.; $^1$H-NMR (DMSO-d$_6$) δ 9.09 (1H, s), 7.71 (1H, s), 7.64 (1H, d, J=7.9), 7.45 (1H, s), 7.36 (1H, t, J=7.9), 7.24 (3H, m), 7.10 (2H, m), 6.35 (1H, s), 4.81 (1H, d, J=16.6), 4.67 (1H, d, J=16.6), 3.85 (1H, m), 3.62 (1H, m), 2.86 (2H, m); $^{13}$C-NMR (DMSO-d$_6$) δ 162.4, 140.8, 136.9, 133.9, 132.8, 132.0, 131.2, 130.0, 129.9, 128.5, 127.4, 126.3, 125.6, 124.8, 122.2, 115.2, 60.3, 47.7, 41.0, 31.7; e/z (ES) 430/432 (M+1, 100%); calculated for C$_{20}$H$_{17}$N$_3$OBrCl HCl, C, 51.42; H, 3.88; N, 8.99. found C, 51.33; H, 3.70; N, 8.85.

EXAMPLE 46

5-(3-Bromo-phenyl)-7-(4-methyl-phenethyl)-7,8-dihydro-imidazo[1,5-a]pyrazin-6-one hydrochloride

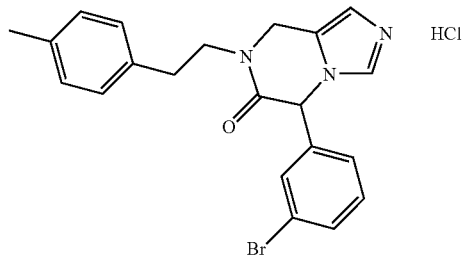

The title compound is prepared analogously to Example 18: m.p. 197-199° C.; $^1$H-NMR (DMSO-d$_6$) δ 9.11 (1H, s), 7.69 (1H, s), 7.66 (1H, d, J=9.1), 7.44 (1H, s), 7.37 (1H, m), 7.08 (1H, d, J=7.5), 7.01 (4H, s), 6.36 (1H, s), 4.78 (1H, d, J=16.6), 4.56 (1H, d, J=16.6), 3.87 (1H, m), 3.56 (1H, m), 2.79 (2H, m), 2.24 (3H, s); $^{13}$C-NMR (DMSO-d$_6$) δ 162.8, 137.4, 135.6, 135.4, 134.3, 132.4, 131.6, 130.2, 129.3, 128.9, 126.1, 125.2, 122.6, 115.6, 60.8, 48.8, 41.6, 32.2, 21.0; e/z (ES) 410/412 (M+1, 100%); calculated for C$_{21}$H$_{20}$N$_3$OBr HCl, C, 56.46; H, 4.74; N, 9.41. found C, 56.36; H, 4.50; N, 9.29.

EXAMPLE 47

5-(3-Bromo-phenyl)-7-(4-fluoro-phenethyl)-7,8-dihydro-imidazo[1,5-a]pyrazin-6-one hydrochloride

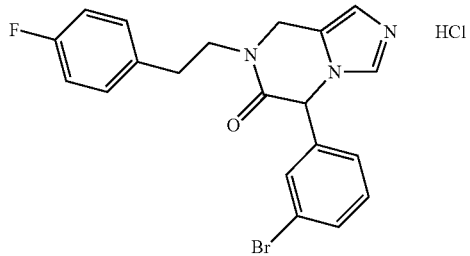

The title compound is prepared analogously to Example 18: m.p. 179-180° C.; $^1$H-NMR (DMSO-d$_6$) δ 9.09 (1H, s), 7.70 (1H, s), 7.64 (1H, d, J=9.0), 7.43 (1H, s), 7.43 (1H, t, J=7.9), 7.17 (2H, dd, J=8.7, 5.6), 7.02 (3H, m), 6.35 (1H, s), 4.80 (1H, d, J=16.9), 4.63 (1H, d, J=16.9), 3.86 (1H, m), 3.57 (1H, m), 2.84 (2H, m); $^{13}$C-NMR (DMSO-d$_6$) δ 162.4, 160.9 (d, J=242.0), 137.0, 134.3, 133.9, 132.0, 131.2, 130.4 (d, J=8.0), 129.8, 125.6, 124.7, 122.1, 115.2, 114.9 (d, J=21.1), 60.3, 48.1, 41.1, 31.3; e/z (ES) 414/416 (M+1, 100%); calculated for C$_{20}$H$_{17}$N$_3$OBrF HCl, C, 53.29; H, 4.02; N, 9.32. found C, 53.02; H, 3.73; N, 9.32.

EXAMPLE 48

5-(3-Bromo-phenyl)-7-thiophen-2-ylmethyl-7,8-dihydro-imidazo[1,5-a]pyrazin-6-one hydrochloride

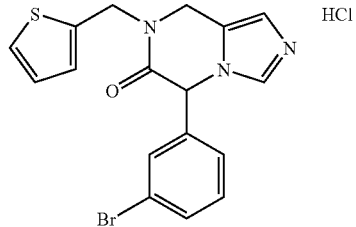

The title compound is prepared analogously to Example 18: m.p. 233-235° C.; $^1$H-NMR (DMSO-d$_6$) δ9.11 (1H, s), 7.70 (1H, s), 7.66 (1H, d, J=9.0), 7.54 (1H, s), 7.50 (1H, d, J=5.2), 7.39 (1H, t, J=7.7), 7.23 (1H, d, J=7.9), 7.14 (1H, d, 2.6), 7.01 (1H, dd, J=5.2, 3.6), 6.45 (1 h, s), 4.81 (4H, m); $^{13}$C-NMR (DMSO-d$_6$) δ 162.88, 137.97, 137.56, 134.42, 132.57, 131.69, 130.54, 128.19, 127.18 (d, J=5.1), 126.44, 124.89, 122.57, 116.00, 60.65, 45.00; e/z (ES) 388/390 (M+1, 100%); calculated for C$_{17}$H$_{14}$BrN$_3$OS HCl, C, 48.07; H, 3.56; N, 9.89. found C, 48.12; H, 3.44; N, 9.81.

EXAMPLE 49

5-(3-Bromo-phenyl)-7-furan-2-ylmethyl-7,8-dihydro-imidazo[1,5-a]pyrazin-6-one hydrochloride

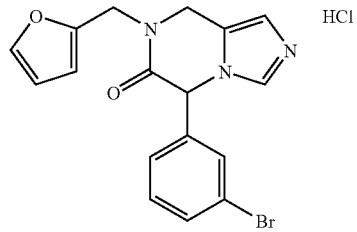

The title compound is prepared analogously to Example 18: m.p. 215-218° C.; $^1$H-NMR (DMSO-d$_6$) δ 9.14 (1H, s), 7.70 (1H, s), 7.66 (2H, m), 7.57 (1H, s), 7.40 (1H, t, J=7.7), 7.26 (1H, d, J=7.9), 6.44 (3H, s), 4.73 (4H, m); $^{13}$C-NMR (DMSO) δ 162.44, 148.86, 143.22, 137.11, 133.88, 132.13, 131.27, 130.15, 126.11, 124.45, 122.14, 115.39, 110.52, 109.32, 60.26, 42.53, 40.68; e/z (ES) 372 (M+1, 100%); calculated for C$_{17}$H$_{14}$BrN$_3$O$_2$ HCl, C, 49.96; H, 3.70; N, 10.28. found C, 50.16; H, 3.66; N, 10.32.

EXAMPLE 50

5-(3-Bromo-phenyl)-7-thiophen-3-ylmethyl-7,8-dihydro-imidazo[1,5-a]pyrazin-6-one

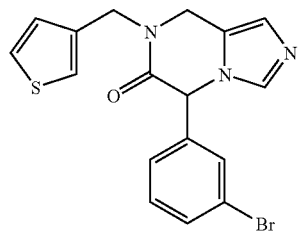

The title compound is prepared analogously to Example 18: m.p. 43-45° C.; $^1$H-NMR (CDCl$_3$) δ 7.50 (2H, d, J=9.0), 7.30-7.21 (3H, m), 7.12 (1H, d, J=3.0), 7.05-7.00 (2H, m), 6.90 (1H, d, J=3.0), 5.91 (1H, s), 4.76 (1H, d, J=15.0), 4.62 (1H, d, J=15.0), 4.53-4.40 (2H, m); $^{13}$C-NMR (CDCl$_3$) δ164.5, 137.9, 135.9, 135.0, 132.2, 130.7, 129.0, 127.2, 127.1, 124.6, 124.1, 123.6, 123.4, 122.0, 60.6, 45.9, 41.7; MS (m/z) 388.0 (M+1, 100%); calculated for C$_{17}$H$_{14}$BrN$_3$OS, C, 52.59; H, 3.63; N, 10.82. found C, 52.34; H, 3.71; N, 10.57.

EXAMPLE 51

5-(3-Bromo-phenyl)-7-furan-3-ylmethyl-7,8-dihydro-imidazo[1,5-a]pyrazin-6-one

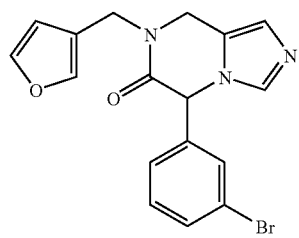

The title compound is prepared analogously to Example 18: $^1$H-NMR (DMSO-d$_6$) δ 7.63-7.56 (m, 4H), 7.36 (d, J=7.9, 1H), 7.31 (d, J=2.5, 1H), 7.06 (d, J=7.9, 1H), 6.92 (s, 1H), 6.30 (s, 1H), 6.22 (s, 1H), 4.68-4.41 (m, 4H); $^{13}$C-NMR (DMSO-d$_6$) δ 164.1, 143.8, 141.1, 139.6, 134.8, 131.3, 131.1, 129.1, 125.1, 122.9, 122.1, 121.9, 119.8, 110.2, 59.2, 41.1, 40.7; MS (m/z) 372.0 (M+1, 100%); calculated for C$_{17}$H$_{14}$BrN$_3$O$_2$, C, 54.86; H, 3.79; N, 11.29. found C, 54.77; H, 3.91; N, 11.11.

EXAMPLE 52

5-(3-Bromo-phenyl)-7-pyridin-3-ylmethyl-7,8-dihydro-imidazo[1,5-a]pyrazin-6-one

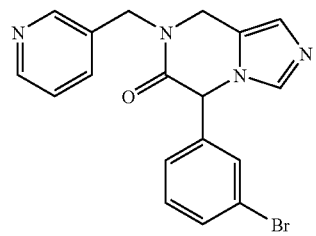

The title compound is prepared analogously to Example 18: m.p. 50-54° C.; $^1$H-NMR (CDCl$_3$) δ 8.56 (dd, J=4.8, J=1.5, 1H), 8.50 (d, J=2.1, 1H), 7.54-7.50 (m, 3H), 7.26-7.22 (m, 3H), 7.04-7.01 (m, 2H), 5.95 (s, 1H), 4.81 (d, J=15.0, 1H), 4.60 (d, J=15.0, 1H), 4.48 (s, 2H); $^{13}$C-NMR (CDCl$_3$) δ164.9, 149.8, 149.4, 137.6, 135.8, 135.1, 132.3, 131.1, 130.8, 128.9, 124.5, 124.3, 124.0, 123.4, 121.6, 60.5, 48.4, 41.9; MS (m/z) 383.2 (M+1, 100%); calculated for C$_{18}$H$_{15}$BrN$_4$O, C, 56.41; H, 3.94; N, 14.62. found: C, 56.36; H, 4.09; N, 14.27.

EXAMPLE 53

5-(3-Bromo-phenyl)-7-pyridin-2-ylmethyl-7,8-dihydro-imidazo[1,5-a]pyrazin-6-one

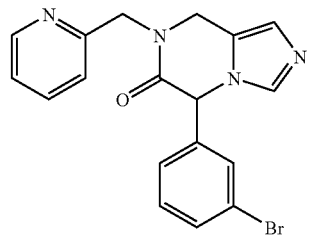

The title compound is prepared analogously to Example 18: m.p. 52-56° C.; $^1$H-NMR (CDCl$_3$) δ 8.52 (d, J=4.8, 1H), 7.66-7.61 (m, 1H), 7.50-7.49 (m, 2H), 7.33 (s, 1H), 7.24-7.18 (m, 3H), 7.09-7.07 (m, 1H), 7.01 (s, 1H), 5.92 (s, 1H), 4.85(d, J=15.0, 1H), 4.76-4.69 (m, 3H); $^{13}$C-NMR (CDCl$_3$) δ 165.8, 156.5, 150.6, 139.0, 138.2, 136.0, 133.3, 131.8, 130.3, 126.0, 125.1, 124.4, 124.0, 123.5, 123.3, 61.7, 53.7, 44.1; MS (m/z) 382.7 (M+1, 100%); calculated for C$_{18}$H$_{15}$BrN$_4$O, C, 56.41; H, 3.94; N, 14.62. found C, 56.76; H, 3.86; N, 14.29.

EXAMPLE 54

5-(3-Bromo-phenyl)-7-pyridin-4-ylmethyl-7,8-dihydro-imidazo[1,5-a]pyrazin-6-one

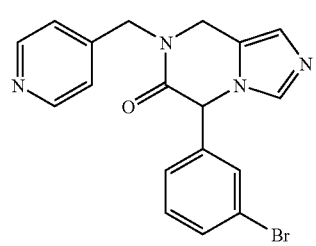

The title compound is prepared analogously to Example 18: m.p. 50-54° C.; $^1$H-NMR (CDCl$_3$) δ 8.55 (d, J=4.5, 1H), 8.54 (d, J=4.5, 1H), 7.53 (s, 1H), 7.51 (s, 1H), 7.33-7.19 (m, 2H), 7.06-7.04 (m, 4H), 4.29 (s, 1H), 4.78 (d, J=15.3, 1H), 4.62 (d, J=15.3, 1H), 4.51 (d, J=15.6, 1H), 4.44 (d, J=15.6, 1H); $^{13}$C-NMR (CDCl$_3$) δ165.1, 150.4, 144.3, 137.4, 135.2, 132.4, 130.8, 128.9, 124.5, 124.3, 123.5, 122.4, 121.6, 60.6, 49.8, 42.3; MS (m/z) 382.7 (M+1, 100%); calculated for CO$_8$H$_{15}$BrN$_4$O, C, 56.41; H, 3.94; N, 14.62. found C, 56.69; H, 4.29; N, 14.32.

EXAMPLE 55

5-(3-Bromo-phenyl)-7-cyclohexylmethyl-7,8-dihydro-imidazo[1,5-a]pyrazin-6-one

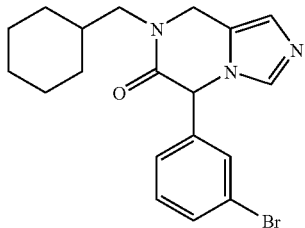

The title compound is prepared analogously to Example 18: $^1$H-NMR (DMSO-d$_6$) δ 7.65 (s, 1H), 7.57 (d, J=9.0, 1H), 7.35 (app. t, J=7.9, 1H), 7.29 (s, 1H), 7.03 (d, J=7.8, 1H), 6.94 (s, 1H), 6.18 (s, 1H), 4.65 (d, J=16.1, 1H), 4.55 (d, J=16.2, 1H), 3.27 (d, J=7.3, 2H), 1.69-1.40 (m, 6H), 1.20-1.09 (m, 3H), 0.90-0.83 (m, 2H); $^{13}$C-NMR (DMSO-d$_6$) δ164.3, 139.5, 134.8, 131.2, 131.1, 129.0, 124.9, 122.7, 122.5, 121.9, 59.4, 52.3, 42.2, 35.0, 30.1, 29.8, 25.8, 25.1; MS (m/z) 388.1 (M+1, 100%); calculated for C$_{19}$H$_{22}$BrN$_3$O, C, 58.77; H, 5.71; N, 10.82. found: C, 58.58; H, 5.96; N, 10.39.

EXAMPLE 56

4-[5-(3-Bromo-phenyl)-6-oxo-5,6-dihydro-8H-imidazo[1,5-a]pyrazin-7-ylmethyl]-piperidine-1-carboxylic acid t-butyl ester

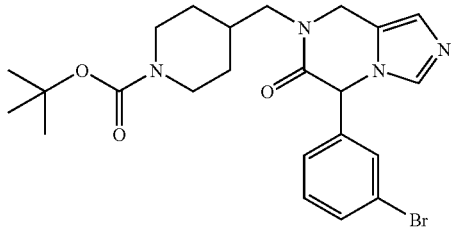

The title compound is prepared analogously to Example 18: $^1$H-NMR (CDCl$_3$) δ 7.74 (s, 1H), 7.63 (d, J=9.1, 1H), 7.40-7.33 (m, 2H), 7.24 (s, 1H), 7.16 (d, J=9.0, 1H), 6.04 (s, 1H), 4.65 (m, 2H), 4.20 (m, 2H), 3.65-3.20 (m, 2H), 2.90-2.68 (m, 2H), 2.32-1.90 (m, 3H), 1.58 (s, 9H), 1.45-1.15 (m, 2H); $^{13}$C-NMR (CDCl$_3$) δ164.2, 154.0, 136.6, 134.3, 131.6, 130.0, 128.1, 123.7, 122.8, 122.7, 121.8, 78.9, 60.0, 52.7, 44.3, 42.6, 35.7, 33.9, 29.0, 28.8, 27.7; MS (m/z) 489.2 (M+1, 100%); calculated for C$_{23}$H$_{29}$BrN$_4$O$_3$, C, 56.44; H, 5.97; N, 11.45. found C, 56.19; H, 6.38; N, 11.07.

EXAMPLE 57

5-(3-Bromo-phenyl)-7-piperidin-4-ylmethyl-7,8-dihydro-imidazo[1,5-a]pyrazin-6-one dihydrochloride

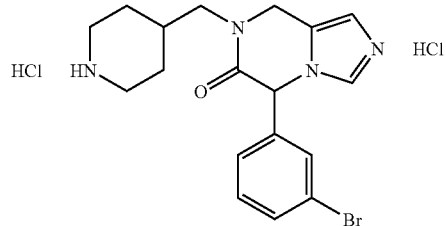

The title compound is prepared analogously to Example 18: $^1$H-NMR (DMSO-d$_6$) δ 9.07 (s, 1H), 7.73 (s, 1H), 7.65 (d, J=8.0, 1H), 7.56 (s, 1H), 7.43-7.38 (m, 1H), 7.25 (d, J=8.0, 1H), 6.38 (s, 1H), 5.76 (s, 2H), 4.82 (s, 2H), 3.50-1.20 (m, 9H); $^{13}$C-NMR (DMSO-d$_6$) δ 163.0, 137.2, 133.9, 132.1, 131.3, 130.2, 126.0, 124.8, 122.1, 115.3, 60.4, 54.9, 51.1, 33.6, 31.3, 26.1, 25.7, 22.5; MS (m/z) 388.9 (M+1, 60%); calculated for C$_{18}$H$_{21}$BrN$_4$O.2HCl, C, 46.77; H, 5.02; N, 12.12. found C, 46.54; H, 5.00; N, 12.01.

EXAMPLE 58

(+)-5-(3-Bromo-phenyl)-7-((R)-1-phenyl-ethyl)-7,8-dihydro-imidazo[1,5-a]pyrazin-6-one

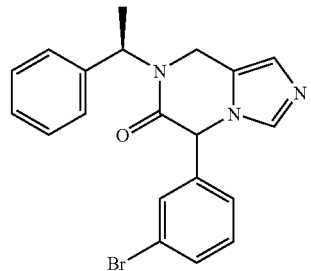

The title compound is prepared analogously to Example 18. The product is obtained as a 3:2 mixture of diastereomers with the more polar diastereoisomer predominating. The diastereomers may be separated using chromatoraphy on silica.

Diastereomer 1 (less polar): m.p. 45-50° C.; [a]D+25.7 (c 1.01, MeOH); $^1$H-NMR (DMSO-d$_6$) δ7.69 (1H, s), 7.60 (1H, d, J=7.9), 7.34 (7H, m), 7.10 (1H, d, J=8.0), 6.85 (1H, s), 6.30 (1H, s), 5.82 (1H, q, J=7.2), 4.49 (1H, d, J=16.2), 4.27 (1H, d, 16.2), 1.49 (3H, d, J=7.2); $^{13}$C-NMR (DMSO-d$_6$) δ 164.7, 139.8 (d, J 3.6), 135.3, 131.7(d, J 9.5), 129.5, 129.0, 127.9, 127.2 125.4, 123.4, 122.6(d, J 16.7), 60.0, 51.4, 36.8, 16.1; e/z (ES) 396/398 (M+1, 100%); calculated for C$_{20}$H$_{16}$BrN$_3$O 0.4H$_2$O, C, 59.53; H, 4.70; N, 10.41. found C, 59.67; H, 4.68; N, 10.14.

Hydrochloride salt of diastereoisomer 2 (more polar): m.p. 199-202° C.; [α]$_D$+150.0 (c 1.01, MeOH); $^1$H-NMR (DMSO-d$_6$) δ 9.09 (1H, s), 7.67 (1H, d, J=7.9), 7.60 (1H, s), 7.53 (1H, s), 7.34 (7H, m), 6.46 (1H, s), 5.85 (1H, q, J=7.1), 4.77 (1H, d, J=16.5), 4.03 (1H, d, J=16.5), 1.57 (3H, d, J=7.1); $^{13}$C-NMR (DMSO-d$_6$) δ 163.2, 139.1, 137.1, 134.3, 132.6, 131.7, 130.6, 129.0, 128.2, 127.4, 126.6, 125.5, 122.6, 115.9, 61.1, 51.7, 36.4, 15.6; e/z (ES) 396 (M+1, 100%); calculated for $C_{20}H_{18}N_3OBr$ HCl, C, 55.51; H, 4.43; N, 9.71. found C, 55.21; H, 4.51; N, 9.57.

EXAMPLE 59

(−)-5-(3-Bromo-phenyl)-7-((S)-1-phenyl-ethyl)-7,8-dihydro-imidazo[1,5-a]pyrazin-6-one

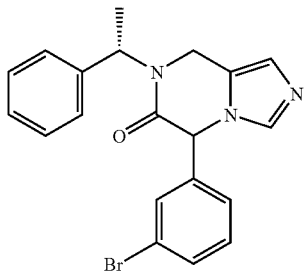

The title compound is prepared analogously to Example 18. The product is obtained as a 3:2 mixture of diastereomers with the more polar diastereoisomer predominating. The diastereomers may be separated using chromatoraphy on silica.

Diastereomer 1 (less polar): m.p. 55-70° C.; $[\alpha]_D$ −24.8 (c 0.533, MeOH); $^1$H-NMR (DMSO-d$_6$) δ 7.69 (1H, s), 7.60 (1H, d, J=7.9), 7.34 (7H, m), 7.10 (1H, d, J=8.0), 6.85 (1H, s), 6.30 (1H, s), 5.82 (1H, q, J=7.2), 4.49 (1H, d, J=16.2), 4.27 (1H, d, 16.2), 1.49 (3H, d, J=7.2); $^{13}$C-NMR (DMSO-d$_6$) 5164.7, 139.8 (d, J 3.6), 135.3, 131.7(d, J 9.5), 129.5, 129.0, 127.9, 127.2 125.4, 123.4, 122.6(d, J 16.7), 60.0, 51.4, 36.8, 16.1; e/z (ES) 396/398 (M+1, 100%); calculated for $C_{20}H_{18}BrN_3O$, C, 60.62; H, 4.58; N, 10.60. found C, 60.52; H, 4.57; N, 10.27.

Diastereoisomer 2 (more polar): m.p. 199-202° C.; $[\alpha]_D$ −156.3 (c 1.121, MeOH); $^1$H-NMR (DMSO-d$_6$) δ 7.63 (1H, s), 7.58 (1H, d, J=7.6), 7.26-7.37 (5H, m), 7.19 (2H, d, J=7.6), 7.02 (1H, d, J=7.9), 6.90 (1H, s), 6.26 (1H, s), 5.85 (1H, q, J=7.2), 4.65 (1H, d, J=15.8), 3.80 (1H, d, J=15.8), 1.54 (3H, d, J=7.2); $^{13}$C-NMR (DMSO-d$_6$) δ 164.80, 139.58, 139.51, 135.21, 131.78, 131.58, 129.50, 128.92, 128.02, 127.29, 125.57, 123.60, 122.95, 122.39, 60.05, 51.28, 36.80, 15.56; e/z (ES) 396/398 (M+1, 100%); calculated for $C_{20}H_{18}BrN_3O$, C, 60.62; H, 4.58; N, 10.60. found C, 60.39; H, 4.61; N, 10.47.

EXAMPLE 60

(+)-5-(4-Bromo-phenyl)-7-((R)-1-phenyl-ethyl)-7,8-dihydro-imidazo[1,5-a]pyrazin-6-one

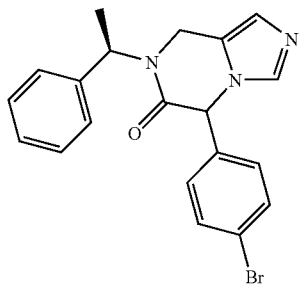

The title compound is prepared analogously to Example 18. The product is obtained as a 3:1 mixture of diastereomers with the more polar diastereoisomer predominating. The diastereomers may be separated using chromatoraphy on silica.

Diastereomer 1 (less polar): m.p. 130-135° C.; $^1$H-NMR (DMSO-d$_6$) δ 7.67(1H, s), 7.62 (2H, d, J=8.43), 7.3 (5H, m), 7.1 (2H, d, J=8.43), 6.84 (1H, s), 6.27 (1H, s), 5.82 (1H, q, J=7.1), 4.45 (1H, d, J=15.9), 4.25 (1H, d, J=15.9), 1.48 (3H, d, J=7.18); $^{13}$C-NMR (DMSO-d$_6$) δ 164.39, 139.38, 136.12, 134.85, 131.89, 128.51, 128.24, 127.47, 126.73, 122.93, 122.31, 121.69, 59.65, 50.83, 36.28, 15.61; e/z (ES) 396/398 (M+1, 100%).

Diastereomer 2 (more polar): m.p. 147-148° C.; [a]D+ 179.4 (c 0.93, MeOH); $^1$H-NMR (DMSO-d$_6$) δ 7.6 (1H, s), 7.58(2H, d, J=8.3), 7.28 (3H, m), 7.17 (2H, m), 7.01 (2H, d, J=8.3), 6.89 (1H, s), 6.23 (1H, s), 5.83 (1H, q, J=7.0), 4.62 (1H, d, J=15.9), 3.79 (1H, d, J=15.9), 1.54 (3H, d, J=7.1); $^{13}$C-NMR (DMSO-d$_6$) 8164.49, 139.03 135.90, 134.73, 131.79, 128.46, 128.35, 127.53, 126.85, 123.04, 122.65, 121.65, 59.79, 50.77, 36.32, 15.13; e/z (ES) 396/398 (M+1, 100%); calculated for $C_{20}H_{18}BrN_3O$, C, 60.62; H, 4.58; N, 10.60. found C, 60.68; H, 4.52; N, 10.62.

EXAMPLE 61

(−)-5-(4-Bromo-phenyl)-7-((S)-1-phenyl-ethyl)-7,8-dihydro-imidazo[1,5-a]pyrazin-6-one

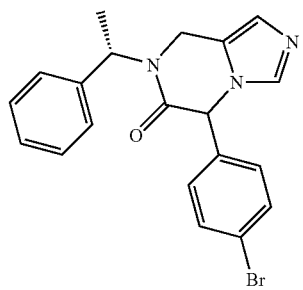

The title compound is prepared analogously to Example 18. The product is obtained as a 3:1 mixture of diastereomers with the more polar diastereoisomer predominating. The diastereomers may be separated using chromatoraphy on silica.

Diastereoisomer 1 (less polar): m.p. 167-168° C.; $[\alpha]_D$ −16.1 (c 0.29, MeOH); $^1$H-NMR (DMSO-d$_6$) δ 7.67 (1H, s), 7.62 (2H, d, J=8.4), 7.32 (5H, m), 7.10 (2H, d, J=8.4), 6.84 (1H, s), 5.82 (1H, q, J=7.1), 4.45 (1H, d, J=15.9), 4.26 (1H, d, J=15.9), 1.48 (3H, d, J=7.1); $^{13}$C-NMR (DMSO-d$_6$) δ 164.4, 139.4, 136.1, 134.9, 131.9, 128.5, 128.3, 127.5, 126.7, 122.9, 122.3, 121.7, 59.7, 50.8, 36.3, 15.6; e/z (ES) 394/396 (M+1, 100%); calculated for $C_{20}H_{18}N_3OBr$, C, 60.62; H, 4.58; N, 10.60. found C, 60.55; H, 4.61; N, 10.61.

Diastereoisomer 2 (more polar): m.p. 146-147° C.; $[\alpha]_D$ −173.8 (c 0.92, MeOH); $^1$H-NMR (DMSO-d$_6$) δ 7.60 (1H, s), 7.58 (2H, d, J=8.3), 7.29 (4H, m), 7.16 (2H, m), 7.02 (2H, d, J=8.3), 6.90 (1H, s), 6.23 (1H, s), 5.83 (1H, q, J=7.0), 4.62 (1H, d, J=15.9), 3.80 (1H, d, J=15.9), 1.54 (3H, d, J=7.0); $^{13}$C-NMR (DMSO-dr) δ 164.5, 139.0, 135.9, 134.7, 131.8, 128.5, 128.4, 127.5, 126.9, 123.0, 122.6, 121.7, 59.8, 50.8, 36.3, 15.1; e/z (ES) 394/396 (M+1, 100%); calculated for $C_{20}H_{18}N_3OBr$, C, 60.62; H, 4.58; N, 10.60. found C, 60.28; H, 4.70; N, 10.61.

EXAMPLE 62

(−)-(4-[6-Oxo-7-((S)-1-phenyl-ethyl)-5,6,7,8-tetrahydro-imidazo[1,5-a]pyrazin-5-yl]-benzonitrile

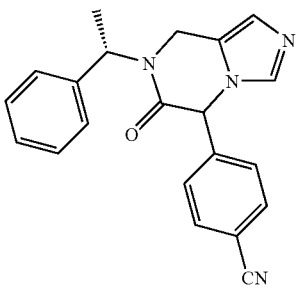

The title compound is prepared analogously to Example 18. The product is obtained as a mixture of diastereomers. The diastereomers may be separated using chromatoraphy on silica.

Diastereomer 1 (less polar): m.p. 157-158° C.; [α]$_D$–13.8 (c 0.94, MeOH); $^1$H NMR (DMSO-d$_6$) δ 7.90 (d, J=8.4, 2H), 7.68 (s, 1H), 7.39-7.26 (m, 7H), 6.86 (s, 1H), 6.41 (s, 1H), 5.80 (q, J=7.2, 1H), 4.48 (d, J=15.9, 1H), 4.27 (d, J=15.9, 1H), 1.47 (d, J=7.2, 3H); $^{13}$C-NMR (DMSO-d$_6$) δ 163.9, 141.8, 139.3, 134.9, 133.0, 128.5, 127.5, 127.1, 126.7, 123.0, 122.3, 118.3, 111.3, 59.9, 51.0, 36.3, 15.6; MS (m/z) 343.1 (M+1, 100%); calculated for C$_{21}$H$_{18}$N$_4$O, C, 73.67; H, 5.30; N, 16.36. found C, 73.48; H, 5.24; N, 16.31.

Diastereomer 2 (more polar): m.p. 75-77° C.; [α]$_D$–213.0 (c 1.00, MeOH); $^1$H NMR (DMSO-d$_6$) δ 7.87 (d, J=8.3, 2H), 7.60 (s, 1H), 7.31-7.24 (m, 5H), 7.14 (d, J=6.9, 2H), 6.92 (s, 1H), 6.37 (s, 1H), 5.81 (q, J=7.1, 1H), 4.63 (d, J=16.0, 1H), 3.81 (d, J=16.0, 1H), 1.54 (d, J=7.1, 3H); $^{13}$C-NMR (DMSO-d$_8$) δ 166.1, 143.8, 141.1, 136.9, 135.0, 130.6, 129.7, 129.3, 128.9, 125.3, 124.8, 120.4, 113.4, 62.2, 53.0, 38.5, 17.2; MS (m/z) 343.1 (M+1, 100%); calculated for C$_{21}$H$_{18}$N$_4$O.0.1H$_2$O, C, 73.06; H, 5.28; N, 16.24. found C, 72.84; H, 5.46; N, 16.01.

EXAMPLE 63

7-Benzyl-7,8-dihydro-imidazol-[1,5-a]pyrazin-6-one hydrochloride

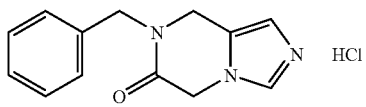

A. Ethyl (5-hydroxy-imidazoyl-1-yl)-acetate

To a solution of the title A compound in Example 18, 4-(t-butyldimethylsilanoxy-methyl)-1-trityl-1H-imidazole (18.16 g, 40.0 mmol) in acetonitrile (50 mL) is added ethyl bromoacetate (6.68 g, 40.0 mmol) and the mixture stirred for 18 h. The mixture is vacuum filtered, the filtrate is concentrated in vacuo and treated with EtOH/HCl (g) solution (35 mL) and the mixture is stirred for 4 days. The resulting suspension is vacuum filtered and washed with fresh EtOH to give a clear filtrate. The solution is concentrated to a smaller volume and treated with propylene oxide (25 mL) and stirred overnight at RT. Again vacuum filtered off the solids and concentrated the filtrate in vacuo. The residue is chromatographed through a silica gel column and eluted with EtOAc: MeOH:NH$_4$OH (95:5:1) to give ethyl (5-hydroxy-imidazoyl-1-yl)-acetate as an oil: $^1$H-NMR (CDCl$_3$) δ7.45 (1H, s), 6.90 (1H, s), 4.80 (2H, s), 4.59 (2H, s), 4.23 (2H, q, J=7.2), 3.73 (1H, br s), 1.29 (3H, t, J=7.2); $^{13}$C-NMR (CDCl3) δ 166.2, 137.3, 129.4, 126.2, 60.3, 52.3, 44.5, 12.2; e/z (ES) 185 (M+1, 100%).

B. Ethyl (5-formyl-imidazoyl-1-yl)-acetate

The title B compound is prepared analogously to the title C compound in Example 18: $^1$H-NMR (CDCl$_3$) δ 9.75 (1H, s), 7.84 (1H, s), 7.69 (1H, s), 5.05 (2H, s), 4.25 (2H, q, J=7.2), 1.29 (3H, t, J=7.2); $^{13}$C-NMR (CDCl$_3$) δ 179.9, 167.4, 143.5, 131.6, 62.5, 48.4, 14.4; e/z (ES) 183 (M+1, 100%).

C. 7-Benzyl-7,8-dihydro-imidazo[1,5-a]pyrazin-6-one hydrochloride

The title C compound is prepared analogously to the title D compound in Example 18: m.p. 201-204° C.; $^1$H-NMR (DMSO-d$_8$) δ 9.12 (1H, s), 7.56 (1H, s), 7.35 (5H, m), 5.04 (2H, s), 4.71 (2H, s), 4.59 (2H, s); $^{13}$C-NMR (DMSO-d$_6$) δ 162.8, 136.3, 133.6, 129.0, 128.2, 127.9, 125.4, 114.6, 49.4, 47.9, 41.3; e/z (ES) 228 (M+1, 100%); calculated for C$_{13}$H$_{13}$N$_3$O HCl, C, 59.21; H, 5.35; N, 15.93. found C, 58.87; H, 5.41; N, 15.85.

EXAMPLE 64

7-(4-Methyl-benzyl)-7,8-dihydro-imidazo[1,5-a]pyrazin-6-one

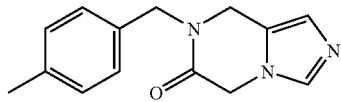

The title compound is prepared analogously to Example 63: m.p. 105-108° C.; $^1$H-NMR (DMSO-d$_6$) δ 7.60 (s, 1H), 7.19-7.13 (m, 4H), 6.75 (s, 1H), 4.81 (s, 2H), 4.61 (s, 2H), 4.46 (s, 2H), 2.28 (s, 3H); $^{13}$C-NMR (DMSO-d$_6$) δ 164.0, 136.5, 134.5, 133.3, 129.0, 127.7, 122.3, 122.2, 48.6, 46.2, 41.5, 20.6; MS (m/z) 242.1 (M+1, 100%); calculated for C$_{14}$H$_{15}$N$_3$O.0.1H$_2$O, C, 69.11; H, 6.17; N, 17.28. found C, 68.95; H, 6.39; N, 17.07.

EXAMPLE 65

7-(4-Fluoro-benzyl)-7,8-dihydro-imidazo[1,5-a]pyrazin-6-one

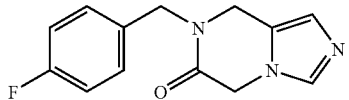

The title compound is prepared analogously to Example 63: m.p. 112-114° C.; $^1$H-NMR (DMSO-d$_6$) δ 7.60 (s, 1H), 7.37-7.32 (m, 2H), 7.20-7.14 (m, 2H), 6.76 (s, 1H), 4.81 (s, 2H), 4.64 (s, 2H), 4.49 (s, 2H); $^{13}$C-NMR (DMSO-d$_6$) δ 164.2, 161.4 (d, J=241.5), 134.5, 132.7 (d, J=3.0), 129.8 (d, J=8.2), 122.3, 122.1, 115.2 (d, J=21.0), 48.3, 46.2, 41.7; MS (m/z) 246.0 (M+1, 100%); calculated for C$_{13}$H$_{12}$FN$_3$O, C, 63.66; H, 4.93; N, 17.13. found C, 63.43; H, 4.97; N, 17.00.

EXAMPLE 66

3-(7-Benzyl-5-oxo-5,6,7,8-tetrahydro-imidazo[1,5-a]pyrazin-5-yl)-benzonitrile

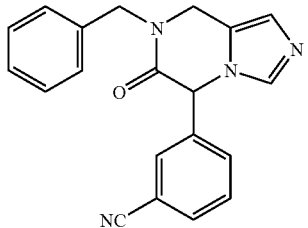

To a solution of the title compound of Example 33, 7-benzyl-5-(3-bromo-phenyl)-7,8-dihydro-imidazo[1,5-a]pyrazin-6-one (0.550 g, 1.44 mmol) in DMF (2 mL) is added zinc(II) cyanide (0.100 g, 0.85 mmol) followed by tetrakistriphenylposphine palladium (0) (0.100 g, 6 mol %). The reaction mixture is degassed, purged with nitrogen then heated at 90° C. for 1 h. The reaction mixture is partitioned between aqueous ammonium hydroxide (2N) and EtOAc. Following washing of the combined organic phases with brine, drying (anhydrous sodium sulfate) and removal of the solvent the residue is subjected to flash chromatography (silica) eluting with EtOAc:MeOH:NH$_4$OH (90:10:1) to give the desired material which is recrystallized from diethyl ether to afford 3-(7-benzyl-6-oxo-5,6,7,8-tetrahydro-imidazo[1,5-a]pyrazin-5-yl)-benzonitrile: m.p. 163-165° C.; $^1$H-NMR (CDCl$_3$) δ 7.66 (1H, d, J=7.6), 7.50 (1H, t, J=6.8), 7.48 (1H, s), 7.33 (2H, m), 7.31 (3H, m), 7.17 (2H, m), 7.01 (1H, s), 6.01 (1H, s), 4.78 (1H, d, J=14.7), 4.60 (1H, d, J=14.7), 4.50 (1H, d, J=15.7), 4.41 (1H, d, J=15.7); $^{13}$C-NMR (CDCl$_3$) δ164.1, 137.4, 135.0, 134.8, 132.6, 130.4, 130.0, 129.4, 129.0, 128.2, 128.0, 124.3, 121.8, 117.9, 113.5, 60.3, 50.7, 41.5; e/z (ES) 329 (M+1, 100%); calculated for C$_{20}$H$_{16}$N$_4$O, C, 73.15; H, 4.91; N, 17.06. found C, 72.81; H, 4.95; N, 16.90.

EXAMPLE 67

3-[7-(4-Methyl-benzyl)-6-oxo-5,6,7,8-tetrahydro-imidazo[1,5-a]pyrazin-5-yl]-benzonitrile hydrochloride

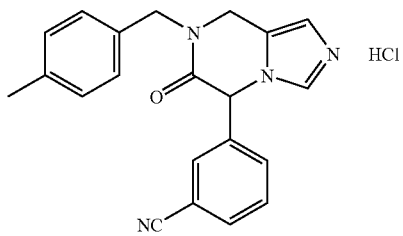

The title compound is prepared analogously to Example 66: m.p. 260-263° C.; $^1$H-NMR (DMSO-d$_6$) δ 9.11 (1H, s), 7.94 (1H, d, J=6.8), 7.81 (1H, s), 7.67 (3H, m), 7.16 (4H, s), 6.52 (1H, s), 4.74 (1H, d, J=14.7), 4.72 (2H, s), 4.58 (1H, d, J=14.7), 2.28 (3H, s); $^{13}$C-NMR (DMSO-d$_6$) δ 162.9, 137.4, 136.6, 134.3, 133.5, 133.0, 132.9, 131.5, 130.7, 129.6, 128.3, 125.2, 118.6, 115.6, 112.5, 60.8, 49.7, 41.0, 21.0; e/z (ES) 342 (M+1, 100%); calculated for C$_{21}$H$_{18}$N$_4$O HCl, C, 66.57; H, 5.05; N, 14.79. found C, 66.23; H, 4.94; N, 14.43.

EXAMPLE 68

3-[7-(4-Fluoro-benzyl)-6-oxo-5,6,7,8-tetrahydro-imidazo[1,5-a]pyrazin-5-yl]-benzonitrile hydrochloride

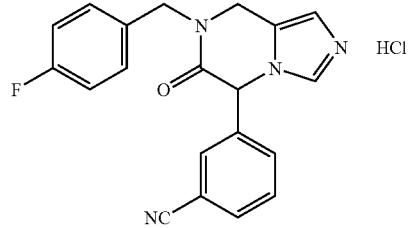

The title compound is prepared analogously to Example 66: m.p. 260-263° C.; $^1$H-NMR (DMSO-d$_6$) δ 9.08 (1H, s), 7.94 (1H, d, J=6.8), 7.82 (1H, s), 7.67 (3H, m), 7.35 (1H, d, J=8.7), 7.33 (1H, d, J=8.7), 7.16 (2H, app t, J=8.7), 6.51 (1H, s), 4.80 (1H, d, J=15.0), 4.79 (1H, d, J=16.9), 4.72 (1H, d, J=16.9), 4.59 (1H, d, J=15.0); $^{13}$C-NMR (DMSO-d$_6$) δ 163.1, 162.0 (d, J=243.4), 136.6, 134.4, 133.5, 133.0, 132.4 (d, J=2.9), 131.6, 130.7, 130.4 (d, J=8.0), 125.1, 118.6, 115.8 (d, J=21.8), 115.7, 112.5, 60.8, 49.6, 41.2; e/z (ES) 347 (M+1, 100%); calculated for C$_{20}$H$_{15}$N$_4$° F. HCl, C, 62.75; H, 4.21; N, 14.64. found C, 62.40; H, 3.86; N, 14.28.

EXAMPLE 69

3-[7-(4-Chloro-benzyl)-6-oxo-5,6,7,8-tetrahydro-imidazo[1,5-a]pyrazin-5-yl]-benzonitrile hydrochloride

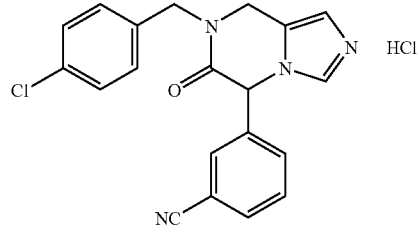

The title compound is prepared analogously to Example 66: m.p. 236-238° C.; $^1$H-NMR (DMSO-d$_6$) δ 9.08 (1H, s), 7.94 (1H, d, J=7.2), 7.83 (1H, s), 7.69 (3H, m), 7.42 (2H, d, J=8.7), 7.32 (2H, d, J=8.7), 6.52 (1H, s), 4.81 (1H, d, J=15.1), 4.79 (1H, d, J=16.2), 4.73 (1H, d, J=16.2), 4.59 (1H, d, J=15.1); $^{13}$C-NMR (DMSO-d$_6$) δ 163.2, 136.6, 135.2, 134.4, 133.5, 133.0, 132.7, 131.6, 130.7, 130.2, 129.0, 125.1, 118.6, 115.7, 112.5, 60.8, 49.4, 41.3; e/z (ES) 363 (M+1, 100); calculated for C$_{20}$H$_{15}$N$_4$O HCl 0.2H$_2$O, C, 59.62; H, 3.85; N, 13.91. found C, 59.69; H, 3.97; N, 13.83.

EXAMPLE 70

3-[7-(4-Methoxy-benzyl)-6-oxo-5,6,7,8-tetrahydro-imidazo[1,5-a]pyrazin-5-yl]-benzonitrile hydrochloride

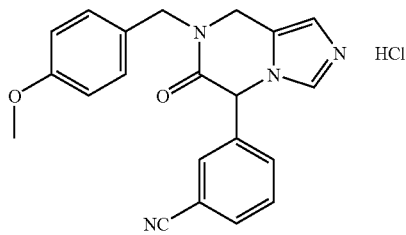

The title compound is prepared analogously to Example 66: m.p. 246-248° C.; $^1$H-NMR (DMSO-d$_6$) δ 9.08 (1H, s), 7.94 (1H, d, J=6.8), 7.80 (1H, s), 7.69 (3H, m), 7.22 (2H, d, J=8.2), 6.91 (2H, d, J=8.2), 6.51 (1H, s), 4.73 (1H, d, J=14.7), 4.71 (2H, s), 4.55 (1H, d, J=14.7), 3.74 (3H, s); $^{13}$C-NMR (DMSO-d$_6$) δ 162.9, 159.2, 136.7, 134.3, 133.4, 132.9, 131.5, 130.7, 129.8, 127.9, 125.1, 118.6, 115.7, 114.4, 112.5, 60.7, 55.4, 49.4, 40.9; e/z (ES) 359 (M+1, 100%); calculated for $C_{21}H_{18}N_4O_2$, C, 63.88; H, 4.85; N, 14.19. found C, 63.61; H, 4.73; N, 13.95.

EXAMPLE 71

3-[7-(4-Fluoro-phenethyl)-6-oxo-5,6,7,8-tetrahydro-imidazol[1,5-a]pyrazin-5-yl]-benzonitrile hydrochloride

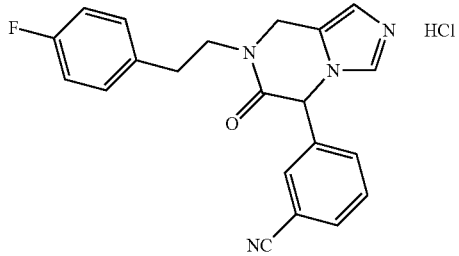

The title compound is prepared analogously to Example 66: m.p. 221-223° C.; $^1$H-NMR (DMSO-d$_6$) δ 9.05 (1H, s), 7.92 (1H, d, J=7.9), 7.72 (1H, s), 7.66 (2H, m), 7.51 (1H, d, J=8.3), 7.18 (2H, dd, J=8.7, 5.7), 6.99 (2H, m), 6.40 (1H, s), 4.81 (1H, d, J=16.6), 4.70 (1H, d, J=16.6), 3.86 (1H, m), 3.58 (1H, m), 2.84 (2H, m); $^{13}$C-NMR (DMSO-d$_6$) δ 162.2, 160.6 (d, J=243.0), 136.0, 134.2, 133.9, 132.9, 132.0, 130.7, 130.3 (d, J=7.6), 130.2, 124.8, 118.1, 115.2, 114.9 (d, J=21.3), 112.0, 60.26, 48.0, 41.06, 31.2; e/z (ES) 361 (M+1, 100%); calculated for $C_{21}H_{17}N_4°F.HCl$, C, 63.56; H, 4.57; N, 14.12. found C, 63.28; H, 4.44; N, 14.01.

EXAMPLE 72

3-[7-Phenethyl-6-oxo-5,6,7,8-tetrahydro-imidazo[1,5-a]pyrazin-5-yl]-benzonitrile hydrochloride

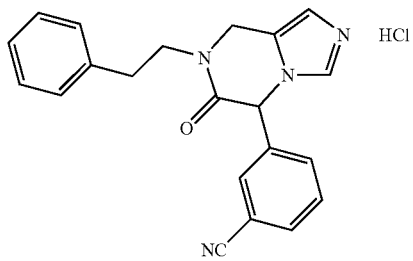

The title compound is prepared analogously to Example 66: m.p. 203-205° C.; $^1$H-NMR (DMSO-d$_6$) δ 9.07 (1H, s), 7.92 (1H, d, J=7.5), 7.70 (1H, s), 7.66 (2H, m), 7.52 (1H, d, J=8.3), 7.18 (5H, m), 6.42 (1H, s), 4.80 (1H, d, J=16.6), 4.67 (1H, d, J=16.6), 3.86 (1H, m), 3.60 (1H, m), 2.85 (2H, m); $^{13}$C-NMR (DMSO-d$_6$) δ 162.6, 138.6, 136.5, 134.4, 133.3, 132.5, 131.2, 130.7, 129.0, 128.7, 126.7, 125.2, 118.6, 115.6, 112.5, 60.7, 48.6, 41.6, 32.6; e/z (ES) 343 (M+1, 100%); calculated for $C_{21}H_{18}N_4O$ HCl, C, 66.57; H, 5.05; N, 14.79. found C, 66.27; H, 4.91; N, 14.62.

EXAMPLE 73

3-[7-Cyclopropylmethyl-6-oxo-5,6,7,8-tetrahydro-imidazo[1,5-a]pyrazin-5-yl]-benzonitrile hydrochloride

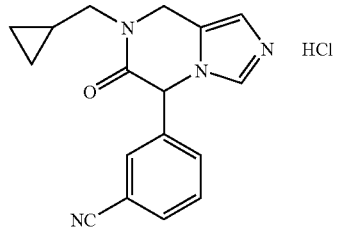

The title compound is prepared analogously to Example 66: m.p. 225-227° C.; $^1$H-NMR (DMSO-d$_6$) δ 9.12 (1H, s), 7.92 (1H, m), 7.83 (1H, s), 7.75 (1H, s), 7.67 (2H, m), 6.47 (1H, s), 4.94 (1H, d, J=16.9), 4.91 (1H, d, J=16.9), 3.39 (2H, d, J=7.2), 1.05(1H, m), 0.48 (2H, m), 0.28 (2H, m); $^{13}$C-NMR (DMSO-d$_6$) δ 161.9, 136.0, 133.5, 132.6, 132.0, 130.8, 130.0, 124.6, 117.8, 114.8, 111.8, 59.9, 50.4, 40.6, 8.3, 2.8, 2.7; e/z (ES) 293 (M+1, 100%); calculated for $C_{17}H_{16}N_4O$ HCl, C, 62.10; H, 5.21; N, 17.04. found C, 62.02; H, 5.05; N, 17.11.

EXAMPLE 74

5-(4'-Chlorobiphenyl-4-yl)-7-(4-methoxy-benzyl)-7,8-dihydro-imidazo[1,5-a]pyrazin-6-one hydrochloride

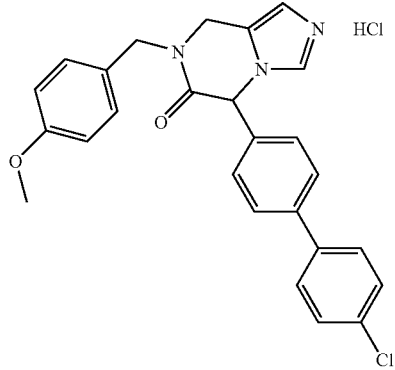

To a solution of the title compound of Example 21, 5-(4-bromo-phenyl)-7-(4-methoxy-benzyl)-7,8-dihydro-imidazo[1,5-a]pyrazin-6-one (0.125 g, 0.30 mmol) in DMF (2 mL) is added potassium phosphate (0.129 g, 0.61 mmol) and 4-chlorophenyl boronic acid (0.057 g, 0.36 mmol) followed by [1,1'-bis(diphenylphosphino)-ferrocene]dichloropalladium (II) (0.025 g, 10 mol %). The reaction mixture is degassed, purged with nitrogen then heated at 95° C. for 5 h. The reaction mixture is partitioned between water and EtOAc. The combined organic phases are washed with brine, dried (anhydrous sodium sulfate) and concentrated. The residue is subjected to flash chromatography (silica) eluting with EtOAc: MeOH:NH$_4$OH (90:10:1) to give 5-(4'-chlorobiphenyl-4-yl)-7-(4-methoxy-benzyl)-7,8-dihydro-imidazo[1,5-a]pyrazin-6-one which is dissolved in diethyl ether and treated with HCl(g)-MeOH and the precipitated product, 5-(4'-chlorobiphenyl-4-yl)-7-(4-methoxy-benzyl)-7,8-dihydro-imidazo[1,5-a]pyrazin-6-one hydrochloride is collected by filtration and dried: m.p. 270-273° C.; $^1$H-NMR (DMSO-d$_8$) δ 9.19 (1H, s), 7.73 (5H, m), 7.54 (2H, d, J=8.3), 7.37 (2H, d, J=8.3), 7.22 (2H, d, J=8.6), 6.90 (2H, d, J=8.6), 6.49 (1H, s), 4.67 (4H, m), 3.73 (3H, s); $^{13}$C-NMR (DMSO-d$_6$) 163.0, 158.8, 139.6, 137.9, 134.4, 133.9, 132.7, 129.4, 128.9, 128.5, 127.6, 127.4, 124.7, 115.3, 114.0, 60.8, 55.0, 48.9; e/z (ES) 444 (M+1, 100%); calculated for C$_{26}$H$_{22}$N$_3$O$_2$Cl HCl, C, 65.01; H, 4.83; N, 8.75. found C, 64.64; H, 4.78; N, 8.74.

EXAMPLE 75

7-(4-Methoxy-benzyl)-5-(4-thiophen3-yl-phenyl)-7,8-dihydro-imidazo[1,5-a]pyrazin-6-one

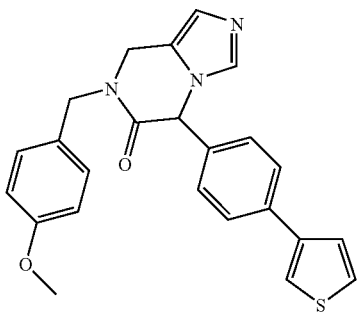

The title compound is prepared analogously to Example 74: m.p. 162-164° C.; $^1$H-NMR (DMSO-d$_6$) δ 7.89 (1H, dd, J=2.8, 1.1), 7.72 (2H, d, J=8.3), 7.65 (2H, m), 7.54 (1H, dd, J=5.0, 1.1), 7.15 (4H, app t, J=9.0), 6.90 (1H, s), 6.87 (2H, d, J=8.6), 6.25 (1H, s), 4.55 (4H, m), 3.71 (3H, s); $^{13}$C-NMR (DMSO-d$_6$) δ 165.2, 159.1, 141.0, 136.2, 135.6, 135.2, 129.6, 128.6, 127.6, 127.1, 127.0, 126.5, 123.3, 122.7, 121.9, 114.4, 60.3, 55.4, 49.2, 41.5; e/z (ES) 416 (M+1, 100%); calculated for C$_{24}$H$_{21}$N$_3$O$_2$S, C, 69.37; H, 5.09; N, 10.11. found C, 69.19; H, 5.08; N, 9.91.

EXAMPLE 76

7-Cyclopropylmethyl-5-(4-thiophen-3-yl-phenyl)-7,8-dihydro-imidazo[1,5-a]pyrazin-6-one hydrochloride

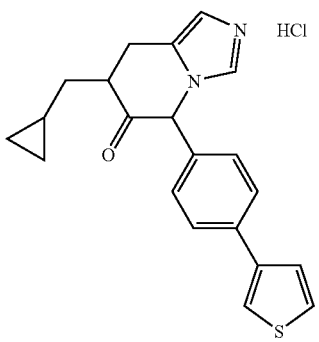

The title compound is prepared analogously to Example 74: m.p. 217-219° C.; $^1$H-NMR (DMSO-d$_6$) δ 9.22 (1H, s), 7.94 (1H, dd, J 2.9, 1.2), 7.78 (2H, d, J 8.3), 7.75 (1H, s), 7.67 (1H, m), 7.57 (1H, dd, J 5.0, 1.3), 7.33 (2H, d, J 8.3), 6.39(1H, s), 4.97(1H, d, J 16.7), 4.84 (1H, d, J 16.7), 3.50 (1H, dd, J 13.8, 7.0), 3.32 (1H, dd, J 13.8, 7.0), 1.03 (1H, m), 0.48 (2H, m), 0.28 (2H, m); $^{13}$C-NMR (DMSO-d$_6$) δ 163.3, 162.7, 140.8, 136.3, 134.2, 134.0, 127.9, 127.7, 127.2, 126.5, 125.4, 122.2, 115.6, 61.2, 51.0, 41.3, 9.1, 3.7, 3.4; e/z (ES) 350 (M+1, 100%); calculated for C$_{20}$H$_{19}$N$_3$OS HCl, C, 62.25; H, 5.22; N, 10.89. found C, 61.89; H, 5.26; N, 10.73.

EXAMPLE 77

7-Benzyl-5-(4'-fluoro-biphenyl-3-yl)-7,8-dihydro-imidazo[1,5-a]pyrazin-6-one hydrochloride

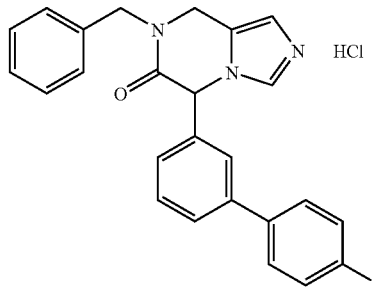

The title compound is prepared analogously to Example 74: m.p. 235-237° C.; $^1$H-NMR (DMSO-d$_6$) δ 9.16 (1H, s), 7.68 (4H, m), 7.54 (2H, m), 7.30 (8H, m), 6.49 (1H, s) 4.75 (4H, m); $^{13}$C-NMR (DMSO-d$_6$) δ 163.61, 162.75, 160.85, 140.46, 136.20, 134.40, 130.32, 129.30, 129.20, 129.05, 128.22, 128.08, 127.95, 126.33, 125.86, 124.98, 116.33, 116.04, 115.89, 61.45, 50.00, 41.28; e/z (ES) 398 (M+1, 100%); calculated for C$_{25}$H$_{20}$FN$_3$O HCl 0.2H$_2$O, C, 68.63; H, 4.93; N, 9.60. found C, 68.35; H, 4.73; N, 9.66.

EXAMPLES 78

5-Biphenyl-4-yl-7-(4-fluoro-benzyl)-7,8-dihydro-imidazo[1,5-a]pyrazin-6-one

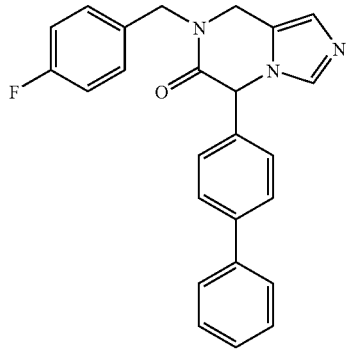

The title compound is prepared analogously to Example 74: m.p. 189-190° C.; e/z (ES) 398 (M+1, 100%).

EXAMPLE 79

7-Benzyl-5-biphenyl-3-yl-7,8-dihydro-imidazo[1,5-a]pyrazin-6-one

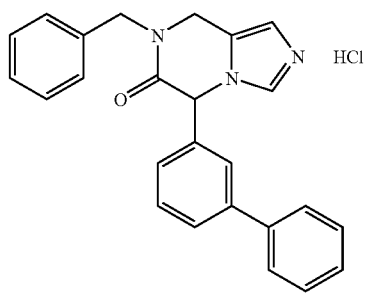

The title compound is prepared analogously to Example 74: m.p. 232-234° C.; e/z (ES) 380 (M+1, 100%).

EXAMPLE 80

Methyl 4-(7-benzyl-6-oxo-5,6,7,8-tetrahydro-imidazo[1,5-a]pyrazin-5-yl)-benzoate hydrochloride

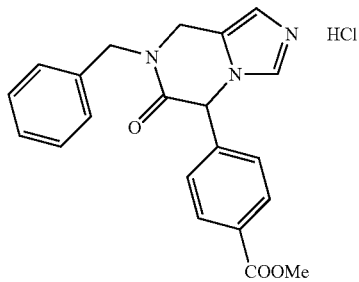

To a solution of the title compound of Example 23, 7-benzyl-5-(4-bromo-phenyl)-7,8-dihydro-imidazo[1,5-a]pyrazin-6-one (0.202 g, 0.53 mmol) in DMSO:MeOH (2 mL; 5:1) are added triethylamine (0.147 mL, 1.06 mmol), diphenylposhinopropane (0.044 g, 20 mol %), and palladium (II) acetate (0.024 g, 20 mol %). The reaction mixture is degassed, purged with carbon monoxide and then heated at 70° C. for 16 h. The reaction mixture is cooled, then partitioned between water and EtOAc. Following washing of the combined organic phases with brine, drying (anhydrous sodium sulfate) the residue is subjected to flash chromatography (silica) eluting with EtOAc:MeOH:NH$_4$OH (90:10:1) to give the desired free base as an oil, which is dissolved in methanol and HCl (g) in diethyl ether is added to afford methyl 4-(7-benzyl-6-oxo-5,6,7,8-tetrahydro-imidazo[1,5-a]pyrazin-5-yl)-benzoate hydrochloride: m.p. 236-238° C.; $^1$H-NMR (DMSO-d$_8$) δ 9.16 (1H, s), 8.01 (2H, d, J=8.4), 7.71 (1H, s), 7.44 (2H, d, 8.4), 7.33 (3H, m), 7.23 (2H, m), 6.58 (1H, s), 4.70 (4H, m), 3.87 (3H, s); $^{13}$C-NMR (DMSO-d$_6$) δ 166.0, 163.2, 139.9, 136.1, 134.5, 130.6, 130.3, 129.0, 128.1, 127.8, 125.2, 115.8, 61.4, 52.7, 49.9, 41.1; e/z (ES) 362 (M+1, 100%); calculated for C$_{21}$H$_{19}$N$_3$O$_3$ HCl 0.2H$_2$O, C, 62.82; H, 5.06; N, 10.50. found C, 62.82; H, 5.06; N, 10.47.

EXAMPLE 81

4-7-Benzyl-5-methyl-6-oxo-5,6,7,8-tetrahydro-imidazo[1,5-a]pyrazin-5-yl)-benzonitrile hydrochloride

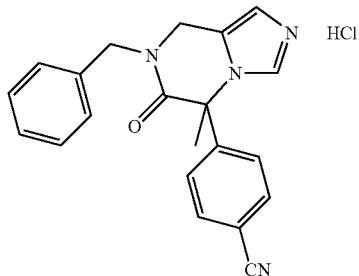

To a solution of the title compound of Example 3, 4-(7-benzyl-5-methyl-6-oxo-5,6,7,8-tetrahydro-imidazo[1,5-a]pyrazin-5-yl)-benzonitrile (0.24 g, 0.63 mmol) in 5 mL of THF at −78° C. is added LHMDS (0.70 mL, 0.70 mmol) and the resulting solution is stirred for 15 min. To this solution is added methyl iodide (0.040 mL, 0.67 mmol) and the solution is stirred for 15 min, then warmed gradually to RT. The reaction mixture is quenched by addition of NH$_4$Cl and extracted with EtOAc. The organic solution is washed with brine, dried (anhydrous sodium sulfate) and evaporated to an oil. Purification by flash chromatography (silica gel) eluting with EtOAc:MeOH:NH$_4$OH (95:5:0.5) gives the free base which is dissolved in acetone and HCl (g) in diethyl ether is added to afford 4-(7-benzyl-5-methyl-6-oxo-5,6,7,8-tetrahydro-imidazo[1,5-a]pyrazin-5-yl)-benzonitrile hydrochloride: m.p. 230-232° C.; $^1$H-NMR (DMSO-d$_6$) δ 9.54 (1H, s), 7.90 (2H, d, J=8.7), 7.74 (1H, s), 7.32 (3H, m), 7.22 (2H, d, J=8.7), 7.15 (2H, m), 4.73 (1H, d, J=16.9), 4.71 (1H, d, J=14.6), 4.66 (1H, d, J=14.6), 4.12 (1H, d, J=16.9), 2.25 (3H, s); $^{13}$C-NMR (DMSO-d$_6$) δ 163.1, 141.1, 133.8, 132.3, 131.3, 126.8, 125.8, 125.7, 124.0, 123.7, 116.2, 114.2, 110.0, 64.6, 48.4, 38.5, 22.6; e/z (ES) 343 (M+1, 100%); calculated for C$_{21}$H$_{18}$N$_4$O HCl, C, 66.58; H, 5.05; N, 14.79. found C, 66.41; H, 5.01; N, 14.80.

EXAMPLE 82

5-(4-Bromo-phenyl)-7-cyclopropylmethyl-5-methyl-7,8-dihydro-imidazo[1,5-a]pyrazin-6-one hydrochloride

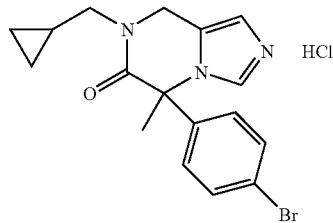

The title compound is prepared analogously to Example 81: m.p. 228-230° C.; $^1$H-NMR (DMSO-d$_6$) δ 9.35 (1H, s), 7.53 (1H, s), 7.39 (2H, d, J=8.4), 6.74 (2H, d, J=8.4), 4.63 (1H, d, J=16.5), 3.99 (1H, d, J=16.5), 3.31 (1H, dd, J=13.8, 7.0), 2.95 (1H, dd, J=13.8, 7.0), 1.91 (3H, s), 0.71 (1H, m), 0.18 (2H, m), 0.0 (2H, m); $^{13}$C-NMR (DMSO-d$_6$) δ 165.4, 162.7, 137.9, 134.3, 132.6, 127.2, 126.4, 122.6, 116.0, 66.7, 51.6, 25.0, 9.0, 3.6, 3.2; e/z (ES) 360/362 (M+1, 100%); calculated for C$_{17}$H$_{18}$BrN$_3$O HCl, C, 51.47; H, 4.83; N, 10.59. found C, 51.15; H, 4.76; N, 10.38.

EXAMPLE 83

5-(3-Bromo-phenyl)-7-cyclopropylmethyl-5-methyl-7,8-dihydro-imidazo[1,5-a]pyrazin-6-one hydrochloride

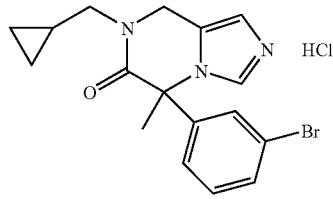

The title compound is prepared analogously to Example 81: m.p. 234-236° C.; $^1$H-NMR (DMSO-d$_6$) δ 0.20-0.34 (2H, m), 0.41-0.49 (2H, m), 0.92-1.04 (1H, m), 2.15 (3H, s), 3.22 (1H, dd, J=13.8, 7.2), 3.55 (1H, dd, J=13.8, 7.2), 4.27 (1H, d, J=16.3), 4.86 (1H, d, J=16.3), 7.00 (1H, d, J=8.0), 7.27 (1H, s), 7.39 (1H, t, J=8.0), 7.62 (1H, d, J=8.0), 7.74 (1H, s), 9.46 (1H, s); $^{13}$C-NMR (DMSO-d$_6$) δ 3.26, 3.49, 9.04, 25.05, 40.86, 51.71, 66.48, 116.54, 122.88, 124.08, 126.18, 127.81, 131.84, 132.30, 134.45, 140.98, 165.40; e/z (ES) 360/362 (M+1, 100%); calculated for C$_{17}$H$_{18}$BrN$_3$O HCl, C, 51.47; H, 4.83; N, 10.59. found C, 51.11; H, 4.87; N, 10.48.

EXAMPLE 84

5-(4-Bromo-phenyl)-7-(4-fluoro-benzyl)-5-methyl-7,8-dihydro-imidazo[1,5-a]pyrazin-6-one hydrochloride

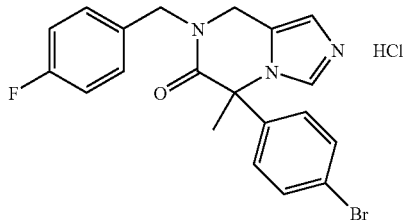

The title compound is prepared analogously to Example 81: m.p. 235-237° C.; $^1$H-NMR (DMSO-d$_6$) δ 9.54 (1H, s), 7.73 (1H, s), 7.61 (2H, d, J=8.7), 7.25 (2H, dd, J=8.7, 5.7), 7.14 (2H, app t, J=8.9), 6.95 (2H, d, J=8.7), 4.72 (1H, d, J=16.6), 4.67 (2H, s), 4.11 (1H, d, J=16.6), 2.2 (3H, s); $^{13}$C-NMR (DMSO-d$_6$) δ 165.7, 162.0 (d, J=243.0), 137.7, 134.4, 132.5, 132.4, 130.3 (d, J=8.3), 127.2, 126.0, 122.7, 116.2, 115.8 (d, J=21.9), 66.7, 49.8, 25.0; e/z (ES) 413/415 (M+1, 100%); calculated for $C_{20}H_{17}BrFN_3O$ HCl, C, 53.29; H, 4.02; N, 9.32. found C, 53.39; H, 3.73; N, 9.28.

EXAMPLE 85

4-[7-(4-Fluoro-benzyl)-5-methyl-6-oxo-5,6,7,8-tetrahydro-imidazo[1,5-a]pyrazin-5-yl]-benzonitrile

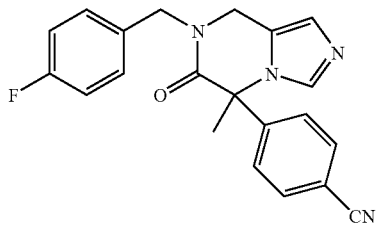

The title compound is prepared analogously to Example 81: m.p. 66-70° C.; $^1$H-NMR (CDCl$_3$) δ 7.70 (s, 1H), 7.61 (d, J=8.3, 2H), 7.11-6.94 (m, 7H), 4.63 (app. t, J=15.0, 2H), 4.32 (d, J=15.5, 1H), 4.00 (d, J=15.7, 1H), 2.22 (s, 3H); $^{13}$C-NMR (CDCl$_3$) δ 167.4, 162.9 (d, J=245.2), 145.5, 134.2, 133.2, 131.4 (d, J=3.0), 130.0 (d, J=8.3), 125.9, 125.0, 123.7, 118.3, 116.3 (d, J=21.0), 113.2, 65.7, 51.0, 41.8, 25.6; MS (m/z) 360.8 (M+1, 100%); calculated for $C_{21}H_{17}FN_4O.0.2H_2O$, C, 69.23; H, 4.78; N, 15.38. found: C, 69.16; H, 4.91; N, 15.18.

EXAMPLE 86

4(7-[(s)-1-(4-Fluoro-phenyl)-ethyl]-5-methyl-6-oxo-5,6,7,8-tetrahydro-imidazo[1,5-a]pyrazin-5-yl]-benzonitrile

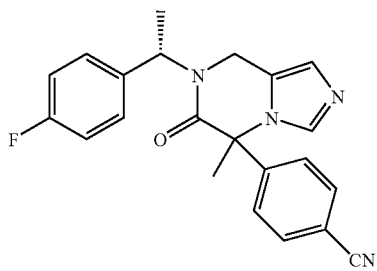

The title compound is prepared analogously to Example 81. The product is obtained as a mixture of diastereomers. The diastereomers may be separated using chromatoraphy on silica.

Diastereomer 1 (less polar): m.p. 78-82° C.; [α]$_D$–3.3 (c 1.00, MeOH); $^1$H-NMR (DMSO-d$_6$) δ 8.05 (s, 1H), 7.89 (d, J=9.0, 2H), 7.37-7.29 (m, 3H), 7.22 (d, J=9.0, 2H), 7.04 (d, J=9.0, 2H), 6.85 (s, 1H), 5.79 (q, J=6.0, 1H), 4.20 (d, J=15.0, 1H), 3.88 (d, J=15.0, 1H), 2.13 (s, 3H), 1.38 (d, J=6.0, 3H); $^{13}$C-NMR (DMSO-d$_6$) δ 166.9, 145.8, 139.8, 134.9, 133.5, 129.0, 127.9, 127.1, 125.8, 123.9, 118.6, 111.6, 65.2, 52.0, 36.5, 25.2, 15.9; MS (m/z) 356.8 (M+1, 100%); calculated for $C_{22}H_{20}N_4O.0.1H_2O$, C, 73.69; H, 5.64; N, 15.63. found, C, 73.29; H, 5.92; N, 15.45.

Diastereomer 2 (more polar): m.p. 72-75° C.; [α]$_D$–147.0 (c 1.00, MeOH); $^1$H-NMR (DMSO-d$_6$) δ 8.02 (s, 1H), 7.84 (d, J=9.0, 2H), 7.26-7.23 (m, 3H), 7.09-7.07 (m, 2H), 7.00 (s, 1H), 6.96 (d, J=6.0, 2H), 5.82 (q, J=9.0, 1H), 4.53 (d, J=15.0, 1H), 3.23 (d, J=15.0, 1H), 2.12 (s, 3H), 1.50 (d, J=9.0, 3H); $^{13}$C NMR (DMSO-ds) δ 164.6, 143.3, 137.1, 132.6, 131.1, 126.6, 125.8, 125.0, 123.7, 122.2, 121.8, 116.4, 109.3, 63.1, 49.7, 34.2, 22.7, 13.4; MS (m/z) 357.1 (M+1, 100%); calculated for $C_{22}H_{20}N_4O.0.1H_2O$, C, 73.69; H, 5.64; N, 15.63. found C, 73.23; H, 5.87; N, 15.12.

EXAMPLE 87

5-Benzyl-5-(4-bromo-phenyl)-7-(4-fluoro-benzyl)-7,8-dihydro-imidazo[1,5-a]pyrazin-6-one

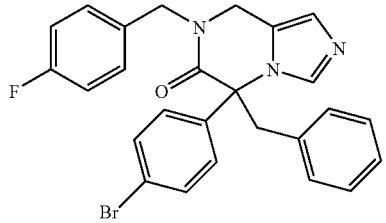

The title compound is prepared analogously to Example 81: m.p. 166-168° C.; $^1$H-NMR (DMSO-d$_6$) δ 7.81 (1H, s), 7.62 (2H, d, J=8.6), 7.14 (7H, m), 7.04 (2H, app t, J=7.5), 6.79 (2H, d, J=7.2), 6.73 (1H, s), 4.75 (1H, d, J=14.5), 4.40 (1H, d, 16.1), 4.28 (1H, d, J=14.5), 4.18 (1H, d, J=13.7), 3.73 (2H, m); $^{13}$C-NMR (DMSO-d$_6$) δ 166.2, 162.0 (d, J=243.8), 141.6, 135.4, 135.1, 132.3, 132.0, 130.6 (d, J=8.3), 130.0, 128.6, 128.3, 127.4, 122.6, 122.5, 122.0, 115.6 (d, J=21.9), 67.67, 49.7, 43.2, 41.7; e/z (E/S) 489/491 (M+1, 100%); calculated for $O_{26}H_{21}BrFN_3O$, C, 63.68; H, 4.32; N, 8.57. found C, 63.68; H, 4.34; N, 8.45.

EXAMPLE 88

4-(5,7-Dibenzyl-6-oxo-5,6,7,8-tetrahydro-imidazol[1,5-a]pyrazin-5-yl)-benzonitrile

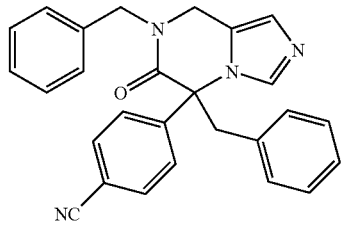

The title compound is prepared analogously to Example 81: m.p. 246-248° C.

EXAMPLE 89

4-(5-Benzyl-7-cyclopropylmethyl-6-oxo-5,6,7,8-tetrahydro-imidazo[1,5-a]pyrazin-5-yl)-benzonitrile

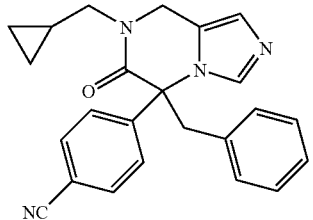

The title compound is prepared analogously to Example 81: m.p. 156-158° C.

EXAMPLE 90

5-(4-Bromophenyl)-7-(4-methoxy-benzyl)-5,6,7,8-tetrahydro-imidazo[1,5-a]-pyrazine dihydrochloride

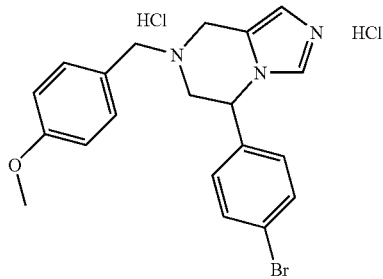

To a solution of the title compound of Example 21, 5-(4-bromo-phenyl)-7-(4-methoxy-benzyl)-7,8-dihydro-imidazo[1,5-a]pyrazin-6-one (0.471 g, 1.14 mmol) in THF (5 mL) at RT is added borane (6.85 mL, 6.85 mmol). The reaction is stirred for 18 h and quenched with MeOH. The reaction mixture is evaporated to dryness, partitioned between water and EtOAc. The combined organic phases are washed with brine, dried (anhydrous sodium sulfate), concentrated and the residue is subjected to flash chromatography (silica) eluting with EtOAc:MeOH:NH$_4$OH (90:10:1) to give the desired material. This material is dissolved in diethyl ether, HCl(g)-MeOH is added and the hydrochloride crystallizes to afford 6(4-bromophenyl)-7-(4-methoxy-benzyl)-5,6,7,8-tetrahydro-imidazo[1,5-a]-pyrazine dihydrochloride: m.p. 270-273° C.

EXAMPLE 91

5-(4-Bromophenyl)-7-benzyl-5,6,7,8-tetrahydro-imidazo[1,5-a]pyrazine p-toluene sulfonate

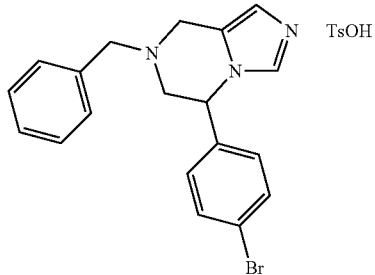

To a solution of the title compound of Example 23, 5-(4-bromo-phenyl)-7-benzyl-7,8-dihydro-imidazo[1,5-a]pyrazin-6-one (0.471 g, 1.14 mmol) in THF (5 mL) at RT is added borane (6.85 mL, 6.85 mmol). The reaction is stirred for 18 h and quenched with MeOH. The reaction mixture is evaporated to dryness, partitioned between water and EtOAc. The combined organic phases are washed with brine, dried (anhydrous sodium sulfate), concentrated and the residue is dissolved in acetone, p-toluene sulfonic acid is added and the desired 5-(4-bromophenyl)-7-benzyl-5,6,7,8-tetrahydro-imidazo[1,5-a]pyrazine p-toluenesulfonate crystallizes: m.p. 223-225° C.; $^1$H-NMR (DMSO-d$_6$) δ 8.81 (1H, s), 7.63 (2H, d, J=8.7), 7.51 (1H, s), 7.47 (2H, d, J=7.8), 7.27 (5H, m), 7.20 (2H, m), 7.11 (2H, d, J=7.8), 5.70 (1H, dd, J=6.4, 4.1), 3.85 (1H, d, J=13.3), 3.78 (1H, d, J=14.9), 3.75 (1H, d, J=13.3), 3.68 (1H, d, J=14.9), 3.17 (1H, dd, J=12.4, 4.1), 2.91 (1H, dd, J=12.4, 6.4), 2.29 (3H, s); $^{13}$C-NMR (DMSO-d$_6$) δ 145.8, 137.9, 137.4, 136.9, 134.3, 131.5, 129.5, 128.7, 128.5, 128.2, 127.9, 127.3, 125.3, 121.8, 114.7, 59.9, 57.5, 55.7, 46.7, 20.7; e/z (ES) 368/370 (M+1, 100%); calculated for C$_{19}$H$_{18}$N$_3$ C$_7$H$_8$SO$_3$, C, 57.78; H, 4.85; N, 7.77. found C, 57.79; H, 4.85; N, 7.73.

EXAMPLE 92

4-(8-Benzyl-7-oxo-6,7,8,9-tetrahydro-5H-imidazo[1,5-a][1,4]diazepin-5-yl)-benzonitrile

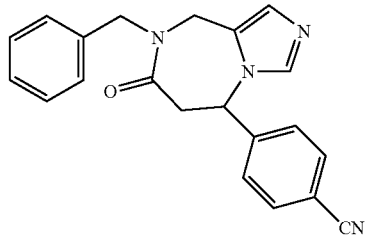

A. Methyl 3-[5-(t-butyl-dimethylsilanyloxymethyl)-imidazol-1-yl]-3-(4-cyano-phenyl)-propionate To a solution of the title E compound in Example 1, 4-(5-t-butyl-dimethylsilanyloxy-methyl-imidazoyi-1-ylmethyl)-benzonitrile (3.15 g, 9.63 mmol) in THF (30 mL) at −78° C. is added dropwise 1.0 M LHMDS (10.0 mL, 10.0 mmol) and stirred for 10 min. Methyl bromoacetate (0.91 mL, 9.63 mmol) is added and the solution stirred for 10 min, then quenched with ammonium chloride. On warming the reaction is partitioned between EtOAc and brine, thereafter the combined organic phases are dried over anhydrous sodium sulfate and removal of the solvents in vacuo yields a viscous oil. The residue is subjected to flash chromatography (silica gel) eluting with EtOAc:MeOH:NH$_4$OH (95:5:0.5) to give methyl 3-[5-(t-butyl-dimethylsilanyloxymethyl)-imidazol-1-yl]-3-(4-cyano-phenyl)-propionate: $^1$H-NMR (CDCl$_3$) δ 7.64 (2H, d, J=8.4), 7.59 (1H, s), 7.28 (2H, d, J=8.4), 6.95 (1H, s), 6.05 (1H, m), 4.62 (1H, d, J=13.2), 4.46 (1H, d, J=13.2), 3.66 (3H, s), 3.32 (1H, dd, J=16.3, 9.4), 3.19 (1H, dd, J=16.3, 7.0), 0.83 (9H, s), 0.02 (3H, s), 0.00 (3H, s); $^{13}$C-NMR (CDCl$_3$) δ 170.0, 144.8, 136.4, 133.1, 131.4, 128.9, 118.5, 112.7, 55.4, 52.7, 40.6, 26.1, 18.8, −5.0, −5.1; e/z (ES) 400 (M+1, 100%).

B. Methyl 3-[5-(hydroxymethyl)-imidazol-1-yl]-3-(4-cyano-phenyl)propionate

The title A compound, methyl 3-[5-(t-butyl-dimethylsilanyloxymethyl)-imidazole-1-yl]-3-(4-cyanophenyl)-propionate (0.98 g, 2.46 mmol) and p-toluenesulfonic acid (0.55 g, 2.9 mmol) are stirred in MeOH (10 mL) at RT for 24 h. The reaction mixture is evaporated to an oil and partitioned between EtOAc and aqueous saturated sodium bicarbonate. The combined organic phases are dried over anhydrous sodium sulfate and removal of the solvent in vacuo yields methyl 3-[5-(hydroxymethyl)-imidazol-1-yl]-3-(4-cyanophenyl)-propionate as an oil: $^1$H-NMR (CDCl$_3$) δ 7.65 (2H, d, J=8.4), 7.62 (1H, s), 7.31 (2H, d, J=8.4), 6.98 (1H, s), 6.05 (1H, dd, J=9.2, 6.2), 4.62 (1H, d, J=13.5), 4.47 (1H, d, J=13.5), 3.67 (3H, s), 3.36 (1H, dd, J=16.5, 9.2), 3.21 (1H, dd, J=16.5, 6.2); e/z (ES) 286 (M+1, 100%).

C. Methyl 3-[5-formyl-imidazol-1-yl]-3-(4-cyano-phenyl)-propionate

To a solution of the title B compound, methyl 3-[5-(hydroxymethyl)-imidazol-1-yl]-3-(4-cyano-phenyl)-propionate (0.60 g, 2.11 mmol) in DCM (7.0 mL) is added Dess-Martin periodinane (15% wt solution, 7.0 mL, 3.2 mmol) and the reaction is stirred for 3 h. The reaction mixture is partitioned between EtOAc and sodium bicarbonate-sodium thiosulfate. The combined organic phases are washed with brine and dried (anhydrous sodium sulfate) and concentrated. The residue is subjected to flash chromatography (silica) eluting with EtOAc:MeOH (9:1) to give methyl 3-[5-formyl-imidazol-1-yl]-3-(4-cyano-phenyl)-propionate as an oil: $^1$H-NMR (CDCl$_3$) δ 9.68 (1H, s), 8.00 (1H, s), 7.87 (1H, s), 7.65 (2H, d, J=8.5), 7.37 (2H, d, J=8.5), 6.63 (1H, m), 3.66 (3H, s), 3.43 (1H, dd, J=16.5, 8.5), 3.30 (1H, dd, J=16.5, 6.6); $^{13}$C-NMR (CDCl$_3$) δ 178.9, 169.2, 144.9, 143.0, 141.8, 132.7, 130.8, 127.4, 118.0, 112.5, 56.5, 52.4, 39.0; e/z (ES) 284 (M+1, 100%).

D. 4-(8-Benzyl-7-oxo-6,7,8,9-tetrahydro-5H-imidazo[1,5-a][1,4]diazepin-5-yl)-benzonitrile To a solution of the title C compound, methyl 3-[5-formyl-imidazol-1-yl]-3-(4-cyano-phenyl)-propionate (0.22 g, 0.78 mmol) in DCE (5 mL) is added benzylamine (0.100 mL, 0.92 mmol) followed by sodium triacetoxyborohydride (0.49 g, 2.3 mmol). The reaction mixture is stirred at RT for 16 h, then partitioned between EtOAc and saturated aqueous sodium bicarbonate, and the organic solution is washed with brine, dried (anhydrous sodium sulfate) and concentrated. The residue is subjected to flash chromatography (silica) eluting with EtOAc:MeOH:NH$_4$OH (90:10:1) to give 4-(8-benzyl-7-oxo-6,7,8,9-tetrahydro-5H-imidazo[1,5-a][1,4]diazepin-5-yl)-benzonitrile: m.p. 65° C.; e/z (ES) 343 (M+1, 100%).

EXAMPLE 93

4-(8-Cyclopropylmethyl-7-oxo-6,7,8,9-tetrahydro-5H-imidazo[1,5-a][1,4]diazepin-5-yl)-benzonitrile

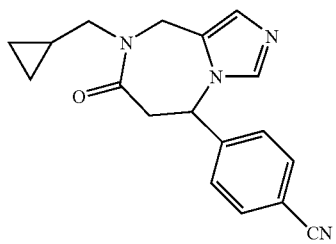

The title compound is prepared analogously to Example 92: m.p. 178-180° C.; e/z (ES) 307 (M+1, 100%).

What is claimed is:
1. A compound of the formula

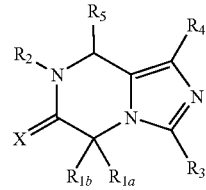

wherein
X is oxygen or H$_2$;
R$_{1a}$ is a monocyclic or bicyclic aryl or, monocyclic heteroaryl;
R$_{1b}$ is hydrogen, alkyl, or aralkyl;
R$_2$ is R$_6$—(CHR$_7$)$_p$— in which
R$_6$ is alkyl, cycloalkyl, aryl or monocyclic heterocyclyl;
R$_7$ is hydrogen, alkyl, aryl, monocyclic heteroaryl or aralkyl;
p is zero or an integer from 1 to 4;
R$_3$ and R$_4$ are independently hydrogen; or
R$_5$ is hydrogen;
in which each alkyl is optionally substituted with halo, hydroxy, cycloalkyl, alkanoyl, alkoxy, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, carboxy, alkoxycarbonyl, aryl, alkenyl, alkynyl, araloxy, guanidino and monocyclic heterocyclyl; and
each aryl is optionally substituted with alkyl, trifluoromethyl, cycloalkyl, halo, hydroxy, alkoxy, acyl, alkanoyloxy, aryloxy, amino, thiol, alkylthio, arylthio, nitro, cyano, carboxy, alkoxycarbonyl, carbamoyl, alkylthiono, sulfonyl, sulfonamido and monocyclic heterocyclyl; and
each cycloalkyl is optionally substituted with alkyl, halo, oxo, hydroxy, alkoxy, alkanoyl, acylamino, carbamoyl, alkylamino, dialkylamino, thiol, alkylthio, nitro, cyano, carboxy, alkoxycarbonyl, sulfonyl, sulfonamido, sulfamoyl and monocyclic heterocyclyl; and
each heterocyclyl and heteroaryl are independently optionally substituted with alkyl, hydroxy, halo, oxo, amino, alkylamino, dialkylamino, alkoxy, cycloalkyl, carboxy, alkoxycarbonyl, mercapto, cyano, nitro, sulfamoyl, sulfonamido, aryl, alkanoyloxy, aroyloxy, arylthio, aryloxy, alkylthio, formyl, carbamoyl, aryl and arylalkyl; and
each heteroaryl is selected from 2-pyridyl, 3-pyridyl, 4-pyridyl, 2-thienyl, 3-thienyl, 2-furyl or 3-furyl; and
each heterocyclyl is selected from morpholinyl, 2-thienyl, 3-thienyl, piperidinyl, 2-furyl, 3-furyl, 2-pyridyl, 3-pyridyl or 4-pyridyl;
or a pharmaceutically acceptable salt thereof; or a diastereomer thereof; or a mixture of diastereomers thereof; or an optical isomer thereof; or a mixture of optical isomers thereof.
2. The compound according to claim 1 of formula IA (IA)

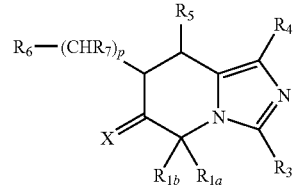

wherein
X is oxygen or H$_2$;
R$_{1a}$ is monocyclic or bicyclic aryl or monocyclic heteroaryl;

$R_{1b}$ is hydrogen, lower alkyl or aralkyl;
$R_6$ is cycloalkyl, aryl or monocyclic heteroaryl;
$R_7$ is hydrogen or lower alkyl;
p is zero or an integer of 1 or 2;
$R_3$, $R_4$ and $R_5$ are hydrogen;
or a pharmaceutically acceptable salt thereof; or a diastereomer thereof; or a mixture of diastereomers thereof; or an optical isomer thereof; or a mixture of optical isomers thereof.

3. The compound according to claim 2 wherein
$R_{1a}$ is monocyclic aryl;
$R_{1b}$ is hydrogen, lower alkyl or aralkyl;
or a pharmaceutically acceptable salt thereof; or a diastereomer thereof; or a mixture of diastereomers thereof; or an optical isomer thereof; or a mixture of optical isomers thereof.

4. The compound according to claim 3 of formula IB

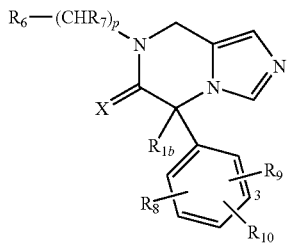

(IB)

wherein
X is oxygen or $H_2$;
$R_{1b}$ is hydrogen, lower alkyl or aralkyl;
$R_6$ is cycloalkyl, aryl or monocyclic heteroaryl;
$R_7$ is hydrogen or lower alkyl;
p is zero or an integer of 1 or 2;
$R_8$, $R_9$ and $R_{10}$ are independently hydrogen, hydroxy, halogen, cyano, nitro, trifluoromethyl, optionally substituted alkyl, cycloalkyl, optionally substituted amino, alkoxy, alkylthio, carboxy, sulfonyl, carbamoyl, aryl, aryloxy, arylthio or monocyclic heterocyclyl;
or a pharmaceutically acceptable salt thereof; or a diastereomer thereof; or a mixture of diastereomers thereof; or an optical isomer thereof; or a mixture of optical isomers thereof.

5. The compound according to claim 4 of wherein
X is oxygen or $H_2$;
$R_{1b}$ is hydrogen, lower alkyl or aralkyl;
$R_6$ is cycloalkyl, aryl or monocyclic heteroaryl;
$R_7$ is hydrogen or lower alkyl;
p is an integer of 1;
$R_8$ is hydrogen;
$R_9$ is hydrogen, halogen, cyano or trifluoromethyl;
$R_{10}$ is halogen, cyano or trifluoromethyl;
or a pharmaceutically acceptable salt thereof; or a diastereomer thereof; or a mixture of diastereomers thereof; or an optical isomer thereof; or a mixture of optical isomers thereof.

6. The compound according to claim 5 wherein
X is oxygen;
or a pharmaceutically acceptable salt thereof; or a diastereomer thereof; or a mixture of diastereomers thereof; or an optical isomer thereof; or a mixture of optical isomers thereof.

7. The compound according to claim 5 wherein
$R_6$ is $C_{3-6}$cycloalkyl, monocyclic aryl or monocyclic heteroaryl;
or a pharmaceutically acceptable salt thereof; or a diastereomer thereof; or a mixture of diastereomers thereof; or an optical isomer thereof; or a mixture of optical isomers thereof.

8. The compound according to claim 5 wherein
$R_{10}$ is located at the 3-position;
or a pharmaceutically acceptable salt thereof; or a diastereomer thereof; or a mixture of diastereomers thereof; or an optical isomer thereof; or a mixture of optical isomers thereof.

9. The compound according to claim 1 which is selected from:
4-(7-Cyclopropylmethyl-6-oxo-5,6,7,8-tetrahydro-imidazo[1,5-a]pyrazin-5-yl)-benzonitrile;
4-(7-Methyl-6-oxo-5,6,7,8-tetrahydro-imidazo[1,5-a]pyrazin -5-yl)-benzonitrile;
4-(7-Benzyl-6-oxo-5,6,7,8-tetrahydro-imidazo[1,5-a]pyrazin -5-yl)-benzonitrile;
4-(7-Allyl-6-oxo-5,6,7,8-tetrahydro-imidazo[1,5-a]pyrazin -5-yl)-benzonitrile;
4-(6-Oxo-7-propyl-5,6,7,8-tetrahydro-imidazo[1,5-a]pyrazin -5-yl)-benzonitrile;
4-(7-Isopropyl-6-oxo-5,6,7,8-tetrahydro-imidazo[1,5-a]pyrazin-5-yl)-benzonitrile;
4-{7-[2-(4-Fluoro-phenyl)-ethyl]-6-oxo-5,6,7,8-tetrahydro-imidazo[1,5-a]pyrazin-5-yl}-benzonitrile;
4-[7-(3-Morpholin-4-yl-propyl)-6-oxo-5,6,7,8-tetrahydro -imidazo[1,5-a]pyrazin-5-yl]-benzonitrile;
7-(4-Methoxy-benzyl)-5-(4-thiophen-3-yl-phenyl)-7,8-dihydro-imidazo[1,5-a]pyrazin-6-one;
4-[7-(4-Methyl-benzyl)-6-oxo-5,6,7,8-tetrahydro-imidazo[1,5-a]pyrazin-5-yl]-benzonitrile;
4-[7-(4-Chloro-benzyl )-6-oxo-5,6,7,8-tetrahydro-imidazo[1,5-a]pyrazin-5-yl]-benzonitrile;
4-[6-Oxo-7-(4-trifluoromethyl-benzyl)- 5,6,7,8-tetrahydro -imidazo[1,5-a]pyrazin-5-yl)-benzo nitrile;
4-[6-Oxo-7-(3-methyl-benzyl)-5,6,7,8-tetrahydro-imidazo[1,5-a]pyrazin-5-yl)-benzonitrile;
4-[6-Oxo-7-(4-fluoro-benzyl)-5,6,7,8-tetrahydro-imidazo[1,5-a]pyrazin-5-yl)-benzonitrile;
4-[6-Oxo-7-(3-trifluoromethyl-benzyl)-5,6,7,8-tetrahydro-imidazo[1,5-a]pyrazin-5-yl )-benzonitrile;
4-[6-Oxo-7-(3,4-dichloro-benzyl)-5,6,7,8-tetrahydro-imidazo[1,5-a]pyrazin-5-yl)-benzonitrile;
4-(7-Cyclopropyl-6-oxo-5,6,7,8-tetrahydro-imidazo[1,5-a]pyrazin-5-yl)-benzonitrile;
4-(7-Cyclohexyl -6-oxo-5,6,7,8-tetrahydro-imidazo[1,5-a]pyrazin-5-yl )-benzonitrile;
4-(7-Cyclopentyl -6-oxo-5,6,7,8-tetrahydro-imidazo[1,5-a]pyrazin-5-yl )-benzonitrile;
4-[7-(2-Methoxyethyl)-6-oxo-5,6,7,8-tetrahydro-imidazo[1,5-a]pyrazin-5-yl]-benzonitrile;
4-[7-(3-Methoxypropyl )-6-oxo-5,6,7,8-tetrahydro-imidazo[1,5-a]pyrazin-5-yl]-benzonitrile;
4-(6-Oxo-7-pyridin-4-ylmethyl -5,6,7,8-tetrahydro-imidazo[1,5-a]pyrazin-5-yl)-benzonitrile;
7-Benzyl-5-phenyl-7,8-dihydro-imidazo[1,5-a]pyrazin-6-one;
7-Methyl-5-phenyl-7,8-dihydro-imidazo[1,5-a]pyrazin-6-one;
5-(4-Bromo-phenyl)-7-methyl -7,8-dihydro-imidazo[1,5-a]pyrazin-6-one;
5-(4-Bromo-phenyl)-7-(4-methoxy-benzyl)-7,8-dihydro-imidazo[1,5-a]pyrazin-6-one;
5-(4-Bromo-phenyl)-7-cyclopropylmethyl-7,8-dihydro-imidazo[1,5-a]pyrazin-6-one;
7-Benzyl-5-(4-bromo-phenyl)-7,8-dihydro-imidazo[1,5-a]pyrazin-6-one;
5-(4-Bromo-phenyl)-7-(4-chloro-benzyl)-7,8-dihydro-imidazo[1,5-a]pyrazin-6-one;
5-(4-Bromo-phenyl)-7-(4-trifluoromethyl-benzyl)-7,8-dihydro-imidazo[1,5-a]pyrazin-6-one;
5-(4-Bromo-phenyl)-7-(4-methoxy-phenyl)-7,8-dihydro-imidazo[1,5-a]pyrazin-6-one;

5-(4-Bromo-phenyl)-7-(4-fluoro-phenethyl)-7,8-dihydro-imidazo[1,5-a]pyrazin-6-one;
5-(4-Bromo-phenyl)-7-(4-fluoro-benzyl)-7,8-dihydro-imidazo[1,5-a]pyrazin-6-one;
5-(3-Bromo-phenyl)-7-methyl-7,8-dihydro-imidazo[1,5-a]pyrazin-6-one;
5-(3-Bromo-phenyl)-7-cyclohexyl-7,8-dihydro-imidazo[1,5-a]pyrazin-6-one;
5-(3-Bromo-phenyl)-7-(4-methoxy-phenyl)-7,8-dihydro-imidazo[1,5-a]pyrazin-6-one;
5-(3-Bromo-phenyl)-7-cyclopropylmethyl-7,8-dihydro-imidazo[1,5-a]pyrazin-6-one;
7-Benzyl-5-(3-bromo-phenyl)-7,8-dihydro-imidazo[1,5-a]pyrazin-6-one;
5-(3-Bromo-phenyl)-7-(4-methoxy-benzyl)-7,8-dihydro-imidazo[1,5-a]pyrazin-6-one;
5-(3-Bromo-phenyl)-7-(4-fluoro-benzyl)-7,8-dihydro-imidazo[1,5-a]pyrazin-6-one;
5-(3-Bromo-phenyl)-7-(4-chloro-benzyl)-7,8-dihydro-imidazo[1,5-a]pyrazin-6-one;
5-(3-Bromo-phenyl)-7-(4-methyl-benzyl)-7,8-dihydro-imidazo[1,5-a]pyrazin-6-one;
5-(3-Bromo-phenyl)-7-(4-trifluoromethyl-benzyl)-7,8-dihydro-imidazo[1,5-a]pyrazin-6-one;
5-(3-Bromo-phenyl)-7-(3-trifluoromethyl-benzyl)-7,8-dihydro-imidazo[1,5-a]pyrazin-6-one;
5-(3-Bromo-phenyl)-7-(3-fluoro-benzyl)-7,8-dihydro-imidazo[1,5-a]pyrazin-6-one;
5-(3-Bromo-phenyl)-7-(3-methyl-benzyl)-7,8-dihydro-imidazo[1,5-a]pyrazin-6-one;
5-(3-Bromo-phenyl)-7-(phenethyl)-7,8-dihydro-imidazo[1,5-a]pyrazin-6-one;
5-(3-Bromo-phenyl)-7-(4-methoxy-phenethyl)-7,8-dihydro-imidazo[1,5-a]pyrazin-6-one;
5-(3-Bromo-phenyl)-7-(4-chloro-phenethyl)-7,8-dihydro-imidazo[1,5-a]pyrazin-6-one;
5-(3-Bromo-phenyl)-7-(3-chloro-phenethyl)-7,8-dihydro-imidazo[1,5-a]pyrazin-6-one;
5-(3-Bromo-phenyl)-7-(4-methyl-phenethyl)-7,8-dihydro-imidazo[1,5-a]pyrazin-6-one;
5-(3-Bromo-phenyl)-7-(4-fluoro-phenethyl)-7,8-dihydro-imidazo[1,5-a]pyrazin-6-one;
5-(3-Bromo-phenyl)-7-thiophen-2-ylmethyl-7,8-dihydro-imidazo[1,5-a]pyrazin-6-one;
5-(3-Bromo-phenyl)-7-furan-2-ylmethyl-7,8-dihydro-imidazo[1,5-a]pyrazin-6-one;
5-(3-Bromo-phenyl)-7-thiophen-3-ylmethyl-7,8-dihydro-imidazo[1,5-a]pyrazin-6-one;
5-(3-Bromo-phenyl)-7-furan-3-ylmethyl-7,8-dihydro-imidazo[1,5-a]pyrazin-6-one;
5-(3-Bromo-phenyl)-7-pyridin-3-ylmethyl-7,8-dihydro-imidazo[1,5-a]pyrazin-6-one;
5-(3-Bromo-phenyl)-7-pyridin-2-ylmethyl-7,8-dihydro-imidazo[1,5-a]pyrazin-6-one;
5-(3-Bromo-phenyl)-7-pyridin-4-ylmethyl-7,8-dihydro-imidazo[1,5-a]pyrazin-6-one;
5-(3-Bromo-phenyl)-7-cyclohexylmethyl-7,8-dihydro-imidazo[1,5-a]pyrazin-6-one;
4-[5-(3-Bromo-phenyl)-6-oxo-5,6-dihydro-8H-imidazo[1,5-a]pyrazin-7-ylmethyl-piperidine-1-carboxylic acid t-butyl ester;
5-(3-Bromo-phenyl)-7-piperidin-4-ylmethyl-7,8-dihydro-imidazo[1,5-a]pyrazin-6-one;
(R)-5-(3-Bromo-phenyl)-7-((R)-1-phenyl-ethyl)-7,8-dihydro-imidazo[1,5-a]pyrazin-6-one;
(S)-5-(3-Bromo-phenyl)-7-((R)-1-phenyl-ethyl)-7,8-dihydro-imidazo[1,5-a]pyrazin-6-one;
(R)-5-(3-Bromo-phenyl)-7-((S)-1-phenyl-ethyl)-7,8-dihydro-imidazo[1,5-a]pyrazin-6-one;
(S)-5-(3-Bromo-phenyl)-7-((S)-1-phenyl-ethyl)-7,8-dihydro-imidazo[1,5-a]pyrazin-6-one;
(R)-5-(4-Bronno-phenyl)-7-((R)-1-phenyl-ethyl)-7,8-dihydro-imidazo[1,5-a]pyrazin-6-one;
(S)-5-(4-Bromo-phenyl)-7-((R)-1-phenyl-ethyl)-7,8-dihydro-imidazo[1,5-a]pyrazin-6-one;
(R)-5-(4-Bromo-phenyl)-7-((S)-1-phenyl-ethyl)-7,8-dihydro-imidazo[1,5-a]pyrazin-6-one;
(S)-5-(4-Bromo-phenyl)-7-((S)-1-phenyl-ethyl)-7,8-dihydro-imidazo[1,5-a]pyrazin-6-one;
4-[(R)-6-Oxo-7-((S)-1-phenyl-ethyl)-5,6,7,8-tetrahydro-imidazo[1,5-a]pyrazin-5-yl]-benzonitrile;
4-[(S)-6-Oxo-7-((S)-1-phenyl-ethyl)-5,6,7,8-tetrahydro-imidazo[1,5-a]pyrazin-5-yl]-benzonitrile;
7-Benzyl-7,8-dihydro-imidazo[1,5-a]pyrazin-6-one;
7-(4-Methyl-benzyl)-7,8-dihydro-imidazo[1,5-a]pyrazin-6-one;
7-(4-Fluoro-benzyl)-7,8-dihydro-imidazo[1,5-a]pyrazin-6-one;
3-(7-Benzyl-6-oxo-5,6,7,8-tetrahydro-imidazo[1,5-a]pyrazin-5-yl)-benzonitrile;
3-[7-(4-Methyl-benzyl)-6-oxo-5,6,7,8-tetrahydro-imidazo[1,5-a]pyrazin-5-yl]-benzonitrile;
3-[7-(4-Fluoro-benzyl)-6-oxo-5,6,7,8-tetrahydro-imidazo[1,5-a]pyrazin-5-yl]-benzonitrile;
3-[7-(4-Chloro-benzyl)-6-oxo-5,6,7,8-tetrahydro-imidazo[1,5-a]pyrazin-5-yl]-benzonitrile;
3-[7-(4-Methoxy-benzyl)-6-oxo-5,6,7,8-tetrahydro-imidazo[1,5-a]pyrazin-5-yl]-benzonitrile;
3-[7-(4-Fluoro-phenethyl)-6-oxo-5,6,7,8-tetrahydro-imidazo[1,5-a]pyrazin-5-yl]-benzonitrile;
3-(7-Phenethyl-6-oxo-5,6,7,8-tetrahydro-imidazo[1,5-a]pyrazin-5-yl)-benzonitrile;
3-(7-Cyclopropylmethyl-6-oxo-5,6,7,8-tetrahydro-imidazo[1,5-a]pyrazin-5-yl)-benzonitrile;
5-(4'-Chloro-biphenyl-4-yl)-7-(4-methoxy-benzyl)-7,8-dihydro-imidazo[1,5-a]pyrazin-6-one;
7-(4-Methoxy-benzyl)-5-(4-thiophen3-yl-phenyl)-7,8-dihydro-imidazo[1,5-a]pyrazin-6-one;
7-Cyclopropylmethyl-5-(4-thiophen-3-yl-phenyl)-7,8-dihydro-imidazo[1,5-a]pyrazin-6-one;
7-Benzyl-5-(4'-fluoro-biphenyl-3-yl)-7,8-dihydro-imidazo[1,5-a]pyrazin-6-one;
5-Biphenyl-4-yl-7-(4-fluoro-benzyl)-7,8-dihydro-imidazo[1,5-a]pyrazin-6-one;
7-Benzyl-5-biphenyl-3-yl-7,8-dihydro-imidazo[1,5-a]pyrazin-6-one;
Methyl 4-(7-benzyl-6-oxo-5,6,7,8-tetrahydro-imidazo[1,5-a]pyrazin-5-yl)-benzoate;
4-(7-Benzyl-5-methyl-6-oxo-5,6,7,8-tetrahydro-imidazo[1,5-a]pyrazin-5-yl)-benzonitrile;
5-(4-Bromo-phenyl)-7-cyclopropylmethyl-5-methyl-7,8-dihydro-imidazo[1,5-a]pyrazin-6-one;
5-(3-Bromo-phenyl)-7-cyclopropylmethyl-5-methyl-7,8-dihydro-imidazo[1,5-a]pyrazin-6-one;
5-(4-Bromo-phenyl)-7-(4-fluoro-benzyl)-5-methyl-7,8-dihydro-imidazo[1,5-a]pyrazin-6-one;
4-[7-(4-Fluoro-benzyl)-5-methyl-6-oxo-5,6,7,8-tetrahydro-imidazo[1,5-a]pyrazin-5-yl]-benzonitrile;
4-{(R)-7-[(S)-1-(4-Fluoro-phenyl)-ethyl]-5-methyl-6-oxo-5,6,7,8-tetrahydro-imidazo[1,5-a]pyrazin-5-yl}-benzonitrile;
4-{(S)-7-[(S)-1-(4-Fluoro-phenyl)-ethyl]-5-methyl-6-oxo-5,6,7,8-tetrahydro-imidazo[1,5-a]pyrazin-5-yl}-benzonitrile;
5-Benzyl-5-(4-bromo-phenyl)-7-(4-fluoro-benzyl)-7,8-dihydro-imidazo[1,5-a]pyrazin-6-one;
4-(5,7-Dibenzyl-6-oxo-5,6,7,8-tetrahydro-imidazo[1,5-a]pyrazin-5-yl)-benzonitrile;

4-(5-Benzyl-7-cyclopropylmethyl-6-oxo-5,6,7,8-tetrahydro-imidazo[1,5-a]pyrazin-5-yl)-benzonitrile;

5-(4-Bromophenyl)-7-(4-methoxy-benzyl)-5,6,7,8-tetrahydro-imidazo[1,5-a]-pyrazine;

or a pharmaceutically acceptable salt thereof; or an optical isomer thereof; or a mixture of optical isomers thereof.

10. A pharmaceutical composition, comprising:
the compound of claim 1 and
one or more pharmaceutically acceptable carriers.

11. The compound according to claim 1 wherein
X is oxygen or $H_2$;
$R_{1a}$ is a monocyclic or bicyclic aryl optionally substituted with halo, cyano, alkoxy, alkyl optionally substituted with halo, cycloalkyl and alkoxycarbonyl;
$R_{1b}$ is hydrogen, alkyl, or aralkyl;
$R_2$ is $R_6$—$(CHR_7)_p$— in which $R_6$ is cycloalkyl; alkyl optionally substituted with alkoxy and halo; aryl optionally substituted with halo, alkoxycarbonyl, alkoxy, alkyl, alkyl substituted with halo; or a monocyclic heterocyclyl optionally substituted with alkyl and alkoxycarbonyl;
$R_7$ is hydrogen, alkyl, aryl or aralkyl;
p is zero or an integer from 1 to 4;
$R_3$ and $R_4$ are independently hydrogen; or
$R_4$—C may be replaced by nitrogen;
$R_5$ is hydrogen;
or a pharmaceutically acceptable salt thereof; or a diastereomer thereof; or a mixture of diastereomers thereof; or an optical isomer thereof; or a mixture of optical isomers thereof.

* * * * *